(12) United States Patent
Fogarty et al.

(10) Patent No.: US 12,125,067 B1
(45) Date of Patent: Oct. 22, 2024

(54) MACHINE LEARNING SYSTEMS FOR AUTOMATED DATABASE ELEMENT PROCESSING AND PREDICTION OUTPUT GENERATION

(71) Applicant: Cigna Intellectual Property, Inc., Wilmington, DE (US)

(72) Inventors: David J. Fogarty, Old Greenwich, CT (US); Robert E. Chudzik, Marlborough, CT (US); Yogendra D. Bhosrekar, Bolton, CT (US); Stephanie C. Swain, Simsbury, CT (US); Man Tat Lam, Hong Kong (HK); Man Hin Wong, Hong Kong (HK); Margaret A. Shaw, East Hampton, CT (US); Yee Wah Eva Lee, South Windsor, CT (US); Sourav Maharana, Bhubaneswar (IN)

(73) Assignee: Cigna Intellectual Property, Inc., Wilmington, DE (US)

( * ) Notice: Subject to any disclaimer, the term of this patent is extended or adjusted under 35 U.S.C. 154(b) by 518 days.

(21) Appl. No.: 17/136,466

(22) Filed: Dec. 29, 2020

Related U.S. Application Data

(63) Continuation of application No. 17/136,395, filed on Dec. 29, 2020.
(Continued)

(51) Int. Cl.
*G06Q 30/0251* (2023.01)
*G06F 18/2113* (2023.01)
(Continued)

(52) U.S. Cl.
CPC ..... *G06Q 30/0269* (2013.01); *G06F 18/2113* (2023.01); *G06F 18/24155* (2023.01);
(Continued)

(58) Field of Classification Search
None
See application file for complete search history.

(56) References Cited

U.S. PATENT DOCUMENTS

| 7,593,920 B2 | 9/2009 | Jackson |
| 8,458,025 B2 | 6/2013 | Kuo |

(Continued)

OTHER PUBLICATIONS

Ghahramani (Probabilistic machine learning and artificial intelligence. Nature 521, 452-459 (2015) (Year: 2015).*

*Primary Examiner* — Christopher B Tokarczyk
(74) *Attorney, Agent, or Firm* — Harness IP

(57) ABSTRACT

A computer system includes memory hardware configured to store a machine learning model, historical feature vector inputs, and computer-executable instructions, and processor hardware configured to execute the instructions. The instructions include training a first machine learning model with the historical feature vector inputs to generate a title score output, and training a second machine learning model with the historical feature vector inputs to generate a background score output. For each entity in a set, the instructions include processing a title feature vector input with the first machine learning model, and processing a background feature vector with a second machine learning model, to generate a tittle score output and a background score output each indicative of a likelihood that the entity is a decision entity. The instructions include automatically distributing structured campaign data to the entity based on the title score output and the background score output.

10 Claims, 29 Drawing Sheets

Related U.S. Application Data

(60) Provisional application No. 62/955,006, filed on Dec. 30, 2019.

(51) Int. Cl.
  *G06F 18/2415*  (2023.01)
  *G06N 20/20*   (2019.01)
  *G06Q 10/1057* (2023.01)
  *G06Q 30/0201* (2023.01)
  *G06Q 30/0204* (2023.01)

(52) U.S. Cl.
  CPC ......... *G06N 20/20* (2019.01); *G06Q 10/1057* (2013.01); *G06Q 30/0201* (2013.01); *G06Q 30/0204* (2013.01)

(56) References Cited

U.S. PATENT DOCUMENTS

| | | |
|---|---|---|
| 10,074,143 B2 | 9/2018 | Wang |
| 10,311,376 B2 | 6/2019 | Reddy |
| 10,791,136 B2 | 9/2020 | Zoldi |
| 10,853,489 B2 | 12/2020 | Savir |
| 10,861,439 B2 | 12/2020 | Doyle |
| 10,990,894 B2 | 4/2021 | Shaashua |
| 2014/0156411 A1* | 6/2014 | Murgai ............... G06Q 30/0269 705/14.66 |
| 2014/0279739 A1* | 9/2014 | Elkington ............. G06N 20/00 706/12 |
| 2015/0310487 A1 | 10/2015 | Xu |
| 2016/0357790 A1 | 12/2016 | Elkington |
| 2017/0213280 A1* | 7/2017 | Kaznady ................ G06Q 40/03 |
| 2018/0101771 A1 | 4/2018 | Schwarm |
| 2018/0150864 A1 | 5/2018 | Kolb |
| 2018/0285886 A1 | 10/2018 | Yan |
| 2019/0050813 A1 | 2/2019 | Guo |
| 2019/0102693 A1 | 4/2019 | Yates |
| 2019/0259033 A1 | 8/2019 | Surendra |
| 2019/0325354 A1 | 10/2019 | Rajnayak |
| 2019/0333162 A1* | 10/2019 | Wang ..................... G06N 20/20 |
| 2020/0074874 A1 | 3/2020 | Lathrop |
| 2020/0233874 A1 | 7/2020 | Chittar |
| 2020/0279191 A1 | 9/2020 | Koch |
| 2020/0356878 A1 | 11/2020 | Lakshmipathy |
| 2020/0356900 A1 | 11/2020 | Briancon |
| 2020/0401932 A1 | 12/2020 | Kumar |

* cited by examiner

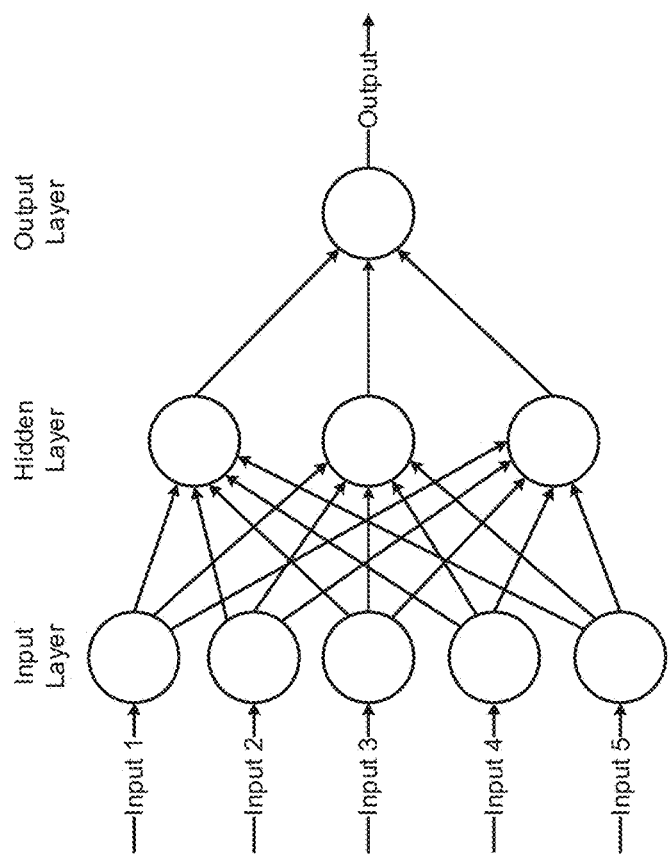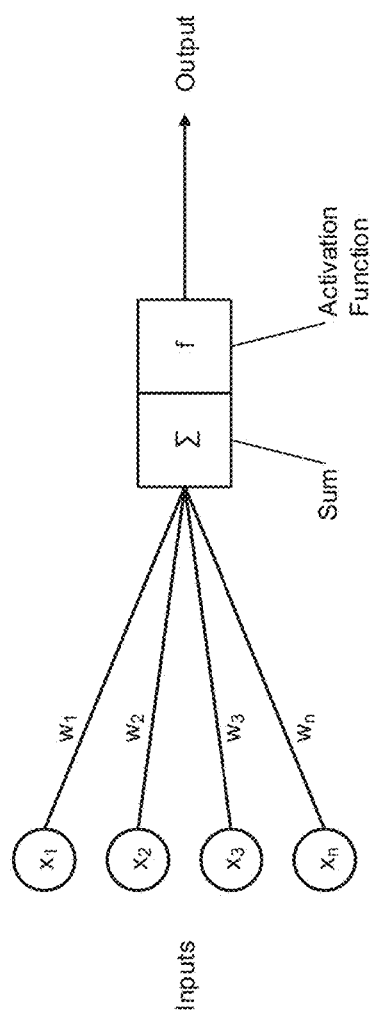
FIG. 3A
FIG. 3B

MACHINE LEARNING SYSTEMS FOR AUTOMATED DATABASE ELEMENT PROCESSING AND PREDICTION OUTPUT GENERATION

CROSS-REFERENCE TO RELATED APPLICATION

This application is a continuation of U.S. patent application Ser. No. 17/136,395 filed Dec. 29, 2020 and claims the benefit of U.S. Provisional Application No. 62/955,006, filed Dec. 30, 2019. The entire disclosure of the above applications are incorporated by reference.

FIELD

The present disclosure relates to machine learning systems for automated database element processing and prediction output generation.

BACKGROUND

Health plan providers typically implement health plan campaigns for purposes of enrolling new individuals in health insurance plans, signing up new employers to provide employer-sponsored health plans for their employees, and providing preventive health care information to reduce future health expenditures. Separately, machine learning models are often used to predict outputs from large input datasets, and to study relationships among multiple input variables.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computerized method of automatic distributed communication includes training a machine learning model with historical feature vector inputs to generate a service score output. The historical feature vector inputs include historical service data structures specific to multiple historical entities, and historical structured firmographic data. The method includes obtaining a set of entities, and for each entity in the set of entities, obtaining structured firmographic data associated with the entity from a structured firmographic database, generating a feature vector input according to the obtained structured firmographic data, and processing, by the machine learning model, the feature vector input to generate the service score output. The service score output is indicative of a likelihood that the entity is a service-providing entity. The method includes selectively including the entity in a subset of entities based on a comparison of the service score output to a threshold value, and for each entity in the subset of entities, identifying a set of targets associated with the entity and automatically distributing structured campaign data to the identified set of targets.

In other features, the training includes classifying each one of the multiple historical entities as a service-providing entity or a non-service-providing entity according to the historical service data structures, and training the machine learning model using the classifications for supervised learning. In other features, the training includes removing each historical entity having a number of employees below an employee count threshold.

In other features, the classifying includes classifying a historical entity as a service-providing entity in response to determining that the historical entity is enrolled in an employer-sponsored health insurance database. In other features, the classifying includes identifying a consumer enrolled in an individual family plan (IFP) database, determining one of the multiple historical entities that employs the identified consumer, and classifying the determined historical entity as a non-service-providing entity.

In other features, the determining includes determining whether the identified consumer is a full-time employee, and only determining the one of the historical entities that employs the identified consumer and classifying the determined historical entity in response to the identified consumer being a full-time employee. In other features, the training includes at least one of preprocessing the historical structured firmographic data to transform one or more variables associated with the historical structured firmographic data into binary dummy variables, performing a bivariate analysis to determine an association between at least one dependent variable and at least one independent firmographic variable, and performing a stratified sampling of a subset of historical entities that have been classified as non-service-providing entities.

In other features, the machine learning model includes a random forest machine learning model. In other features, the method includes training a second machine learning model to identify consumers employed by entities according to predictor variables associated with the consumers. The identifying includes processing a plurality of consumers with the second machine learning model to identify the set of targets associated with the entity.

A computerized method of automatic distributed communication includes training a machine learning model with historical feature vector inputs to generate a selection score output. The historical feature vector inputs include historical profile data structures specific to multiple historical entities. The method includes obtaining a set of entities, and for each entity in the set of entities obtaining at least one of structured census data associated with the entity from a structured census database, and structured lifestyle data associated with the entity from a structured lifestyle database, generating a feature vector input according to the obtained at least one of the structured census data and the structured lifestyle data, and processing, by the machine learning model, the feature vector input to generate the selection score output. The selection score output is indicative of a likelihood that the entity will select a service provided by an employer of the entity. The method includes selectively including the entity in a subset of entities based on a comparison of the selection score output to a threshold value, and for each entity in the subset of entities, automatically distributing structured campaign data to the entity.

In other features, the training includes removing historical profile data structures that are specific to historical entities having an age greater than a maximum age threshold value, separating the historical profile data structures into a married dataset of the historical entities having a married status and a single dataset of the historical entities having a single status, and generating the historical feature vector inputs using the married dataset. In other features, the method includes, for each entity in the set of entities, determining whether the entity is an existing plan member, and in response to the entity being an existing plan member, obtaining a member relationship code associated with the entity, and identifying a spouse of the entity according to the member relationship code.

In other features, the generating includes generating the feature vector input according to the identified spouse of the entity, and the selection score output is indicative of a likelihood that the entity will select a service provided by an employer of the entity instead of selecting a service provided by an employer of the identified spouse of the entity. In other features, the training includes preprocessing the historical profile data structures, and the preprocessing includes identifying a variance value for each variable in the historical profile data structures, and removing each variable having an identified variance value below a target variance threshold. In other features, the preprocessing includes determining a weight of evidence (WOE) value for each variable in the historical profile data structures, and grouping the variables according to the determined WOE values, to create dummy variables for training the machine learning model.

A computerized method of automatically generating a likelihood output includes training a first machine learning model with historical feature vector inputs to generate a segment output. The historical feature vector inputs include historical employment data structures specific to multiple historical entities, the historical employment data structures defining multiple employer segments. The method includes training a second machine learning model with the historical feature vector inputs to generate an employment likelihood output, obtaining a set of entities. For each entity in the set of entities, the method includes obtaining at least one of structured census data associated with the entity from a structured census database, and structured lifestyle data associated with the entity from a structured lifestyle database, generating a feature vector input according to the obtained at least one of the structured census data and the structured lifestyle data, and processing, by the first machine learning model, the feature vector input to generate the segment output. The segment output is indicative of one of the multiple employer segments that has a highest likelihood of association with the entity. The method includes, for each entity in the set of entities, obtaining a set of employer entries from an employer segment database, according to the segment output, processing, by the second machine learning model, the feature vector input and the set of employer entries to generate the employment likelihood output. The employment likelihood output is indicative of one of the set of employer entries that has a highest likelihood of association with the entity, and transforming a user interface based on the employment likelihood output, to display the employment likelihood output.

In other features, the multiple employer segments include at least six employer segments, and each employer entry belongs to only one of the multiple employer segments. In other features, at least one of the first machine learning model and the second machine learning model includes a binary logistic regression model. In other features, the training the second machine learning model includes preprocessing the historical employment data structures, and the preprocessing includes partitioning structured employer data by a location of each employer entry in the structured employer data, obtaining a number of employees of each employer entry in the structured employment data, and removing each employer entry having a number of employees below an employee count threshold. In other features, the feature vector input includes a household income level associated with the entity and one or more drive times from a household location of the entity to one or more locations of one or more of the employer entries.

A computerized method of automatic distributed communication includes training a first machine learning model with historical feature vector inputs to generate a title score output. The historical feature vector inputs include historical profile data structures specific to multiple historical entities, and the historical profile data structures include structured title data and structured response data. The method includes training a second machine learning model with historical feature vector inputs to generate a background score output. The historical profile data structures include structured background data. The method includes obtaining a set of entities, and for each entity in the set of entities, obtaining structured title data associated with the entity from a structured title database, generating a title feature vector input according to the obtained structured title data, and processing, by the first machine learning model, the title feature vector input to generate the title score output. The title score output is indicative of a likelihood that the entity is a decision entity according to the structured title data associated with the entity. For each entity, the method includes obtaining structured background data associated with the entity from a structured background database, generating a background feature vector input according to the obtained structured background data, and processing, by the second machine learning model, the background feature vector input to generate the background score output. The background score output is indicative of a likelihood that the entity is a decision entity according to the structured background data associated with the entity. For each entity, the method includes combining the generated background score output and the generated title score output to determine a decision score output, and selectively including the entity in a subset of entities based on a comparison of the decision score output to a threshold value. For each entity in the subset of entities, the method includes automatically distributing structured campaign data to the entity.

In other features, the training of the first machine learning model includes classifying each one of the multiple historical entities as a decision entity or a non-decision entity according to the structured response data associated with the historical entity, and training the first machine learning model using the classifications for supervised learning. In other features, the training of the second machine learning model includes training the second machine learning model using the classifications for supervised learning.

In other features, the structured title data includes a job title matrix, and the training of the first machine learning model includes duplicating at least a portion of classified decision entity records in training data for the first machine learning model, down-sampling at least a portion of classified non-decision maker records in the training data for the first machine learning model, training a variable selection algorithm on the job title matrix to determine multiple significant keywords, selecting a specified number of highest scoring ones of the determined multiple significant keywords, and training a multinomial naive Bayes algorithm on a term frequency matrix of the selected specified number of keywords.

In other features, the structured background data includes a term frequency matrix, and the training of the second machine learning model includes duplicating at least a portion of classified decision entity records in training data for the second machine learning model, down-sampling at least a portion of classified non-decision maker records in the training data for the second machine learning model, and inputting the term frequency matrix and the structured background data into a binary classification algorithm.

In other features, the method includes transforming a user interface to display each entity in the subset of entities. In other features, the first machine learning model includes at least one of a variable selection machine learning algorithm and a binary classification machine learning algorithm. In other features, the second machine learning model includes a binary classification machine learning algorithm.

A computerized method of automatic distributed communication includes training a machine learning model with historical feature vector inputs to generate a decision score output. The historical feature vector inputs include historical profile data structures specific to multiple historical entities and the historical profile data structures include structured survey data, structured census data and structured lifestyle data. The method includes obtaining a set of entities, and for each entity in the set of entities, obtaining at least one of structured census data associated with the entity from a structured census database, and structured lifestyle data associated with the entity from a structured lifestyle database, generating a feature vector input according to the obtained at least one of the structured census data and the structured lifestyle data, and processing, by the machine learning model, the feature vector input to generate the decision score output. The decision score output is indicative of a likelihood that the entity is a decision entity in a household group that includes the entity. For each entity, the method includes selectively including the entity in a subset of entities based on a comparison of the decision score output to a threshold value. For each entity in the subset of entities, the method includes automatically distributing structured campaign data to the entity.

In other features, the distributing includes, in response to the structured campaign data including retention campaign data, comparing the decision score output of the entity to a decision score output of a spouse entry associated with the entity, automatically distributing the retention campaign data to the entity in response to the entity having a higher decision score output than the spouse entry associated with the entity, and automatically distributing the retention campaign data to the spouse entry associated with the entity in response to the entity having a lower decision score output than the spouse entry associated with the entity.

In other features, the distributing includes, in response to the structured campaign data including acquisition campaign data, identifying at least one household adult entry associated with a household group of the entity, and automatically distributing the acquisition campaign data to each household adult entry having a decision score output above the threshold value. In other features, the training the machine learning model includes preprocessing the historical profile data structures, and the preprocessing includes at least one of oversampling and undersampling a portion of the structured survey data to adjust a ratio of decision entities and non-decision entities in the structured survey data, performing a bivariate analysis to determine an association between a dependent variable and one or more independent variables of the historical profile data structures, and grouping variables of the historical profile data structures according to determined weight of evidence (WOE) values associated with the variables, to create binary dummy variables for categorical and numerical inputs to the machine learning model.

A computer system includes memory hardware configured to store a machine learning model, historical feature vector inputs, and computer-executable instructions. The historical feature vector inputs include historical profile data structures specific to multiple historical entities, and the historical profile data structures include structured title data, structured response data, and structured background data. The system also includes processor hardware configured to execute the instructions. The instructions include training a first machine learning model with the historical feature vector inputs to generate a title score output, training a second machine learning model with historical feature vector inputs to generate a background score output, obtaining a set of entities, and for each entity in the set of entities, obtaining structured title data associated with the entity from a structured title database, generating a title feature vector input according to the obtained structured title data, and processing, by the first machine learning model, the title feature vector input to generate the title score output. The title score output is indicative of a likelihood that the entity is a decision entity according to the structured title data associated with the entity. For each entity, the instructions include obtaining structured background data associated with the entity from a structured background database, generating a background feature vector input according to the obtained structured background data, and processing, by the second machine learning model, the background feature vector input to generate the background score output. The background score output is indicative of a likelihood that the entity is a decision entity according to the structured background data associated with the entity. For each entity, the instructions include combining the generated background score output and the generated title score output to determine a decision score output, and selectively including the entity in a subset of entities based on a comparison of the decision score output to a threshold value. For each entity in the subset of entities, the instructions include automatically distributing structured campaign data to the entity.

In other features, the training of the first machine learning model includes classifying each one of the multiple historical entities as a decision entity or a non-decision entity according to the structured response data associated with the historical entity, and training the first machine learning model using the classifications for supervised learning. In other features, the training of the second machine learning model includes training the second machine learning model using the classifications for supervised learning.

In other features, the structured title data includes a job title matrix, and the training of the first machine learning model includes duplicating at least a portion of classified decision entity records in training data for the first machine learning model, down-sampling at least a portion of classified non-decision maker records in the training data for the first machine learning model, training a variable selection algorithm on the job title matrix to determine multiple significant keywords, selecting a specified number of highest scoring ones of the determined multiple significant keywords, and training a multinomial naive Bayes algorithm on a term frequency matrix of the selected specified number of keywords.

In other features, the structured background data includes a term frequency matrix, and the training of the second machine learning model includes duplicating at least a portion of classified decision entity records in training data for the second machine learning model, down-sampling at least a portion of classified non-decision maker records in the training data for the second machine learning model, and inputting the term frequency matrix and the structured background data into a binary classification algorithm.

In other features, the instructions further include transforming a user interface to display each entity in the subset of entities. In other features, the first machine learning model includes at least one of a variable selection machine learning algorithm and a binary classification machine learning algorithm. In other features, the second machine learning model includes a binary classification machine learning algorithm.

A computerized method of automatic distributed communication, the method includes training a first machine learning model with historical feature vector inputs to generate a likelihood output. The historical feature vector inputs include historical profile data structures specific to multiple historical entities, and the historical profile data structures include structured claim data and structured profile data. The method includes training a second machine learning model with historical feature vector inputs to generate a mean count output, obtaining a set of entities, and for each entity in the set of entities, obtaining structured claim data and structured profile data associated with the entity from a structured profile database, generating a likelihood feature vector input according to the obtained structured claim data and structured profile data, and processing, by the first machine learning model, the likelihood feature vector input to generate the likelihood output. The likelihood output is indicative of a likelihood that the entity will have an avoidable negative health event within a specified first time period. For each entry, the method includes selectively including the entity in a first subset of entities based on a comparison of the likelihood output to a likelihood threshold value, generating a mean count feature vector input according to the obtained structured claim data and structured profile data, and processing, by the second machine learning model, the mean count feature vector input to generate the mean count output. The mean count output is indicative of an expected number of avoidable negative health events that the entity will have within a specified second time period. For each entity, the method includes selectively including the entity in a second subset of entities based on a comparison of the mean count output to a mean count threshold value. The method includes automatically distributing structured campaign data to at least one of the first subset of entities and the second subset of entities.

In other features, the obtaining structured profile data includes obtaining structured member demographic data, structured member risk data, and at least one of structured external vendor data, structured external hobby data and structured external demographic data, the obtaining structured claim data includes obtaining structured transactional claim data, and the method includes aggregating the structured transactional claim data at an individual entity level. For each entity in the set of entities, the method includes merging the structured profile data associated with the entity with the aggregated transactional claim data associated with the entity, according to an individual key associated with the entity.

In other features, the method includes performing feature standardization on the merged structured profile data and aggregated transactional claim data, performing feature engineering on the merged structured profile data and aggregated transactional claim data, and performing categorical data handling on the merged structured profile data and aggregated transactional claim data. In other features, the method includes obtaining at least one mean cost value from a structured event cost database, the at least one mean cost value indicative of an expected cost per negative health event, and calculating, for each entity in the second subset of entities, an expected heath cost score according to the mean count output for the entity and the obtained at least one mean cost value.

In other features, the method includes calculating an overall cost value for a health insurance provider, according to the expected health cost score for each entity in the second subset of entities. In other features, the specified first time period is different than the specified second time period. In other features, the specified first time period is three months and the specified second time period is one year.

In other features, the training the first machine learning model includes preprocessing the historical profile data structures, and the preprocessing includes standardizing numeric values in the historical profile data structures, encoding categorical variables in the historical profile data structures, and imputing missing values in the historical profile data structures. In other features, the training the first machine learning model includes building the first machine learning model using a gradient boosting decision tree or a regression algorithm with a Poisson loss function.

A computerized method of automatic distributed communication, the method includes training a machine learning model with historical feature vector inputs to generate a retirement score output. The historical feature vector inputs include historical profile data structures specific to multiple historical entities within a specified age range, the historical profile data structures including at least one of historical structured lifestyle data, historical structured census data and historical structured employment data. The method includes obtaining a set of entities, and for each entity in the set of entities, obtaining at least one of structured census data associated with the entity from a structured census database, structured lifestyle data associated with the entity from a structured lifestyle database, and structured employment data associated with the entity from a structured employment database, generating a feature vector input according to the obtained at least one of the structured census data, the structured lifestyle data, and the structured employment data, and processing, by the machine learning model, the feature vector input to generate the retirement score output. The retirement score output is indicative of a predicted time period until the entity transitions to a retirement status. For each entity, the method includes assigning the entity to one of multiple bins according to the retirement score output. For one or more of the multiple bins, the method includes automatically distributing structured campaign data associated with the bin to each entity assigned to the bin.

In other features, the method includes obtaining an expected retirement date value for each entity in the set of entities, comparing, for each entity, the expected retirement date value for the entity with the retirement score output to generate an on-time retirement likelihood score, generating a rank order list indicating the entities that have the highest on-time retirement likelihood scores, and transforming a user interface to display the generated rank order list.

In other features, the training includes preprocessing the historical profile data structures, and the preprocessing includes identifying each variable in the historical profile data structures that is missing a value for at least one of the multiple historical entities, removing each variable in the historical profile data structures that is missing a value for a number of the multiple historical entities that is greater than a specified minimum entity threshold, and for each of the multiple historical entities that is missing a value for one of the identified variables, imputing an assigned value to the identified variable.

In other features, imputing the assigned value includes, in response to the identified variable being a categorical variable, determining a mode of the identified variable across all of the multiple historical entities that have a value for the identified variable, assigning the mode to each of the multiple historical entities that is missing a value for the identified variable, and in response to the identified variable being a numerical variable that is left skewed or right skewed across all of the multiple historical entities that have a value for the identified variable, determining a median of the identified variable across all of the multiple historical entities that have a value for the identified variable, and assigning the median to each of the multiple historical entities that is missing a value for the identified variable.

In other features, the preprocessing includes determining outlier values in the historical profile data structures according to one or more outlier thresholds, removing the determined outlier values from training data for the machine learning model, and assigning categorical values and numerical values in the historical profile data structures to bins to reduce complexity of input to the machine learning model. In other features, the machine learning model includes a random forest algorithm model.

In other features, the training includes randomly selecting a sample with replacement from a training dataset including N observations and M features. The training dataset includes at least a portion of the historical profile data structures. The method includes randomly selecting a subset of the M features, determining which feature of the randomly selected subset provides a best node split outcome from among the randomly selected subsets, and performing iterative node splitting using the determined feature to grow a tree of the random forest algorithm model to a maximum size. In other features, the method includes repeating the randomly selecting a subset of the M features, the determining, and the performing, until a number of generated trees is equal to a target value of trees, and aggregating predictions from each tree to generate the retirement score output of the random forest algorithm model.

A computerized method of automatic distributed communication, the method includes training a machine learning model with historical feature vector inputs to generate a customer segment likelihood output. The historical feature vector inputs include structured customer segment data and historical profile data structures specific to multiple historical entities, and the historical profile data structures include at least one of historical structured lifestyle data, historical structured census data, historical structured medical history data, and historical structured health plan data. The method includes obtaining at least one of historical structured lifestyle data, historical structured census data, historical structured medical history data, and historical structured health plan data, associated with an entity. The method includes obtaining a set of customer segments, obtaining a segment score data structure associated with the entity, the segment score data structure including multiple entries, each entry associated with a different one of the set of customer segments, and for each customer segment in the set of customer segments, generating a feature vector input according to the customer segment and the at least one of historical structured lifestyle data, historical structured census data, historical structured medical history data, and historical structured health plan data, and processing, by the machine learning model, the feature vector input to generate the customer segment likelihood output. The customer segment likelihood output is indicative of a likelihood that the entity belongs to the customer segment. For each customer segment, the method includes assigning the customer segment likelihood output to one of the multiple entries in the segment score data structure that corresponds to the customer segment. The method includes determining which one of the customer segments has a highest customer segment likelihood in the segment score data structure, obtaining structured campaign data associated with the determined customer segment, and automatically distributing the obtained structured campaign data to the entity.

In other features, the set of customer segments includes a predefined set of at least eight customer segments. In other features, the machine learning model includes a multi-class look-alike classification model.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIGS. 3A and 3B are graphical representations of example recurrent neural networks for generating machine learning models for health plan management.

In the drawings, reference numbers may be reused to identify similar and/or identical elements.

DETAILED DESCRIPTION

The present disclosure describes model-based systems and methods for managing aspects related to employer health plans, health insurance offerings, and preventative health care. Historical data may be used to generate, train, and validate various prediction models. These models are then used to provide predictions regarding employee health plan offerings and choices, employee workplace locations, individual and business health plan decision makers, a likelihood of avoidable ER visits, employee retirement age and Medicare enrollment, and customer segmentation. The predictions may be provided in the form of various easy-to-understand graphical representations (for example, graphs, charts, tables, and reports), as well as optionally in the form of downloadable raw data for use or rendering by the client. For example, the raw data may be provided in the form of XML (extensible markup language), CSV (comma-separated value), or JSON (JavaScript Object Notation).

Machine learning is a field of data analysis that combines statistical methods and computer science to construct sophisticated algorithms for exploiting trends and behaviors from large data sets. The algorithms are sets of rules for identifying important drivers of selected variables, their transformations (for example, taking a metric and converting it to a ratio), capturing non-linear relationships, and stress-testing discovered links on new data.

Pattern recognition encompasses characterization and recognition of systematic patterns over time. In one example, such patterns are classified into (1) trend/drift (for example, upward, downward, or flat), (2) seasonality, (3) cyclicality (for example, plan changes at different time periods), and (4) noise (that is, small fluctuations not associated with any of the model inputs).

Regression in this context establishes a quantifiable link between dependent variables and their drivers (for example, prior trends, customer demographics, and plan member information), by making the difference between the forecast and actuals as small as possible. All three techniques may establish weights and directions between dependent and independent variables by allowing the algorithms to "learn" from historical data. Once appropriate rules are established, they are applied in the form of a model to make predictions. The model estimates may be further refined by accounting for anticipated events with details provided by pipeline data.

Thus, the model may use customer-specific past performance and key data to forecast future trends through pattern recognition in the historical data by using machine learning. The model may be adapted for known plan changes, and may take into account known or anticipated variables about the customers. The model forecasts may include estimates generated based on customer-specific datasets from multiple sources.

ML System for Prediction Output Generation

Figure 1:
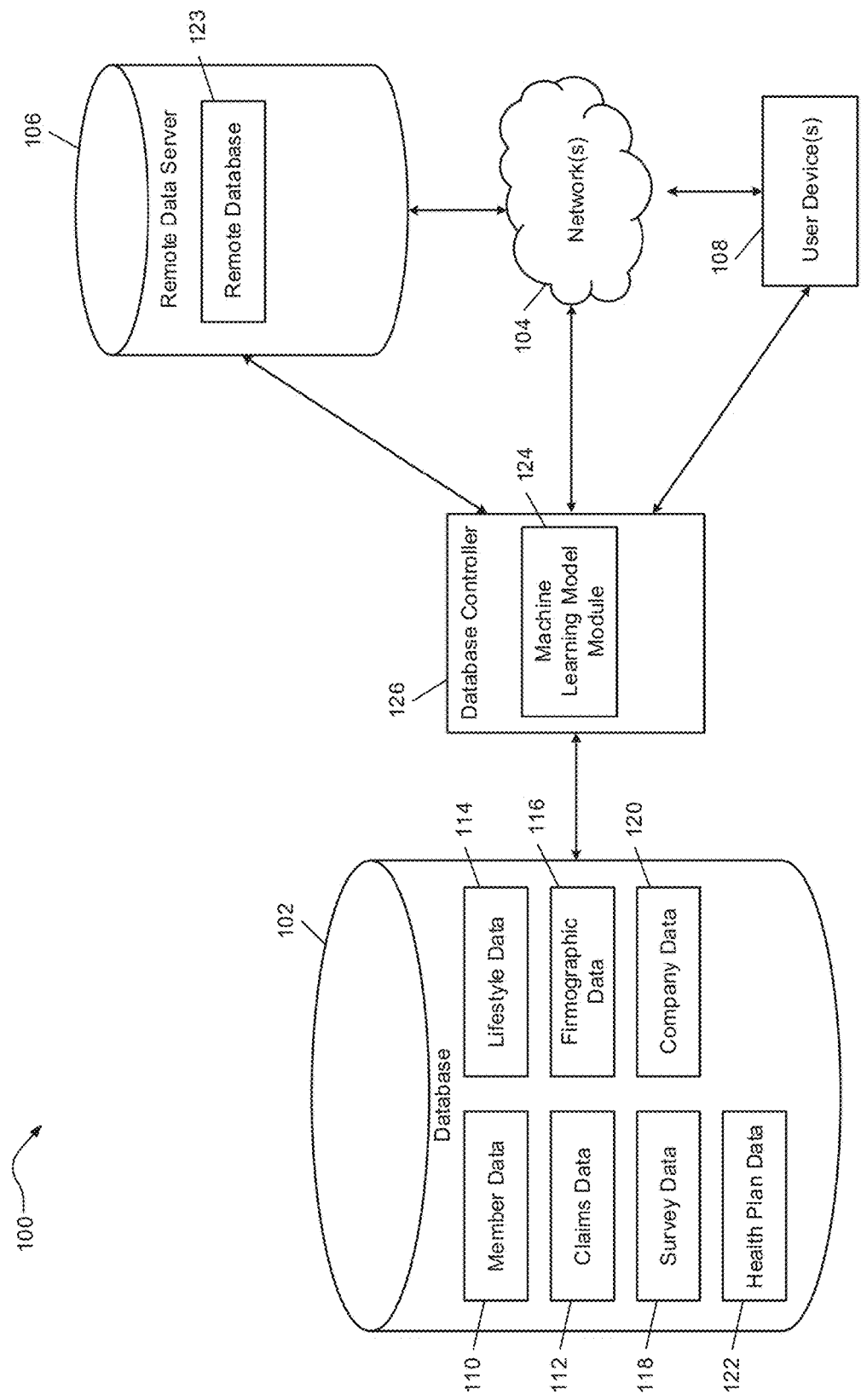
FIG. 1 is a functional block diagram of an example system for automated database element processing and prediction output generation.

FIG. 1 is a block diagram of an example system 100 for implementing machine learning models for automated database element processing and prediction output generation, including a database 102. While the database 102 is generally described as being deployed in a health plan administrator computer system (for example, a company that provides health insurance plans for individuals or for other companies to offer to their employees), the database 102 and/or other components of the system 100 may otherwise be deployed (for example, as a standalone computer setup, etc.). The database 102 may include any suitable data store, and may include one or more of a server, a desktop computer, etc.

As shown in FIG. 1, the database 102 has multiple data modules which may be stored as data structures, including member data 110, claims data 112, lifestyle data 114, firmographic data 116, survey data 118, company data 120 and health plan data 122. The member data 110, claims data 112, lifestyle data 114, firmographic data 116, survey data 118, company data 120, and health plan data 122, may be located in different physical memories within the database 102, such as different random access memory (RAM), read-only memory (ROM), a non-volatile hard disk or flash memory. In some implementations, one or more of the member data 110, claims data 112, lifestyle data 114, firmographic data 116, survey data 118, company data 120, and health plan data 122, may be located in the same memory (for example, in different address ranges of the same memory).

A machine learning model module 124 may be configured to access one or more of the member data 110, claims data 112, lifestyle data 114, firmographic data 116, survey data 118, company data 120, and health plan data 122, in order to generate one or more machine learning models. For example, the machine learning model module 124 may use any suitable machine learning techniques, including those described further herein, to incorporate selected sub-sets of the member data 110, claims data 112, lifestyle data 114, firmographic data 116, survey data 118, company data 120, and health plan data 122 (and/or any other suitable data), to generate predictive models for variables of interest related to health plan management.

For example, a health plan administrator may access the machine learning model module 124 of a database controller 126 via the user device 108, in order to specify a desired type of machine learning model to be generated, and which sub-sets of data to include from the member data 110, claims data 112, lifestyle data 114, and firmographic data 116, survey data 118, company data 120, and health plan data 122 (and/or any other suitable data) to develop the model. The user device 108 may include any suitable device for requesting access to the computer system including the database 102, such as a desktop computer, a laptop computer, a tablet, or a smartphone. The user device 108 may access the database 102 directly, or may access the database 102 through one or more networks 104.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet.

The system 100 may include a remote data server 106 including a remote database 123 for storing additional data. For example, the remote database 123 may store information that is duplicative of the member data 110, claims data 112, lifestyle data 114, firmographic data 116, survey data 118, company data 120, and health plan data 122. The remote database 123 may store information that is in addition to or supplemental to the member data 110, claims data 112, lifestyle data 114, firmographic data 116, survey data 118, company data 120, and health plan data 122, and/or other types of information that are not stored in the database 102. The database 102 may be in communication with the remote data server 106, either directly or through the network(s) 104, to obtain more data for the machine learning model module 124 to develop machine learning models.

Figure 2:
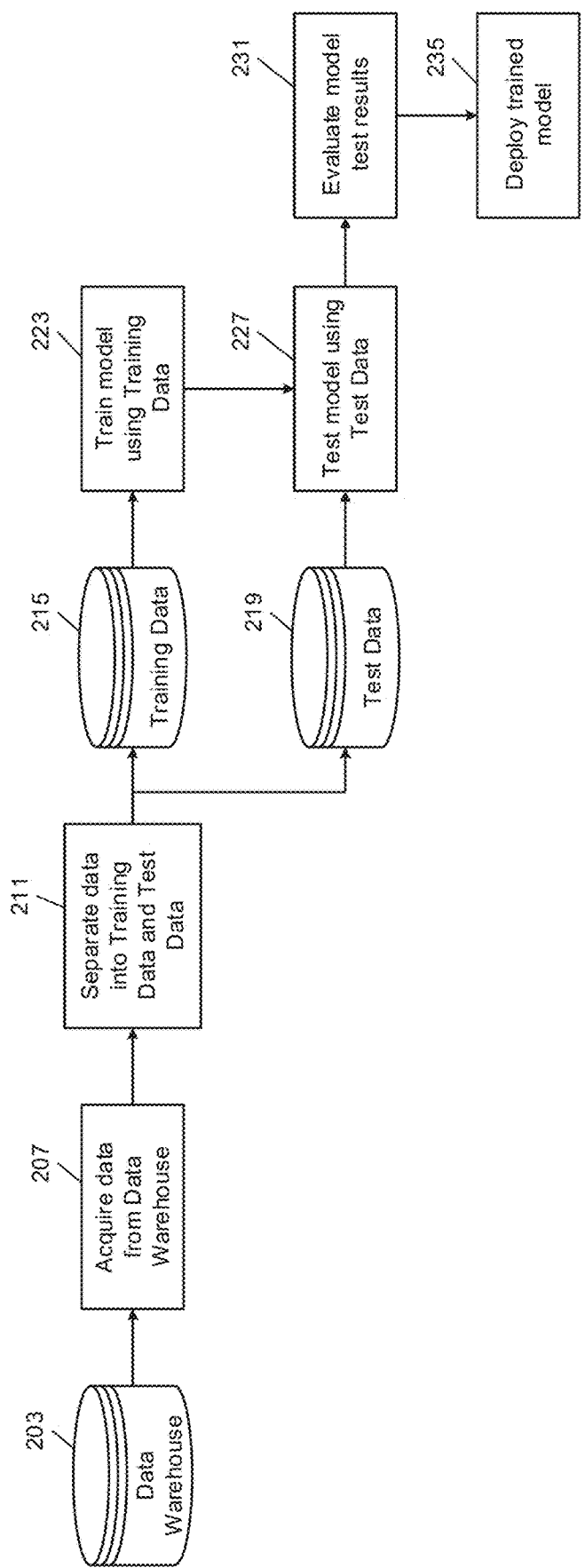
FIG. 2 is a flowchart depicting an example method of generating a machine learning model for health plan management.

FIG. 2 illustrates an example process for generating a machine learning model (for example, using the machine learning model module 124 of FIG. 1). At 207, control obtains data from a data warehouse 203. The data warehouse 203 may include any suitable data for developing the machine learning model. For example, data from the data warehouse may be used to generate historical feature vector inputs for training the machine learning model. The historical feature vector inputs may include, for example, one or more of the member data 110, claims data 112, lifestyle data 114, firmographic data 116, survey data 118, company data 120, and health plan data 122, of the database 102 in FIG. 1.

At 211, control separates the data obtained from the data warehouse 203 into training data 215 and test data 219. The training data 215 is used to train the model at 223, and the test data 219 is used to test the model at 227. Typically, the set of training data 215 is selected to be larger than the set of test data 219, depending on the desired model development parameters. For example, the training data 215 may include about seventy percent of the data acquired from the data warehouse 203, about eighty percent of the data, about ninety percent, etc. The remaining thirty percent, twenty percent, or ten percent, is then used as the test data 219.

Separating a portion of the acquired data as test data 219 allows for testing of the trained model against actual historical output data, to facilitate more accurate training and development of the model at 223 and 227. The model may be trained at 223 using any suitable machine learning model techniques, including those described herein, such as random forest, logistic regression, and neural networks.

At 231, control evaluates the model test results. For example, the trained model may be tested at 227 using the test data 219, and the results of the output data from the tested model may be compared to actual historical outputs of the test data 219, to determine a level of accuracy. The model results may be evaluated using any suitable machine learning model analysis, such as cumulative gain and lift charts. Lift is a measure of the effectiveness of a predictive model calculated as the ratio between the results obtained with and without the predictive model (for example, by comparing the tested model outputs at 227 to the actual outputs of the test data 219). Cumulative gains and lift charts provide visual aids for measuring model performance. Both charts include a lift curve and a baseline, where a greater area between the lift curve and the base line indicates a stronger model.

Cumulative gains and lift charts are graphical representations of the advantage of using a predictive model to, for example, choose which prospective health plan customers to contact. The lift chart shows how much more likely the model is at predicting respondents than contacting a random sample of customers. For example, a chart may indicate for one specific model that contacting only 10% of customers based on the predictive model (such as by contacting the highest rank-ordered individuals according to the predictive model output), will produce a result of receiving three times as many respondents as not using any model and instead targeting a random sample.

The value of a predictive model may be assessed by using the model to score a set of customers and then contacting them in the scored order. The actual response rates are recorded for each cutoff point, such as the first 10% contacted, the first 20% contacted, etc. Then cumulative gains and lift charts are created using the actual response rates to determine how much the predictive model helped in generating actual responses. The information can be used to determine whether the particular model should be used in the future to increase response rates above random sampling.

After evaluating the model test results at 231, the model may be deployed at 235 if the model test results are satisfactory. Deploying the model may include using the model to make predictions for a large-scale input dataset with unknown outputs, and using the model to initiate a targeted health plan campaign for individuals identified by the model. If the evaluation of the model test results at 231 is unsatisfactory, the model may be developed further using different parameters, using different modeling techniques, etc.

FIGS. 3A and 3B show an example of a recurrent neural network used to generate models such as those described above with reference to FIG. 2, using machine learning techniques. Machine learning is a method used to devise complex models and algorithms that lend themselves to prediction (for example, health plan customer predictions). The models generated using machine learning, such as those described above with reference to FIG. 2, can produce reliable, repeatable decisions and results, and uncover hidden insights through learning from historical relationships and trends in the data.

The purpose of using the recurrent neural-network-based model, and training the model using machine learning as described above with reference to FIG. 2, may be to directly predict dependent variables without casting relationships between the variables into mathematical form. The neural network model includes a large number of virtual neurons operating in parallel and arranged in layers. The first layer is the input layer and receives raw input data. Each successive layer modifies outputs from a preceding layer and sends them to a next layer. The last layer is the output layer and produces output of the system.

FIG. 3A shows a fully connected neural network, where each neuron in a given layer is connected to each neuron in a next layer. In the input layer, each input node is associated with a numerical value, which can be any real number. In each layer, each connection that departs from an input node has a weight associated with it, which can also be any real number (see FIG. 3B). In the input layer, the number of neurons equals number of features (columns) in a dataset. The output layer may have multiple continuous outputs.

The layers between the input and output layers are hidden layers. The number of hidden layers can be one or more (one hidden layer may be sufficient for most applications). A neural network with no hidden layers can represent linear separable functions or decisions. A neural network with one hidden layer can perform continuous mapping from one finite space to another. A neural network with two hidden layers can approximate any smooth mapping to any accuracy.

The number of neurons can be optimized. At the beginning of training, a network configuration is more likely to have excess nodes. Some of the nodes may be removed from the network during training that would not noticeably affect network performance. For example, nodes with weights approaching zero after training can be removed (this process is called pruning). The number of neurons can cause under-fitting (inability to adequately capture signals in dataset) or over-fitting (insufficient information to train all neurons; network performs well on training dataset but not on test dataset).

Various methods and criteria can be used to measure performance of a neural network model (such as for the model test result evaluation at 231 in FIG. 2). For example, root mean squared error (RMSE) measures the average distance between observed values and model predictions. Coefficient of Determination ($R^2$) measures correlation (not accuracy) between observed and predicted outcomes (for example, between trained model outputs and actual outputs of the test data 219, etc.). This method may not be reliable if the data has a large variance. Other performance measures include irreducible noise, model bias, and model variance. A high model bias for a model indicates that the model is not able to capture true relationship between predictors and the outcome. Model variance may indicate whether a model is not stable (a slight perturbation in the data will significantly change the model fit).

Employer Health Plan Prediction Model

Figure 4:
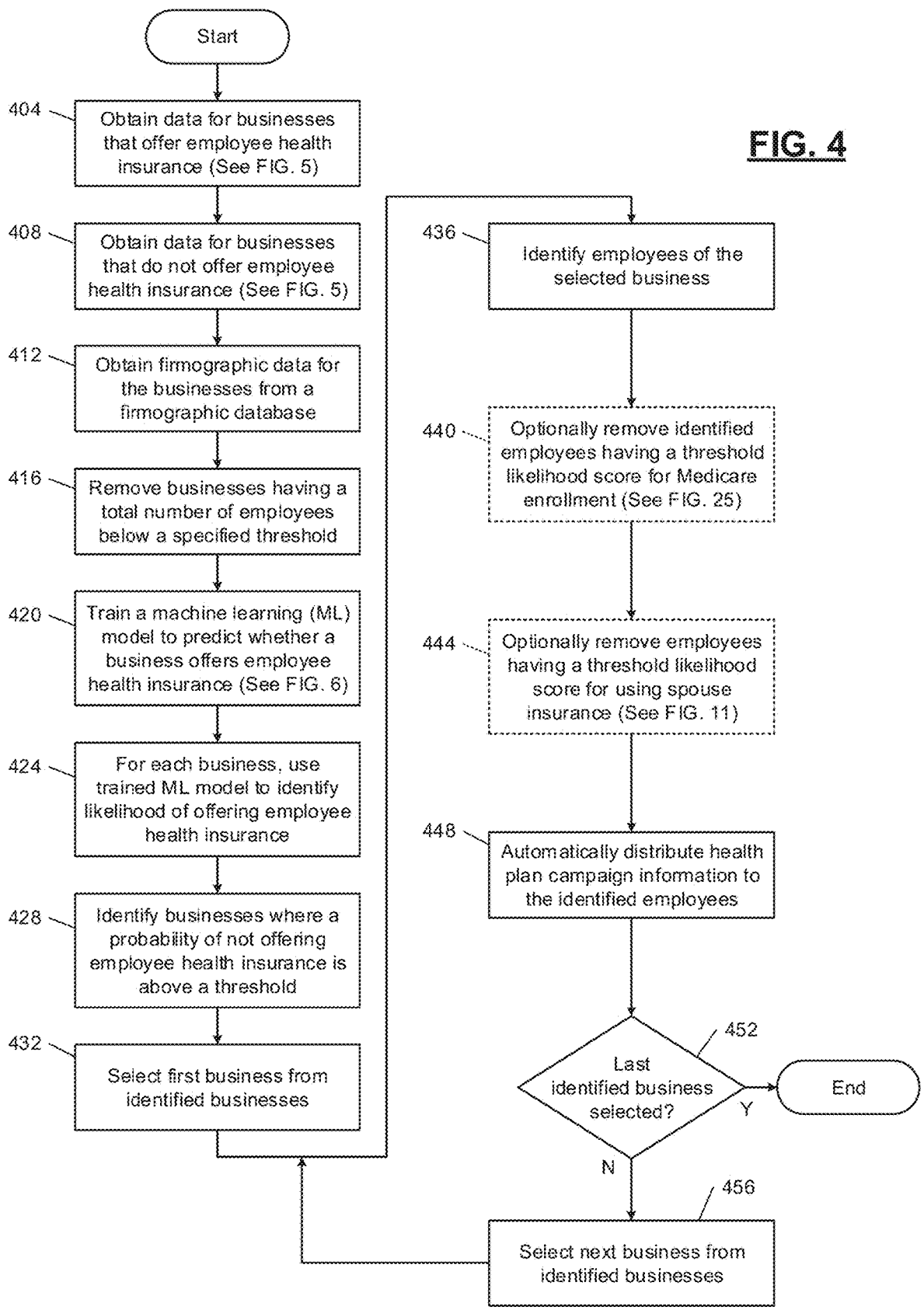
FIG. 4 is a flowchart depicting an example method of implementing a machine learning model for generation of an employer sponsored health plan prediction output.
Figure 5:
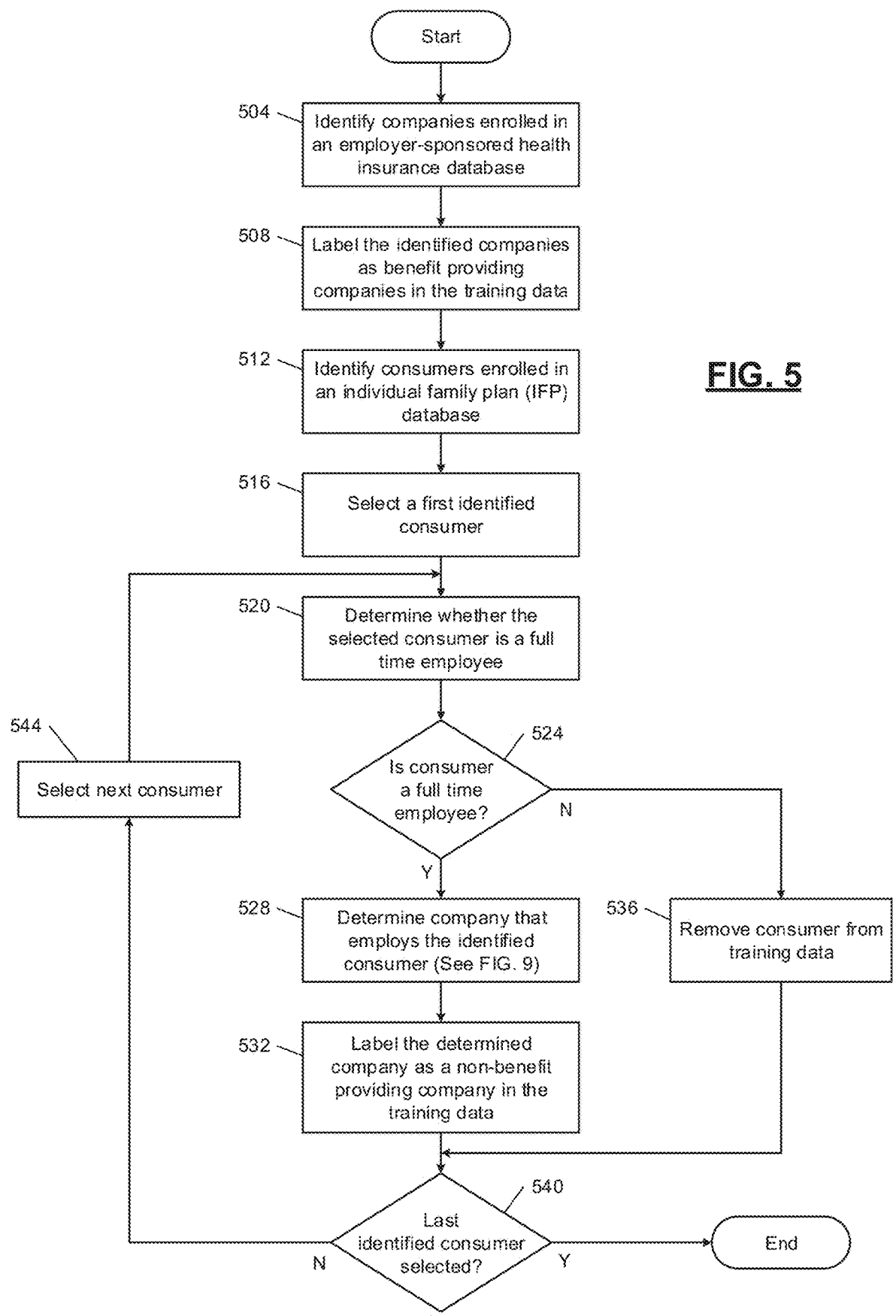
FIG. 5 is a flowchart depicting an example method of generating training data for the machine learning model of FIG. 4.

FIG. 4 illustrates an example process for generating a machine learning model for predicting the likelihood of an employer offering a sponsored health plan to its employees. At 404, control beings by obtaining data (such as the member data 110 in the database 102 of FIG. 1) for businesses that offer employee health insurance. This is illustrated in FIG. 5 and described further below. For example, a health plan administrator may access an existing book of business, such a through a Salesforce database of existing employer health plan customers, to identify businesses that are known to offer employer-sponsored health plans to their employees (for example, health plans where the employer covers a portion or all of an employee's premium cost, or health plans that offer discounted premiums or other health benefits to employees though their employer).

At 408, control obtains data for businesses that do not offer employer-sponsored health plans to their employees. This is also illustrated in FIG. 5 and described further below. For example, a health plan administrator may access a database of Affordable Care Act enrollees to identify individuals who are not currently receiving health insurance through their employers, or may access an existing book of business of individual family plan (IFP) enrollees who are not currently receiving health insurance through their employers.

Once individuals are identified who are not receiving health insurance through their employers, the control may determine a location of employment for each identified individual by pulling information from an existing database of employee-employer pairs (for example, the ExecuReach Grade 0 database), in order to create a sample of businesses that presumably do not offer health insurance to their employees.

Control proceeds to obtain structured firmographic data for the businesses from a structured firmographic database (such as the firmographic data 116 of the database 102 in FIG. 1), at 412. The obtained firmographic data may include multiple variables identifying different characteristics of each business, such as size, revenue, location, earnings, financial stability, etc. For example, in some implementations, a Dun & Bradstreet file may provide data for up to 1500 variables for each business. The corresponding firmographic data may be combined with the identified employer-sponsored health insurance plan businesses and non-employer-sponsored health insurance plan businesses, to develop the model.

At 416, businesses having an employee size below a specified threshold may be removed, such as less than ten employees, less than twenty employees, less than fifty employees, etc. This may reduce any bias that could otherwise be caused by smaller sized companies that typically do not offer health insurance to their employees. In some implementations, part-time employees or companies offering primarily part-time work may be removed from the data, to reduce bias that may be caused by part-time workers typically not receiving employer insurance.

Figure 6:
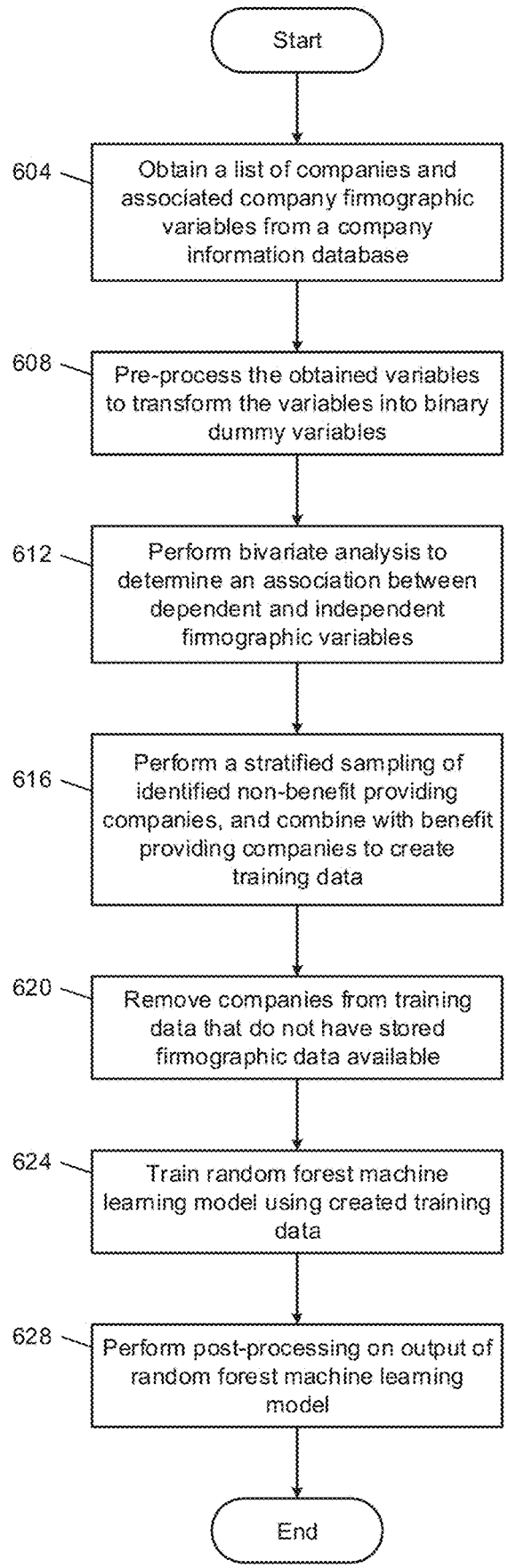
FIG. 6 is a flowchart depicting an example method of training the machine learning model of FIG. 4.

Control proceeds to train the machine learning model at 420, to predict whether a business offers employee health insurance. This is illustrated in FIG. 6, and described further below. For example, an event rate of businesses that do not offer employer-sponsored health insurance may be assumed to be about five percent, about ten percent, about fifteen percent, etc. A corresponding event rate of businesses that offer employer-sponsored health insurance may be assumed to be about ninety five percent, about ninety percent, about eighty five percent, etc. For modeling, a dependent variable of one may be selected for businesses that do not offer health insurance, and a dependent variable of zero may be selected for businesses that offer health insurance.

During training of the model at 420, any suitable machine learning technique(s) may be used to classify the firmographic data (for example, historical structured firmographic data) corresponding to the offering and non-offering businesses, to process the data, including random forest models and logistic regression models. Probability estimation may be used to determine scores for each of the records that describe whether a business does or does not offer an employer-sponsored health insurance plan.

In various implementations, the machine learning model may be trained with historical feature vector inputs, and the historical feature vector inputs may include historical service data structures specific to multiple historical entities (such as tables that indicate whether existing businesses offer an employer-sponsored health insurance service or not).

Once the model is trained at 420, control proceeds to 424 to use the trained model on multiple target businesses, to identify the likelihood of the target business to offer insurance to its employees (such as by generating a service score output indicative of a likelihood that the business entity is a service-providing entity that offers an employer-sponsored health insurance service to its employees). For example, firmographic data for a business with an unknown employee health plan status may be supplied to the trained model, to output a likelihood that the unknown business offers an employer-sponsored plan.

At 428, control identifies businesses where a probability of not offering employee health insurance is above a specified threshold (which may be classified as non-service-providing entities). For example, the specified threshold may be a twenty percent likelihood of not offering an employer-sponsored plan (which is greater than an estimated ten percent likelihood for a random sampling), a threshold of a fifty percent likelihood of not offering an employer-sponsored plan, a threshold of ninety percent, etc. In some implementations, the businesses may be rank-ordered according to their predicted likelihoods.

Control then selects a first business from the identified businesses at 432. For example, an administrator may select a business from a top decile of the rank-ordered businesses (such as the top ten percent of businesses most likely to not offer an employer-sponsored plan), from a second decile, a third decile, etc. The business may be selected for targeting employees with health plan campaign information.

At 436, control identifies employees of the selected business (for example, target employees associated with the business entity). For example, if a public list of employees that work for the selected business is known, the list may be used to automatically distribute health plan campaign information to the employees, at 448. A database that matches employee and employer pairs, such as the ExecuReach Grade 0 database, may be used to obtain the employee-employer relationship information. In other implementations, employers may be identified by modeling data of the employees themselves, including lifestyle data 114 from the database 102 of FIG. 1. An example model is described further in FIGS. 7-10 herein.

Figure 25:
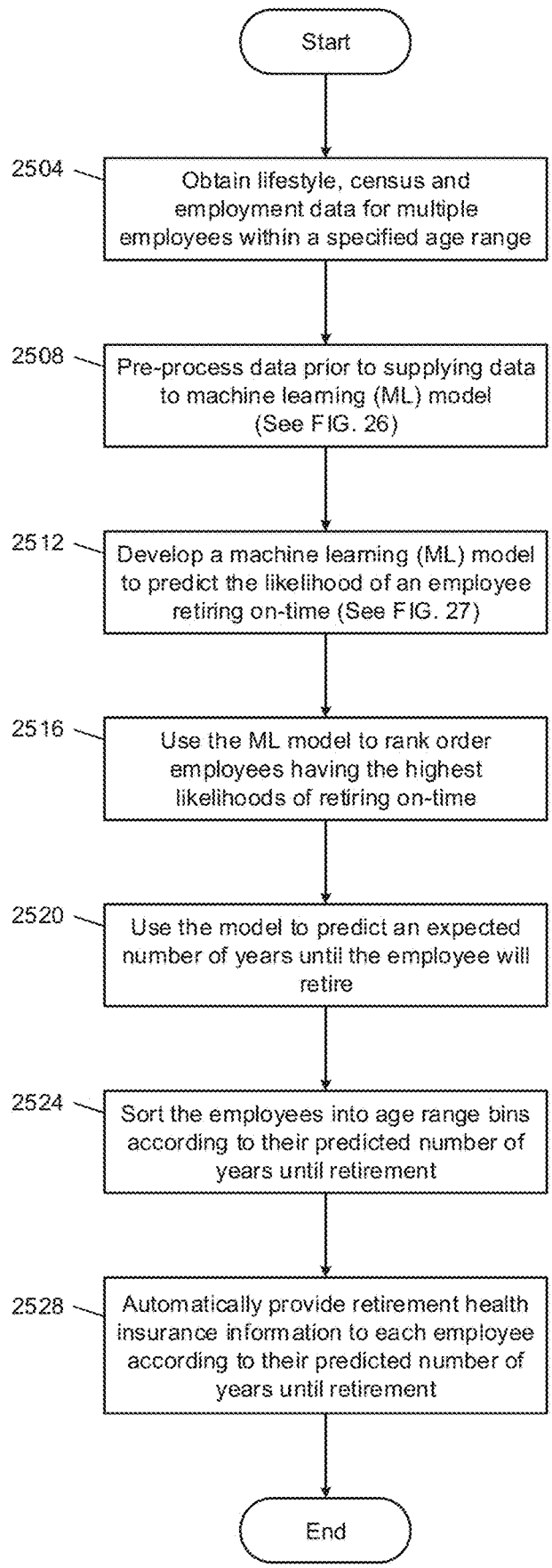
FIG. 25 is a flowchart depicting an example method of implementing a machine learning model for generation of a retirement prediction score for an employee.

Control may optionally remove identified employees having a threshold likelihood score for Medicare enrollment at 440. For example, employees that are identified as likely to enroll in Medicare may not purchase other insurance, even if the employee's current employer does not offer an employer-sponsored plan. An example model for predicting Medicare enrollment is illustrated in FIG. 25 and discussed further below.

Figure 21:
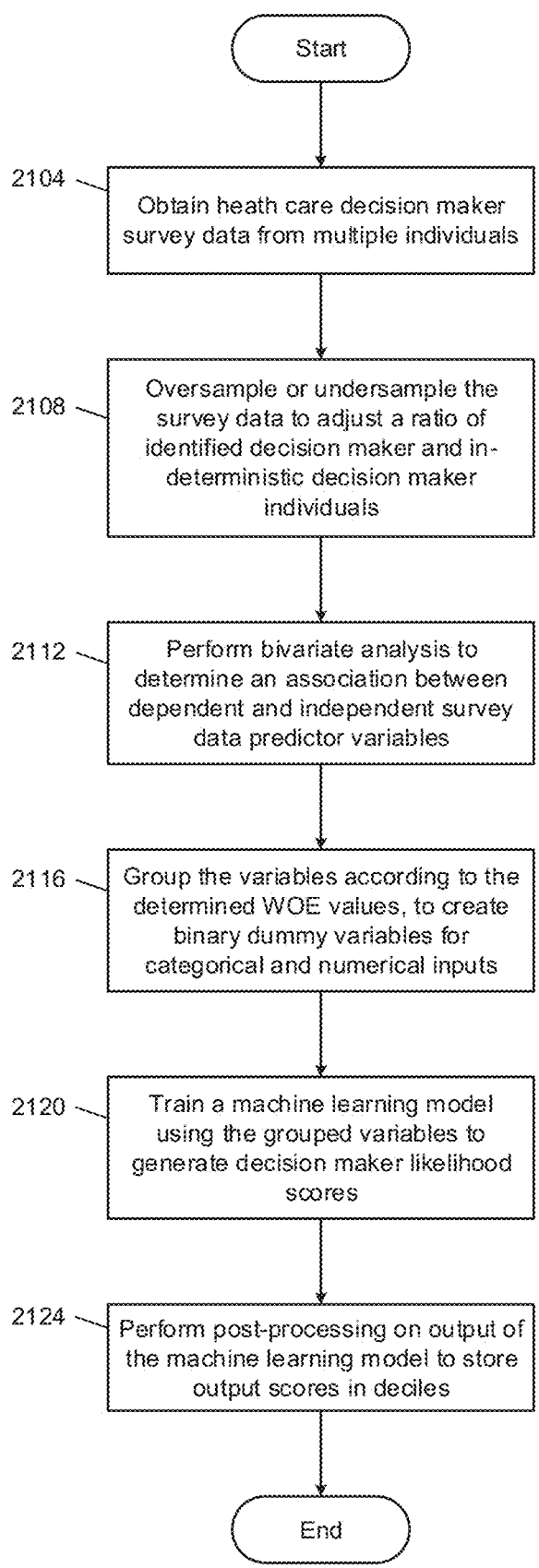
FIG. 21 is a flowchart depicting an example method of training the machine learning model of FIG. 20.

Control may optionally remove identified employees having a threshold likelihood score for using a spouse's insurance plan, at 444. For example, employees that are identified as likely to user their spouse's plan may not purchase insurance, even if the employee's current employer does not offer an employer-sponsored plan. An example model for predicting use of a spouse's insurance plan is illustrated in FIG. 21 and discussed further below.

Automatically distributing structured health plan campaign information at 448 may include any suitable automated process for generating emails, social media advertisements, digital advertisement purchases, entertainment content streaming advertisements, etc., that target the identified employees. Because the identified employees are known to have a higher likelihood of working for an employer that does not offer employee health insurance, the identified employees are expected to have a higher response rate for purchasing individual health insurance plans.

At 452, control determines whether the last identified business has been selected. If so, the process ends. If there are more identified businesses that still have not been selected (for example, there are more businesses in the top decile, etc.), control proceeds to select the next business at 456, and repeats identification of the employees of the next business at 436.

While developing the model, a system administrator may use any suitable techniques for understanding the available feature space and finding patterns by plotting, creating charts, using descriptive statistical techniques, etc. The data acquired may be a large sample, with more than 1500 variables is some cases. Preprocessing steps may be used to clean data prior to training the model or using the model, including column renaming, scaling numerical variables, encoding categorical variables, binning, creating dummies, dropping variables which are determined to not have sufficient significance, handling different data types, imputing values, creating training and test samples, etc.

Optimized machine learning modelling techniques may be used to choose the best models, and hyper-parameters may be tuned while considering impacts on performance, accuracy, bias and variance of the model, including evaluation by calculating and plotting a gains-lift chart. Both local and cloud platforms may be used per data size and business requirements. Once the model is ready, the model may be used to score for different campaigns, including both acquisition and retention campaigns.

In some implementations, the target audience of the model is individuals who are not being offered health insurance from their employer. Once the audience is identified correctly, a campaign population may be cut down to about 1.2 million individuals, versus a general population of about three hundred million. The model framework facilitates a marketing strategy to suppress the list so that only the best-suited audience for individual plans may be targeted with health plan campaign information, effectively cutting the cost and influencing the correct targets with the campaign.

FIG. 5 is a flowchart depicting an example method of generating training data for the machine learning model of FIG. 4. At 504, control begins by identifying companies enrolled in an employer-sponsored health insurance database, such as the database 102. Control then labels the identified companies as benefit providing companies in the training data, at 508.

At 512, control identifies consumers that are enrolled in an individual family plan (IFP) database. Control than selects a first identified consumer at 516. At 520, control determines whether the selected consumer is a full-time employee. If control determines at 524 that the consumer is not a full-time employee, control removes the consumer from the training data, at 536. For example, control may remove part-time employees in order to avoid skewing the training data.

If control determines at 524 that the consumer is a full-time employee, control proceeds to 528 to determine which company employs the identified consumer. For example, control may implement the employer identification model illustrated in FIG. 9 and described further below. At 532, control labels the determined company as a non-benefit providing company in the training data. For example, if an identified consumer is enrolled in an individual family plan, this may suggest that the consumer's employer does not offer a company-sponsored health insurance plan.

At 540, control determines whether the last identified consumer has been selected. If not, control proceeds to 544 to select a next customer, and then returns to 520 to determine whether the selected consumer is a full-time employee. If control determines at 540 that the last identified consumer has been selected, control may end the process.

FIG. 6 is a flowchart depicting an example method of training the machine learning model of FIG. 4. Control begins at 604 by obtaining a list of companies and associated company firmographic variables from a company information database. At 608, control preprocesses the obtained variables to transform the variables into binary dummy variables.

At 612, control determines an association between dependent and independent firmographic variables. For example, the determination may involve two variables and take the form of a bivariate analysis. Control then performs stratified sampling of the identified non-benefit providing companies at 616, and combines the stratified sampling with the benefit providing companies to create training data.

At 620, control removes companies from the training data that do not have stored firmographic data available. Control then trains a random forest machine learning model, using the created training data, at 624. At 628, control performs post-processing on the output of the random forest machine learning model.

In various implementations, a machine learning model may be used to identify potential customers to buy an Individual Family Plan (IFP) according to various criteria. For example, the model may attempt to identify businesses that do not offer health insurance benefits to their employees. The model may use customer and client data to forecast companies that are most likely to not offer health insurance benefits to their employees. In various implementations, the model may incorporate an employer identification model (such as the models illustrated in FIGS. 7-10), in order to predict a most likely employer for each working person in a group (such as all working persons in the United States). Company-level data may be used as an input, where the model generates a probability score for each of the companies. The dependent or target variable may include one or more binary variables, with a level of 0 or 1. Predictors may include both numeric and categorical variables.

In various implementations, the model may provide a first output that includes the probability score measuring the likelihood of any company to not offer benefits to its employees. The higher the magnitude of the score, the higher the likelihood of the company not offering. Next, the score may be converted to the individual level by looking up the corresponding employees in an ExecuReach Grade 0 Database, or reverse-engineering an employer identification model (such as the models illustrated in FIGS. 7-10), to tie individuals to high-scoring companies. These individuals may be targeted in a campaign.

In various implementations, model input data may include business-level data, with an ultimate Duns number as the unique identifier for each row. This identifier may denote a headquarters for each. If any data is available at a branch level during preprocessing (for example, as denoted by Duns number or ABI number), the data may be rolled up to the headquarters level.

Companies with an employee size of less than twenty (or more or less), may be removed from the model data to eliminate a bias due to size. In various implementations, an event rate (such as 10% or more or less) may be assumed for the analysis, where 10% of the companies do not offer health insurance and the remaining 90% offer health insurance.

In various implementations, all the companies within a group (such as all United States companies), may be scored by an IFP eligibility machine learning model to receive a probability score (for example, ranging from 0 to 1), which measures a likelihood of a company not offering benefits to their employees. The scores may be placed into ten deciles (or other suitable groupings), by ranking the probability scores. Smaller, top deciles (for example, deciles 1-4) may suggest a higher likelihood of not offering health insurance to the employees. A cumulative gains chart may be used to show a K-S score of the model. For example, a larger gap between the model prediction outputs and randomly assigned probabilities may indicate a higher lift generation from the model and therefore a better prediction capability compared to random values. As one example, a model may have a first decile lift of 4.5, meaning the model predicts target audiences 4.5 times more accurately than choosing an audience randomly.

In some implementations, a top two deciles of the model may capture a sufficient percentage of actual events in the training and testing samples, such as around 58%-61% of the actual events. This suggest the model may identify around 58%-61% of companies that do not offer benefits to their employees, by scoring the data with the example model and taking only the top 20% population of the scored output data. In some cases, taking the top four deciles may capture around 75% of the likely events (or more or less). After identifying the companies in deciles 1-4, employees of the companies may be identified from a Grade 0 Database, or using the example employer identification models illustrated in FIGS. 7-10, and automatically targeted with marketing campaign information.

In various implementations, the model will cut down the campaign target population significantly (such as from 35 million down to 1.27 million). Data of all United States companies may be obtained from a D&B database. The whole database may be scored by the model. Then, the companies that remain in the top four deciles (or more or less), may be identified by rank-ordering the probabilities. The employees associated with the corresponding Duns number or converted ABI number may be identified from the Grade 0 Database, which contains the employment details of a significant number of United States individuals.

In various implementations, part-time workers may be removed from the database before creating the training sample. Couple scores may be generated in addition to, or instead of, individual scores, because the presence of employer insurance at an individual's company may ensure coverage of the spouse also. Therefore, in some cases an individual may be targeted for an IFP only if the spouse is also coming under the same umbrella by working in a company that does not offer benefits.

Example input data for the mode may include, but is not limited to, a number of payment experiences over various recent time periods that are past due (where more instances of past payments due suggests that health insurance is not offered by an employer), a number of corporate family relationships identified by a D&B database according to Duns numbers (where larger numbers of corporate family relationships may suggest that health insurance is not offered), a total number of payment experiences over a recent time period as reported to the D&B database (where a lesser number of payment experiences may suggest that benefits are not offered), a debt payment time period for the company (where companies that are slow to repay debts are less likely to offer health insurance), a number of slow payment experiences, a number of URLs per Duns number that have a live website, and a year that the business started (where older companies may be less likely to offer health insurance).

In various implementations, a B2B database may be used along with a B2C or consumer database, and one or more models connect B2B and B2C segments very smoothly. The model(s) may start from a B2B model, and convert to a B2C, to end in an individual-level campaign. The model(s) may use numerical and categorical business modeling features, combined with machine learning techniques, to achieve high accuracy and stability.

Employer Identification Model

Figure 7:
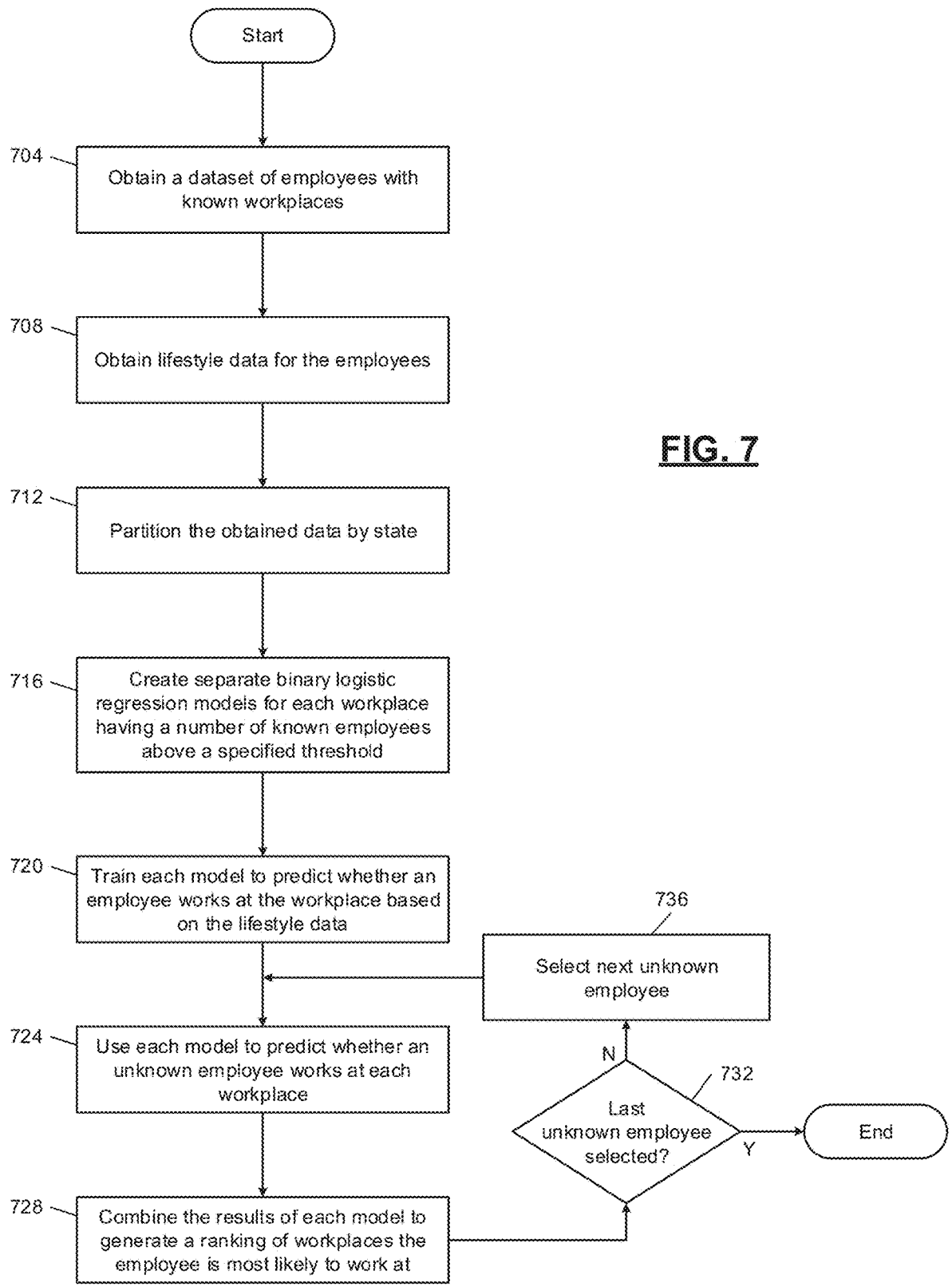
FIG. 7 is a flowchart depicting an example method of implementing a machine learning model for generation of an employer prediction output for an individual.

FIG. 7 illustrates an example process for identifying an employer of an individual. At 704, control beings by obtaining a data set of employees with known workplaces. For example, the Yes Lifecycle Marketing (YLM) ExecuReach dataset includes sixty to seventy million people with known workplaces, which may be used as a training set. Lifestyle data is obtained for the employees at 708, such as the lifestyle data 114 in the database 102 of FIG. 1. For example, an Infogroup database may provide up to 1800 variables for individuals, such as census tracts, numbers of vehicles, level of education, home value, television shows frequently viewed, and activity in sports.

At 712, control partitions the obtained data by state. Control then proceeds to 716 to create separate binary logistic regression models for each workplace having a number of known employees above a specified threshold (such as at least fifty employees, at least one hundred employees, at least five hundred employees, etc.). For example, each business may have a unique identifier (such as an ABI) in each state. For each state, a separate binary logistic regression model may be created for each business that has over one hundred employees. At 720, control trains each model to predict whether an employee works at the workplace based on the lifestyle data for the employee.

Once the models are trained, control uses each model at 724 to predict whether an unknown employee works at each workplace. The results of each model are combined at 728, to generate a ranking of workplaces that the employee is most likely to work at. For example, after all of the binary models have run, the results may be combined to create a ranking of ABI identifiers (for example, unique workplaces), that the employee is most likely to work at. At 732, control determines whether a last unknown employee has been selected. If not, proceeds to 736 to select a next unknown employee, and returns to 724.

In some implementations, explicit binary models are used instead of a multi-nominal logistic regression in order to allow for feeding different data into each binary model. In particular, the most important feature in some models is the distance form where a person lives to each ABI identifier, which is different for each unique combination of individuals and ABI identifiers. The model may use longitude and latitude to calculate the distance between an individual and the location of an ABI-identified business, on the fly as the model is running.

Figure 8:
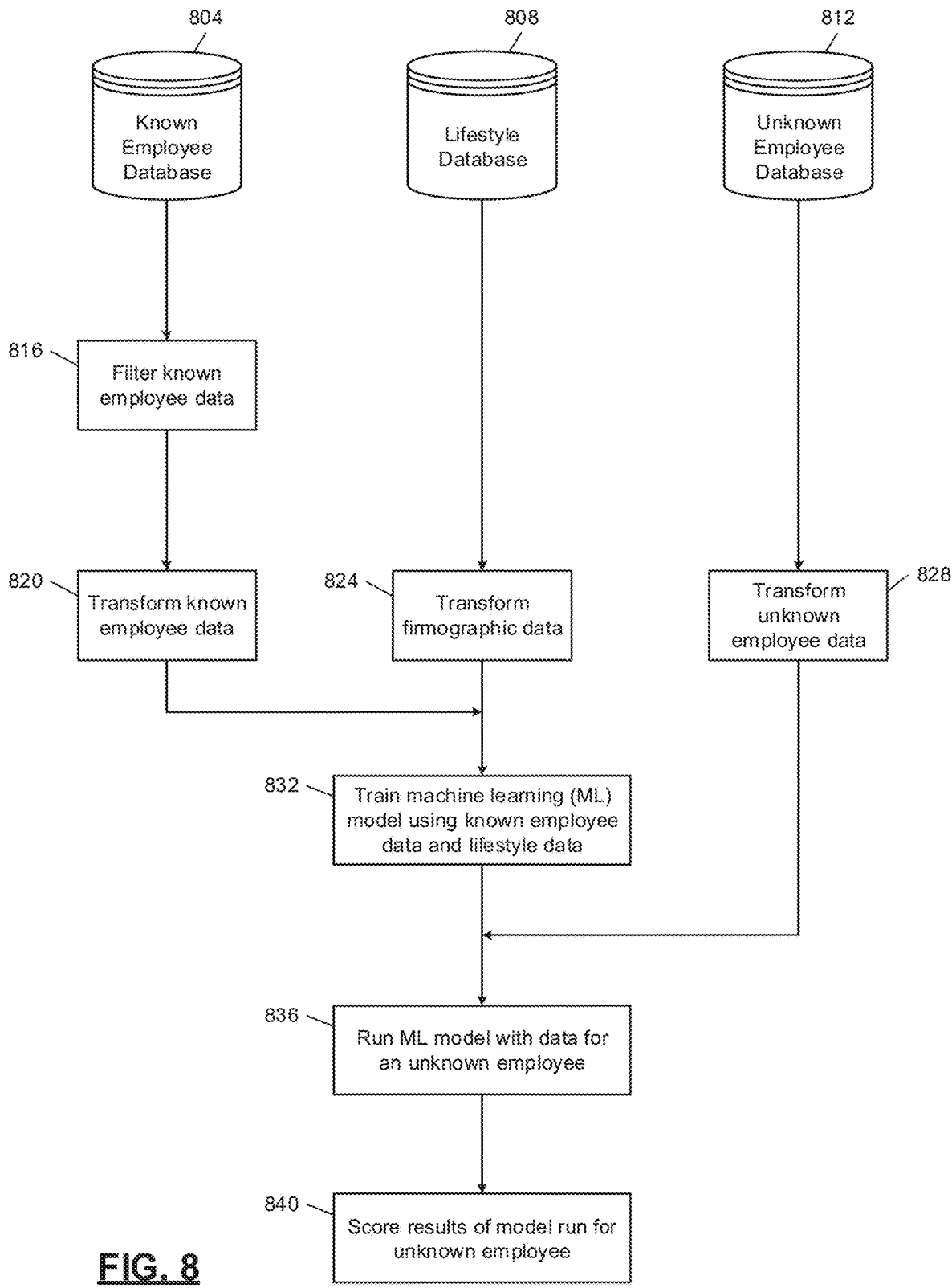
FIG. 8 is a flowchart depicting various data sources used for generating the model of FIG. 7.

FIG. 8 illustrates example datasets that may be used to build the model described in FIG. 7. For example, a known employee database 804 may include individuals where their employer is known, such as the YLM ExecuReach dataset. A lifestyle database 808 includes lifestyle details about different employers, such as the Infogroup database described above. An unknown employee database 812 includes lifestyle details about individuals whose employer is unknown, such as the YLM Consumer database.

The unknown employee database 812 is typically larger than the known employee database 804. For example, the known employee database 804 may be used to build the model using a training and testing data set of about sixty to seventy million individuals, while the unknown employee database 812 may be used to predict employers of two hundred and eighty million individuals.

As shown in FIG. 8, the known employee data is filtered at 816, and transformed at 820. For example, only a subset of the data from the known employee database 804 that is particularly relevant to model may be selected at 816, and any non-numeric elements of the data may be converted to numerical values at 820. Similarly, data from the lifestyle database 808 may be transformed at 824 by converting any non-numeric lifestyle variables to numerical values, and data from the unknown employee database 812 may be transformed at 828 by converting any non-numeric variables in the data to numerical values.

At 832, control trains the machine learning model using the filtered and transformed known employee data and lifestyle data. Once the model is trained, control runs the model at 836, using the transformed data from the unknown employee database 812. The results of the model run are scored at 840, which provides a prediction of where the unknown employee works.

Figure 9:
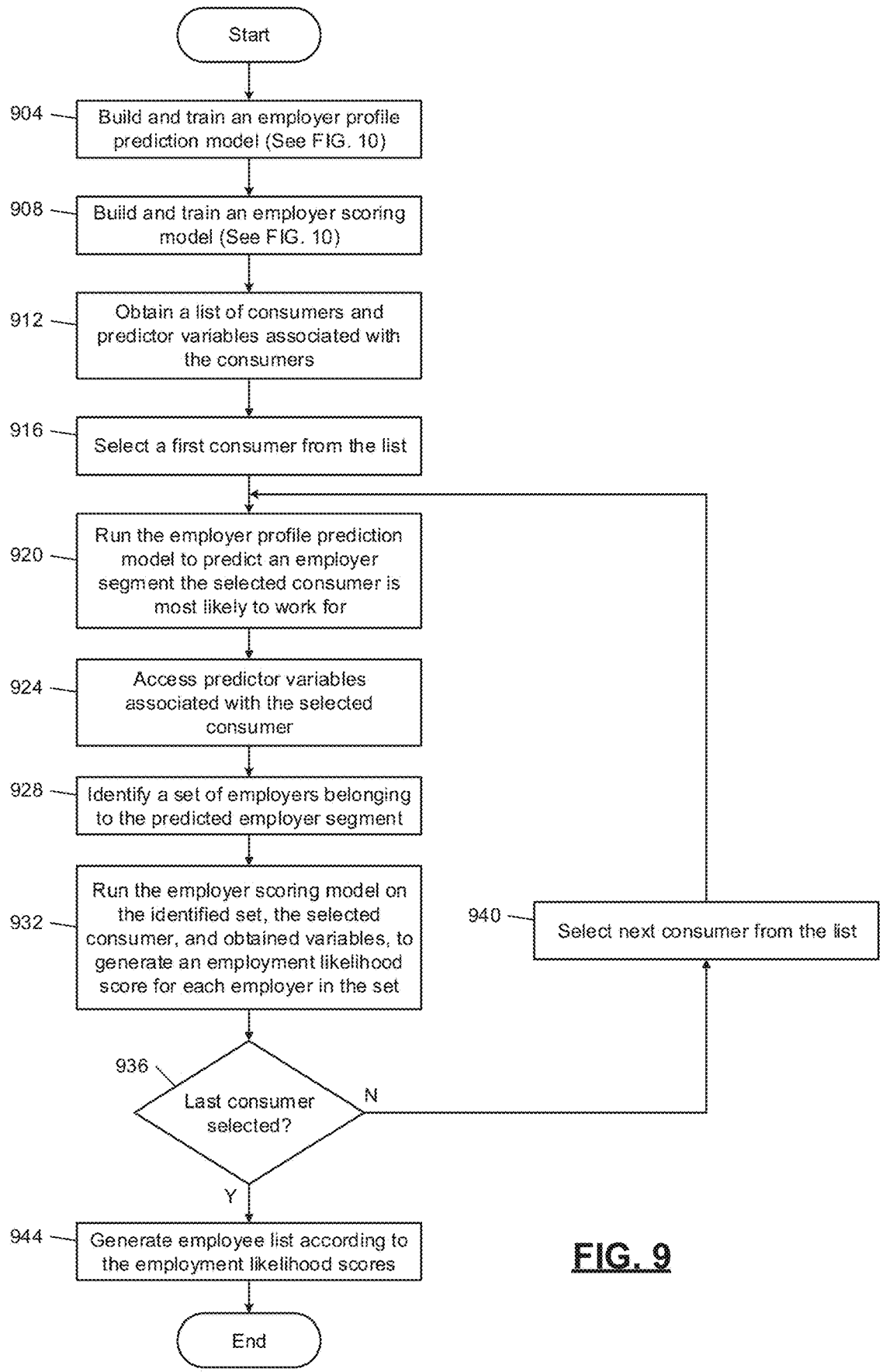
FIG. 9 is a flowchart depicting an example method of implementing a machine learning model for generation of an employer prediction output according to multiple employer segments.
Figure 10:
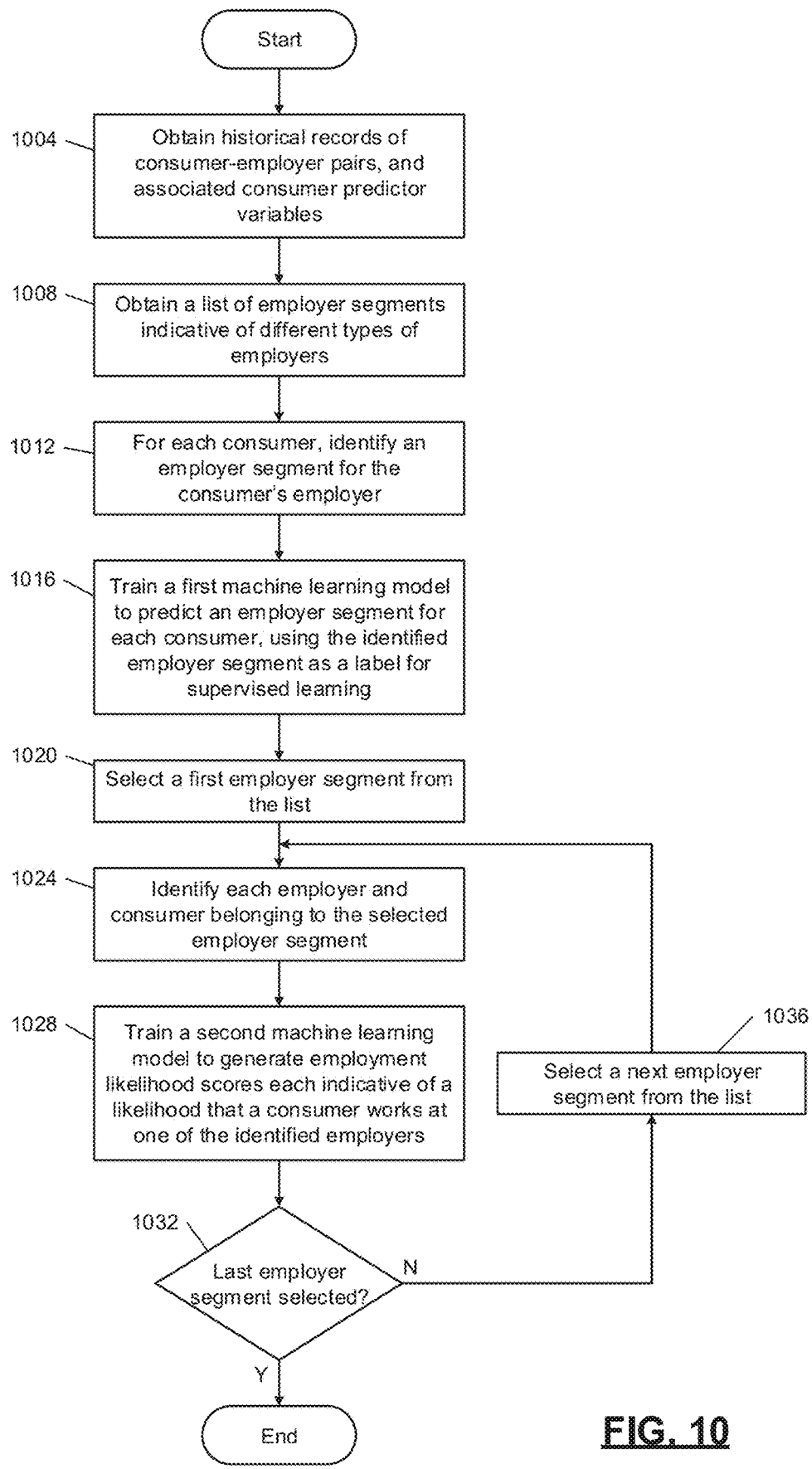
FIG. 10 is a flowchart depicting an example method of training the machine learning models of FIG. 9.

FIG. 9 is a flowchart depicting an example method of implementing a machine learning model for generation of an employer prediction output according to multiple employer segments. At 904, control begins by building and training an employer profile prediction model. An example of building and training the employer profile prediction models is illustrated in FIG. 10, and described further below At 908, control builds and trains an employer scoring model. An example process for training the employer scoring model is also illustrated in FIG. 10, and described further below. At 912, control obtains a list of consumers and predictor variables associated with the consumers. Control then selects the first consumer from the list at 916. At 920, control runs the employer profile prediction model to predict an employer segment that the selected consumer is most likely to work for (for example, by generating a segment output indicative of one of the multiple employer segments that has a highest likelihood of association with the consumer entity).

Control proceeds to access predictor variables associated with the selected consumer at 924 (such as a drive time from each employer, and a household income level). Control identifies a set of employers belonging to the predicted employer segment at 928. At 932, control runs an employer scoring model on the identified set, selected consumer, and the obtained variables, to generate an employment likelihood score for each employer in the set (for example, by generating an employment likelihood output indicative of one of the set of employer entries that has a highest likelihood of association with the consumer entity).

The example process of FIG. 9 may be similar to the example process of FIG. 7, with an additional model used to predict an employer segment that the selected consumer is likely to work for. This allows the employer scoring model to be run within a predicted employer segment and not the entire data set of employers, thereby potentially increasing the accuracy and speed of the prediction by running the model on a smaller segment of the overall dataset.

At 936, control determines at the last consumer was selected. If not, control proceeds to 940 to select the next consumer from the list, and returns to 920 to run the employer profile prediction model to predict an employer segment that the next selected consumer works within. If control determines at 936 that the last consumer has been selected, control proceeds to 944 to generate an employee list according to employee likelihood scores (for example, a list of the most likely employer(s) that each consumer works for). Control may transform a user interface to display the employment likelihood output.

FIG. 10 is a flowchart depicting an example method of training the machine learning models of FIG. 9. At 1004, control begins by obtaining historical records of consumer-employer pairs (such as listings of companies and their employees), and associated consumer predictor variables. At 1008, control obtains a list of employer segments indicative of different types of employers (for example, a listing of six different categories of employer types, or more or less).

Control then proceeds to 1012 to, for each consumer, identify an employer segment for the consumer's employer. At 1016, control trains a first machine learning model to predict employer segment for each consumer using the identified employer segment as a label for supervised learning. At 1020, control selects a first employer segment from the list. Control identifies each employer and consumer belong to the selected employer segment, at 1024.

At 1028, control trains a second machine learning model to generate employment likelihood scores each indicative of a likelihood that a consumer works at one of the identified employers within the employer segment. For example, while the first machine learning model may be used predict a type of employer segment that the consumer is most likely to work within, the second machine learning model may be used to identify an actual employer that the consumer works at within the predicted employer segment.

At 1032, control determines whether the last employer segment is selected. If not, control proceeds to 1036 to select the next employer segment from the list, and returns to 1024 to identify each employer and consumer belonging to the selected employer segment. If control determines at 1032 that the last employer has been selected, control may end the process.

In various implementations, an employer prediction machine learning model may use a preprocessing algorithm to divide the process up into smaller jobs. For example, in some cases an employer prediction model algorithm may run on a full consumer population, against a full set of employers (such as all United States employers). In other implementations, the model algorithm may be run in multiple separate batches (such as six batches), with specific selections of the population being run against only the employers that correspond to the specific selection of the population.

For example, employers may be divided into six client segments (or more or less). The model may match consumers to these same six client segments using their current employment data, to train an employer profiling machine learning model, using a pre-sorting algorithm. The employer profiling model may predict which client segment an individual consumer is most likely to prefer working for, therefore enabling a division of both the consumer and employer populations into six corresponding segments (or more or less), and splitting up the subsequent employer prediction model operation into six smaller batch jobs.

Choice Model

Figure 11:
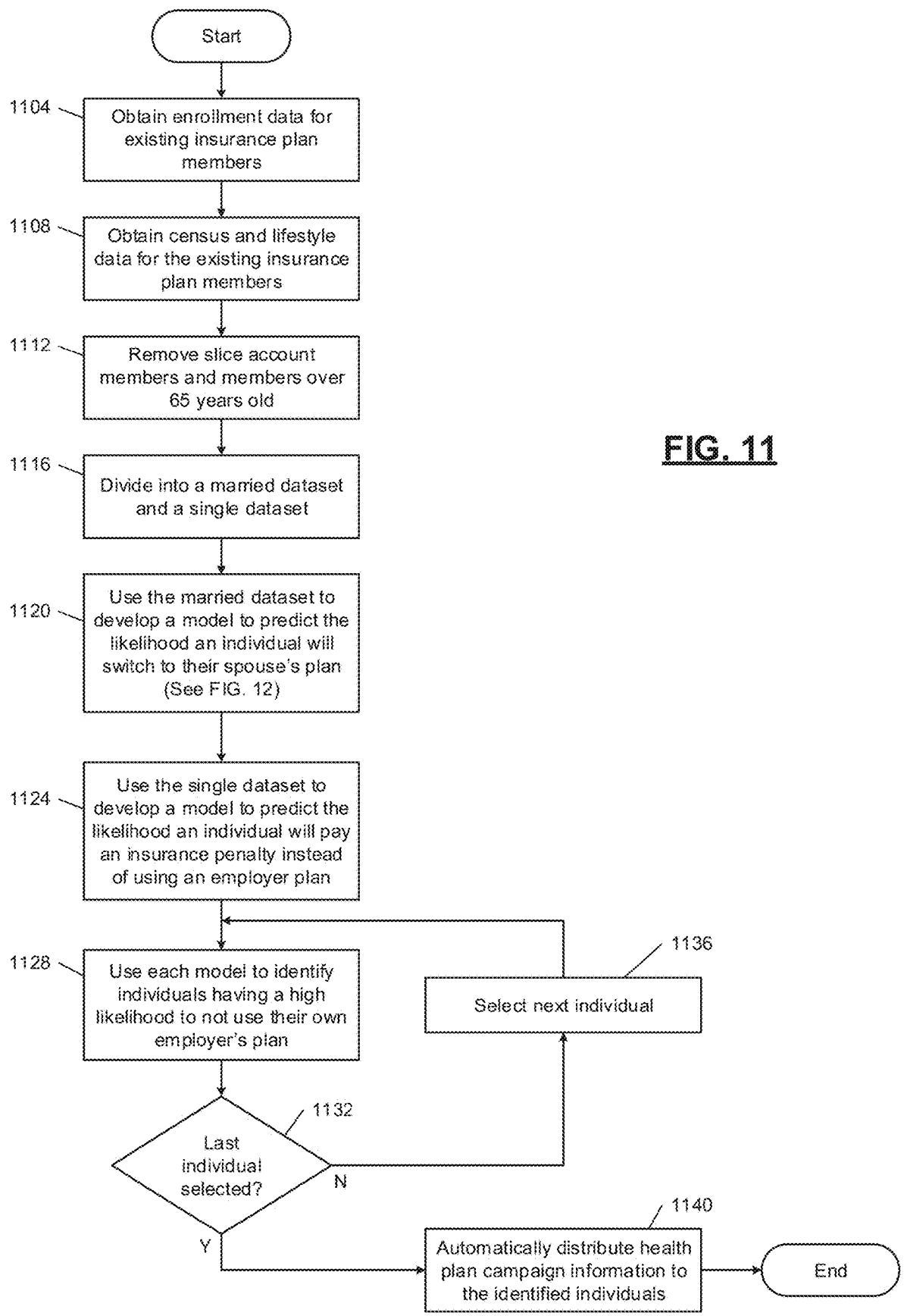
FIG. 11 is a flowchart depicting an example method of implementing a machine learning model for generation of a non-employer insurance prediction output.

FIG. 11 illustrates a process of generating a machine learning model for predicting whether an employee is likely to use health insurance from a plan other than their employer-sponsored plan. Control begins at 1104, by obtaining enrollment data for existing insurance plan members. Census and lifestyle data for the existing insurance plan members are obtained at 1108.

At 1112, control removes slice accounts (such as accounts at companies that offer more than one insurance provider option), and members over sixty-five years old (or any other suitable age threshold). These groups may be considered as special cases that would otherwise bias the model (because individuals on Medicare may no longer have a need to use an employer-sponsored plan).

Figure 12:
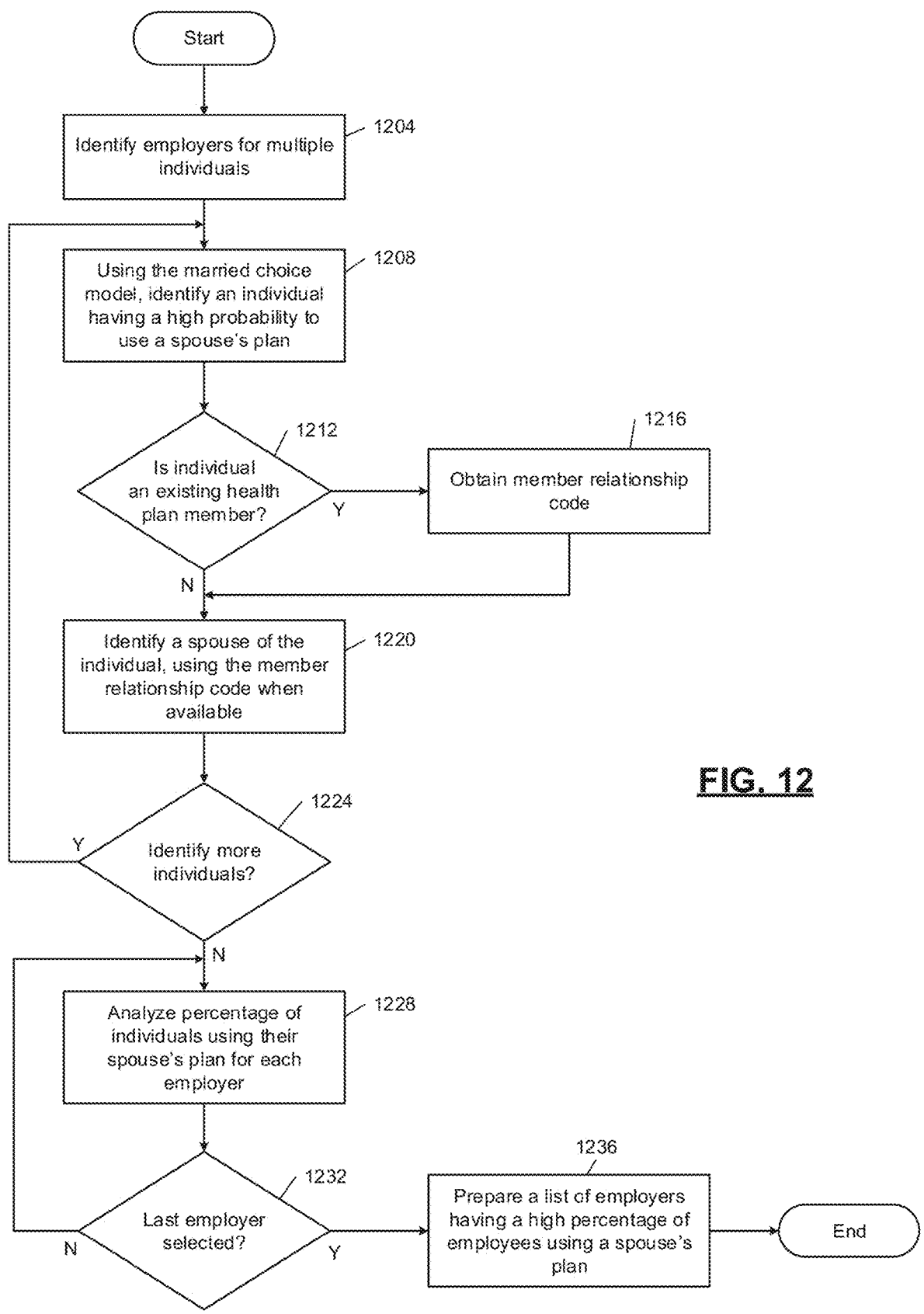
FIG. 12 is a flowchart depicting an example method of implementing a machine learning model for generation of an employer spouse plan prediction output.

Control divides the data into a married individual data set and a single individual dataset, at 1116. The married dataset is used, at 1120, to develop a model to predict the likelihood of an individual switching to their spouse's plan. An example process for training a spouse's insurance prediction model is illustrated in FIG. 12, and discussed further below. At 1124, the single dataset is used to develop a model to predict the likelihood of an individual paying an insurance penalty instead of using an employer-sponsored plan.

At 1128, each model is used to identify individuals having a high likelihood to not use their own employer's plan. For example, lifestyle data of a married employee may be entered as an input to the model, and the model may predict the likelihood that the married employee will use their spouse's health plan instead of the employer-sponsored plan. Similarly, lifestyle data of a single employee may be entered as an input to the model, and the model may predict the likelihood that the single employee will not use employer-sponsored plan and will pay a penalty tax instead.

At 1132, control determines whether the last target individual has been selected. If so, the process ends. If the last target individual has not yet been selected, control proceeds to 1136 to select the next target individual, and then back to 1128 to use the model to identify the likelihood that the next target individual will not use the employer-sponsored plan (for example, by generating a selection score output indicative of a likelihood that the individual entity will select a service provided by an employer of the entity). Once the last individual is selected at 1132, control proceeds to 1140 to automatically distribute health plan information to the individuals identified as having a high likelihood to not use their own employer's plan (such as a likelihood output exceeding a threshold value).

While developing the model, a system administrator may use any suitable techniques for understanding the available feature space and finding patterns by plotting, creating charts, and using descriptive statistical techniques. The data acquired may be a large sample, with more than 1500 variables in some cases. Preprocessing steps may be used to clean the data prior to training the model or using the model, including column renaming, scaling numerical variables, encoding categorical variables, binning, creating dummies, dropping variables which are determined to not have sufficient significance, handling different data types, imputing values, and creating training and test samples.

Optimized machine learning modelling techniques may be used to choose the best models, and hyper-parameters may be tuned while considering impacts on performance, accuracy, bias, and variance, of the model, including evaluation by calculating and plotting a gains-lift chart. Both local and cloud platforms may be used per data size and business requirements. Once the model is ready, the model may be used to score for different campaigns, including both acquisition and retention campaigns.

FIG. 12 illustrates a process of generating a machine learning model for determining employers that have high percentages of employees using a spouse's health plan. Control begins at 1204, by identifying employers for multiple individuals. For example, a database of known employee-employer relationships may be used, or a model such as the models generated by the processes of FIGS. 7-10 may be used (for example, to predict the maximum likelihood workplace(s) for an individual based on lifestyle data).

At 1208, control uses the married choice model to identify an individual having a high probability of using a spouse's health plan instead of the employer-sponsored plan. Control determines whether the identified individual is an existing health plan member at 1212. If so, a member relationship code is obtained at 1216. Control identifies a spouse of the individual at 1220, using the member relationship code if available. Alternatively, the spouse may be determined based on other information such as age or sex.

Control determines whether there are any more individuals with an identified employer at 1224. If so, control proceeds back to 1208 to identify another individual having a high probability to use a spouse's plan. When there are no more individuals to consider, control proceeds to 1228 to analyze, for each employer, a percentage of individuals using their spouse's plan.

When there are more employers to select at 1232, control proceeds back to 1228 to analyze a percentage of employees using their spouse's plan, for another employer. When each employer has been analyzed, a list of employers having a high percentage of employees using a spouse's plan is prepared at 1236. For example, a high percentage may indicate that spouses have superior health plans than the one offered to the employee by the employer.

In the commercial medical health plans sector, enterprise (for example, client) accounts can be grouped into various types, such as single carrier, multiple carrier, private exchange (PIX) and others. Conventional marketing campaigns direct advertisement to all employees (for example, individuals) of a health insurance provider's clients regardless of the account type. Two main types of campaign are usually conducted throughout the year, namely acquisition and retention.

The choice model framework proposes an alternative marketing strategy to maximize a campaign's effectiveness and cost. Under different account types, individuals may be exposed to various healthcare plan options. For example, leaving an employer-sponsored health plan is one option for some individuals. In example frameworks described herein, the models may aim to discover the potential choices that are readily available for each individual, and allocate resources or marketing effort to those having more options.

Generally, the choice model framework may be used for the following individual choices (or others): (1) a slice/PIX account, where a slice model predicts a likelihood of an individual joining another health insurance provider; (2) a working spouse, where the married model predicts a likelihood of an individual switching to their spouse's employer sponsored insurance plan; and (3) a single individual, where the single model predicts the likelihood of an individual not purchasing insurance and instead paying a tax penalty.

One of the goals of the example models described herein may be to identify customers who have choices to switch their insurance policies. The developed model is expected to identify whether a customer has a "choice" or "no-choice" to switch his/her insurance plan. Customers who are predicted to have "no choice" should be less likely to leave or not enroll, as compared to customers having a "choice". In other words, the leave or non-enrollment rate of the "no-choice" group should be significantly lower than the "choice" group.

Example lifestyle data for building the model may include, but is not limited to, age, estimated household relative purchasing power, early adopter households, country music concert attendance, recent garden/maintenance, early users of the Internet, household size, pay-per-view ordering, saltwater fishing frequency, whether the household is heated with electricity, mortgage data validation, homeowner or renter, race, utility gas heating, average travel time to work, likelihood to eat frozen dinners, current auto loan probability, the probability of small business insurance, college football attendance, likelihood of hunting, and a likelihood of online investment and training.

Figure 13:
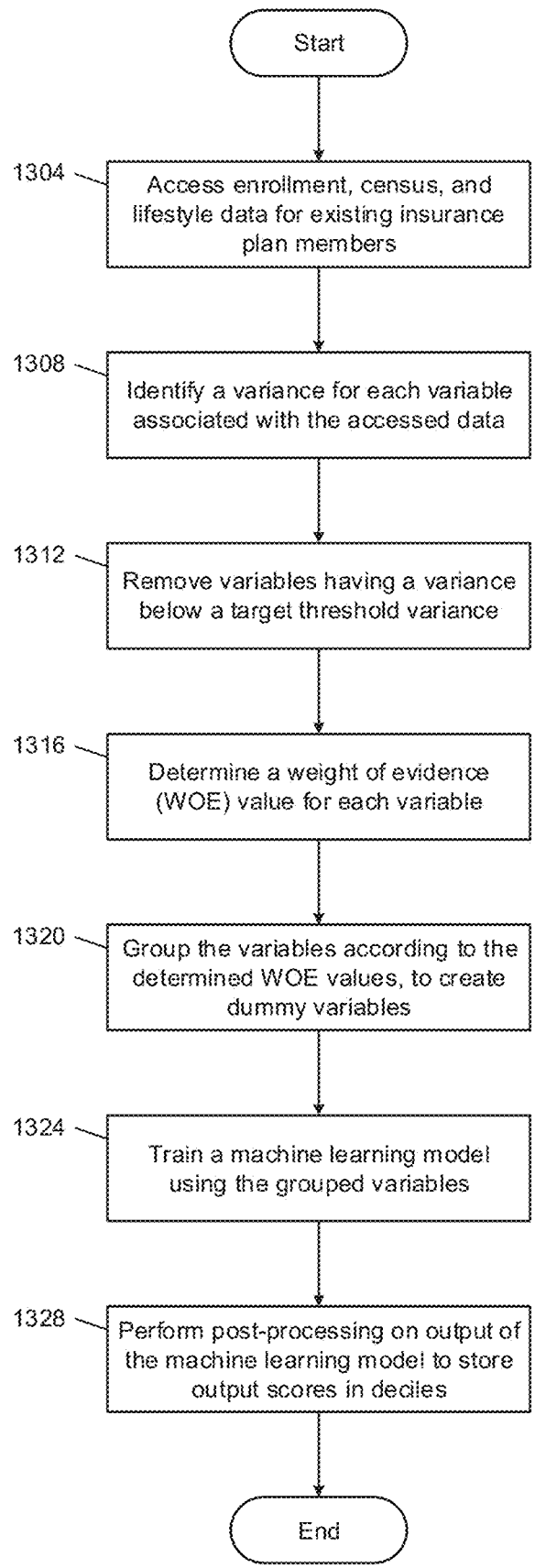
FIG. 13 is a flowchart depicting an example method of training the machine learning models of FIG. 11.

FIG. 13 is a flowchart depicting an example method of training the machine learning models of FIG. 11. At 1304, control begins by accessing enrollment, census, and lifestyle data for existing insurance plan members. Control proceeds to 1308 to identify a variance for each variable associated with the accessed data.

At 1312, control removes variables having a variance below a target threshold variance. Control then determines a weight of evidence (WOE) value for each variable, at 1316. At 1320, control groups the variables according to the determined WOE values, to create dummy variables.

At 1324, control trains a machine learning model using the grouped variables. Control then performs post-processing on an output of the machine learning model, to store outputs of the model in deciles (or any other suitable groupings), at 1328. Any suitable machine learning model may be used in various implementations.

In various implementations, a machine learning model may be used to quantify a degree of competition that a health insurance provider faces to earn a prospect or customer's business. A proxy for this estimation may be generated by quantifying a number of options available to individuals in terms of their health insurance provider. Using this information, it may be possible to determine which individuals may not be likely or guaranteed enrollees, and therefore could use extra attention. This may help maximize a total number of members that are acquired and retained.

Model input data may include lifestyle variables, demographic variables, household variables, census variables, and any other suitable variables, at an individual level. The variables may include YLM and employment information, along with a number of options available in terms of a number of carriers that are using YLM executive reach, D&B, and ERISA data sources.

The training data prepared for this model consists of data from B2B and B2C data sources. Feature selection/elimination is a critical step in preprocessing. A first step may be to identify variables that do not have a sufficient amount of variance, and removing them because they do not contribute to predicting the target variable.

The model may provide an output as a predicted probability that a consumer has additional health insurance choice options, and may be in the form of a binary classification model with levels 0 and 1. Higher probabilities may indicate individuals with a higher number of alternative health insurance choices, and vice versa. Predictors may contain both numeric and categorical attributes.

The model may be packaged as a Docker container. An image may be deployed to a company cloud infrastructure in the scoring process. A contact list will be collected from a data store and loaded into the container by appending the data sources. The contact list may be divided into single and married lists using a marital status flag. The model may be leveraged for both acquisition and retention campaigns, where corresponding inputs are a universe of prospects and an internal customer base, respectively.

In various implementations, model performance may be measured according to gain charts. A model with a maximum cumulative gain in the top four deciles and maximum lift may be considered as a better model. Preprocessed training data may be used to build a machine learning model, by training any suitable modeling algorithm (such as random forest, logistic regression, and light gradient boosting) on the data. The models may be tuned using hyper parameters to obtain maximum gain, and may be validated using a validation dataset. If the model performance is consistent with the training data, the tuned model may be considered as a stable model. Performance of each model may be evaluated and then compared with various models that have been built. A model that obtains the maximum performance metric among the models may be checked with a sample validation test before the model is put in production.

A random forest algorithm may classify every company into one of multiple classes uniquely, depending on certain features of the prospect candidate, using a maximum-voting method. Every tree of the forest may classify each prospect into one of the classes (such as 0 or 1). Then whichever class gets more votes may be assigned to that particular prospect. In addition, the proportion of votes that the company or the observation has received in favor of the class, may be treated as the measure of likelihood or probability score of that observation, for that particular class. All significant features obtained from the model may be included in the final model, and the features may be changed in subsequent generations of the model (for example, the model may be retrained over time to determine varying importance of different input features as the training datasets develop). In various implementations, the model may receive input that includes B2C and B2B data sources, along with engineered additional features. The model input data may include individual plan offerings, spouse plan offerings, and alternative offerings like Affordable Care Act options, and may be used for both acquisition and retention campaigns.

Decision Committee Model

Figure 14:
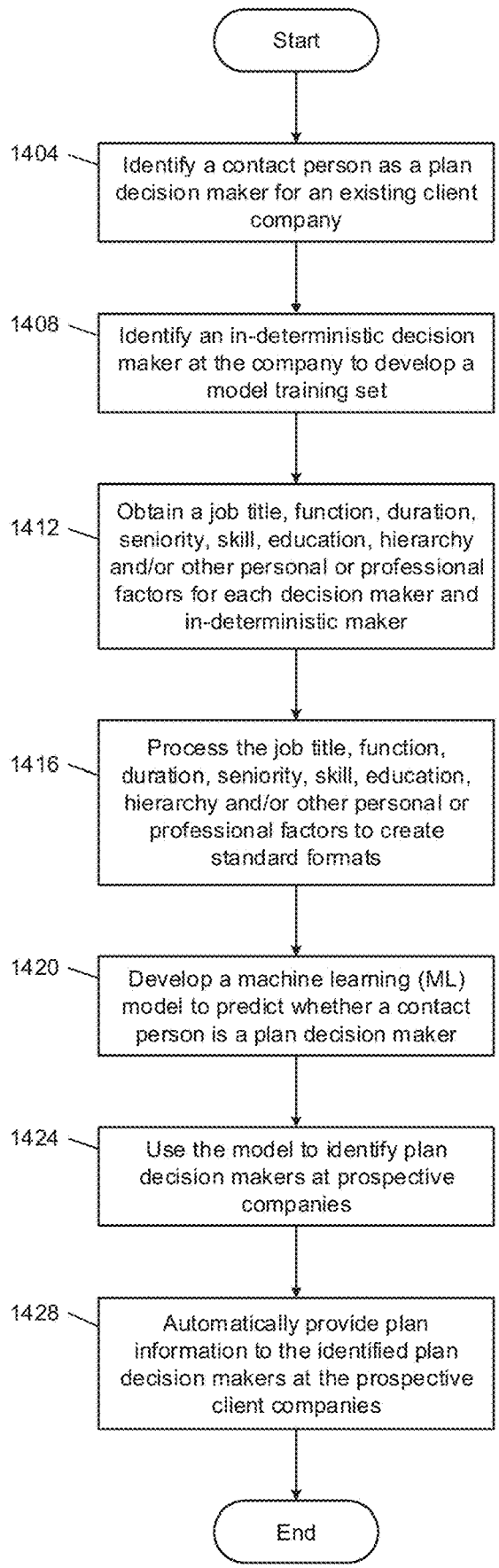
FIG. 14 is a flowchart depicting an example method of implementing a machine learning model for generation of a company decision maker prediction output.

FIG. 14 illustrates an example method for generating a machine learning model for predicting whether a contact person at a company is a plan decision maker for the company. At 1404, control begins by identifying a contact person as a plan decision maker for an existing client company, and at 1408 control identifies an in-deterministic decision maker at the company. For example, manual analysis and data classification may be used to identify known contact persons at a company that are responsible for deciding what health plan the company is going to offer to its employees, as compared to in-deterministic decision maker contact persons that are not involved in the decision. This manual analysis may be performed by an administrator of a health insurance provider that is familiar with the client company personnel, by interviewing or surveying different client companies.

At 1412, control obtains a job title, job function, job duration, job seniority, specified skill, level of education, hierarchical structure of an organization, and/or any other relevant personal or professional factors, for each identified decision maker contact and each identified in-deterministic decision maker contact (for example, control may obtain historical profile data structures that are specific to multiple prior contact entities, where the historical profile data structures include structured title data, structured response data and structured background data). The obtained variables may include key data types, category data types, text data types, dates, floats, etc. A person identifier may include a unique person identification number, a company identifier may include a company identification number, a job function may include functionality of the position the prospect is serving, a job title may include a title of the prospect's position, a seniority variable may include a leadership ranking of the position, a starting year variable may include the year in which the prospect started to work in their current position, and a career background variable may include career background information (such as job skills) that have been declared by the prospect.

The job title, job function, job duration, job seniority, specified skill, level of education, hierarchical structure of the organization, and/or other relevant personal or professional factors, are processed at 1416 to create standard formats. Control develops a machine learning model at 1420 to predict whether a contact person is a health plan decision maker (for example, for a prospective client company).

Control uses the model to identify plan decision makers at non-client companies at 1424, and automatically provides plan information to the identified plan decision makers at the prospective client companies, at 1428. This may include any suitable automated process for generating emails, social media advertisements, digital advertisement purchases, entertainment content streaming advertisements, etc., that target the identified decision maker at the prospective client company. Because the identified decision makers are more likely to respond with the authority to select a new health plan for their company, cheaper and more effective campaigns may be implemented, to primarily target only decision maker contact persons at the prospective client companies.

A "decision maker (DM) contact person" may be considered as individual who is a critical person in a prospective organization, to authorize signing a contract for a new employer-sponsored health plan, etc. A person may be defined as a DM based on historical records, based on model prediction, etc. The DM may serve as a key communication channel for marketing. A "decision committee (DC)" may refer to a group of influencers that affect the final decision for adopting a new health plan within an organization. They may be employees who work closely with the DMs, such as superiors, subordinates, cross-function colleagues, etc.

A decision committee model (DCM), such as the model generated by the example process of FIG. 14, may serve as a tool for a business to business acquisition campaign. The model may be used to assist in discovering decision makers or decision committee members of target commercial institutions. The model moves away from the traditional approach that relies heavily on human judgement, by leveraging machine learning, and expanding the radar to target contact persons in a decision committee.

The model may be a layered model, where the first layer receives a job title and the second layer receives career background information such as a job function, seniority, duration, skills, etc., to generate probability scores to predict whether a contact person is a decision committee member. The datasets for building the model may initially be based off of historical marketing personnel contacts with company staff to sell corporate plans, where successful marketing efforts are indicative that the personnel contact is a decision maker. Additional datasets may also be used to add persons who are not considered to be decision makers.

Job title is often a critical variable in the decision maker models. Therefore, job title data may be preprocessed with a number of text preprocessing steps or techniques. After the text preprocessing steps, a standardized final title name will be generated. The standardized title name may be unlike ordinary readable English. However, it may substantially reduce the amount of unique words, and also reduce uncaptured information due to human errors.

Some models may simply use a job title as the input, where the processed job titles are tokenized and a dataset having a machine-readable format, such as a term frequency table or a word-embedding vector, is created. A target variable is derived from the training datasets, by concatenating the decision maker and in-deterministic decision maker datasets together and assigning a class to each. The dataset may be separated into training, validation and testing sets. For example, a ratio of seventy percent training data, twenty percent validation data, and ten percent testing data. Alternatively, any other suitable ratios may be used.

The ratio of decision makers and in-deterministic decision makers in an original dataset may be highly imbalanced, with a decision maker rate of only about five percent in some implementations, etc. The model may use up-sampling where decision maker records are duplicated (for example, doubled or tripled), and may use down-sampling where in-deterministic decision maker records are resampled without replacement (for example, down to half of the size, or down to one-third of the size). Resampling increases the ratio of decision makers to in-deterministic decision makers in the dataset.

In some implementations, the model uses a second layer that incorporates contact-specific attributes, including career background information such as work skills, job functions, years of experience, etc. A mapping table may be used for job function matching, to facilitate use of different values and terminology in the job function fields in different datasets. Similarly, career background attributes may be processed into a standard format. Based on frequency, the most relevant career background details are identified and then feature importance may be performed to obtain an optimized set of predictors to be used in the model.

A model may be built using internal datasets for validation purposes. A gradient boosting model may be fit on tokenized title keywords to predict a job function label. In model scoring, a predicted job function may be used for correction if the prediction score exceeds a threshold (for example, 0.8).

In some implementations, numerous features may be used to generate the output, including a person identifier, a company identifier, career background information, a job function, a job title, a job seniority, a job duration, job skills, etc. Multiple prediction scores may be generated, such as a score predicted by job title alone, a score predicted based on additional variables such as career background information, job function, seniority, duration and skills, etc. A 'weighted average prediction by ratio' approach may be used for multiple prediction scores. This self-defined function may use different ratios to provide different proportions for different model prediction outputs. By comparing the prediction scores, a given number of potential decision makers may be selected. The model can also generate a list of decision makers and decision committee members by providing a desired number of decision committee members that have a direct relationship with the decision maker.

Figure 15:
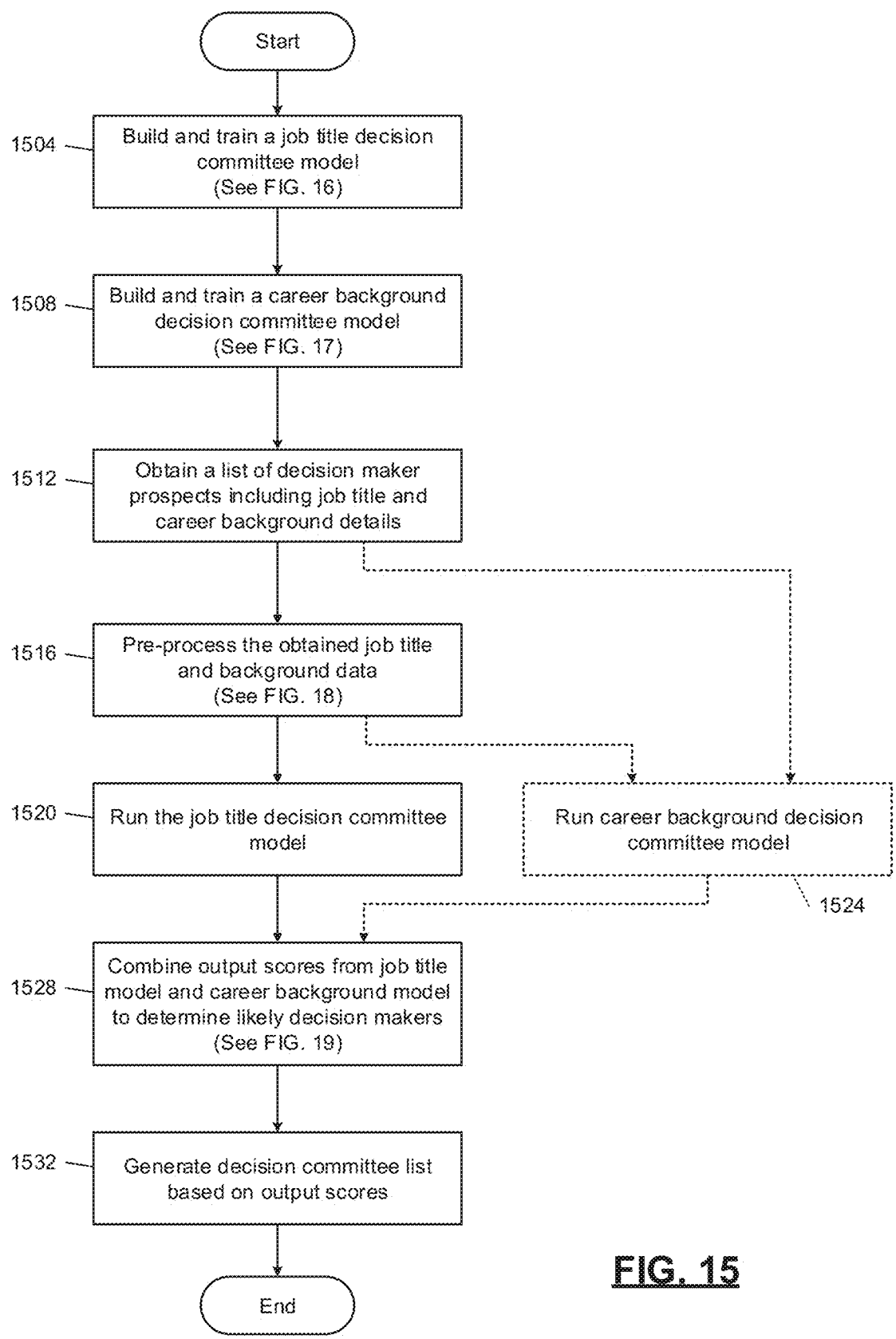
FIG. 15 is a flowchart depicting an example method of implementing a job title machine learning model and a career background machine learning model for generation of a company decision maker prediction output.
Figure 16:
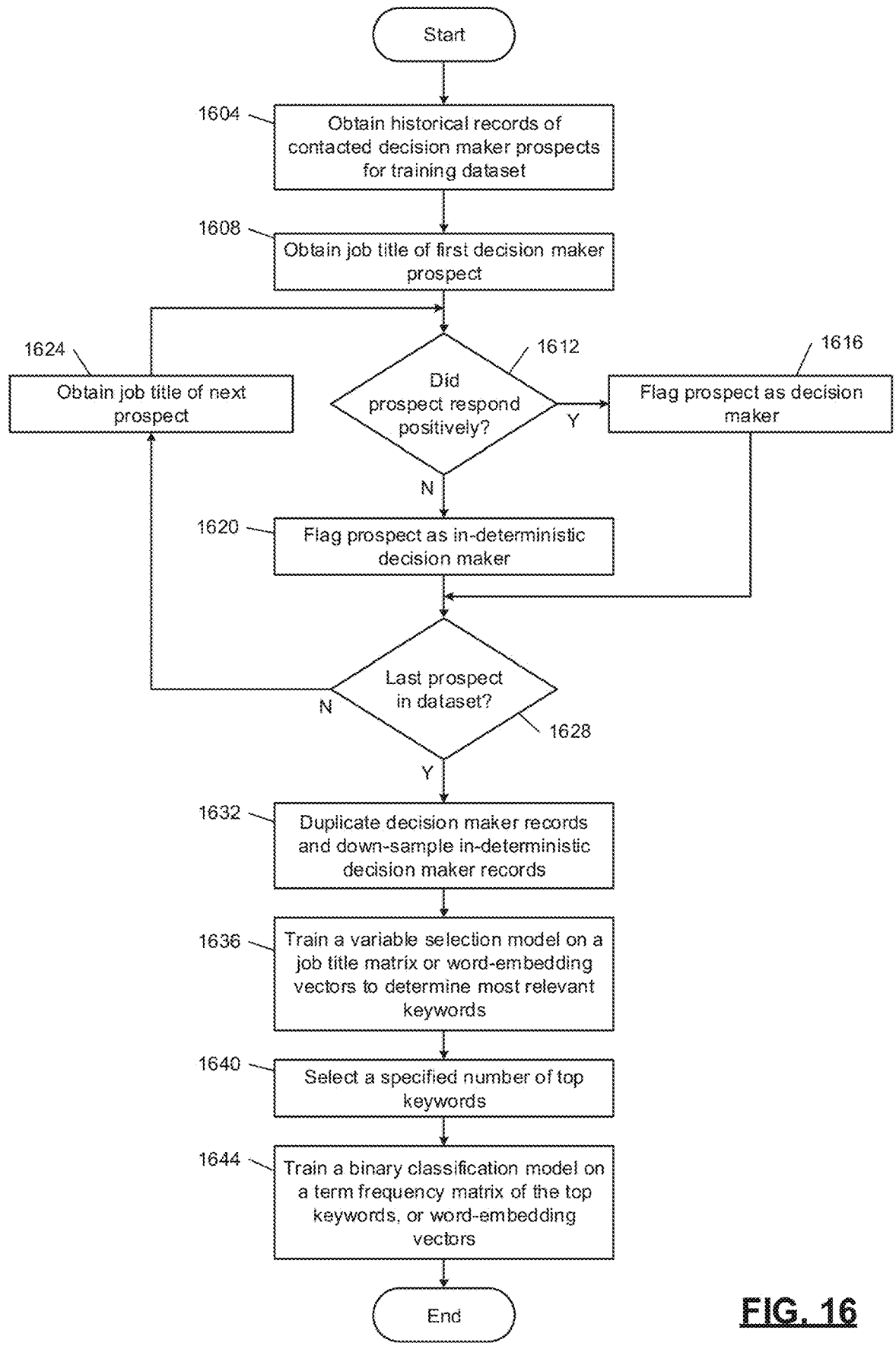
FIG. 16 is a flowchart depicting an example method of training the job title machine learning model of FIG. 15.

FIG. 15 is a flowchart depicting an example method of implementing a job title machine learning model and a career background machine learning model for generation of a company decision maker prediction output. At 1504, control begins by building and training a job title decision committee model. An example process for training the job title decision committee model is illustrated in FIG. 16, and described further below.

Figure 17:
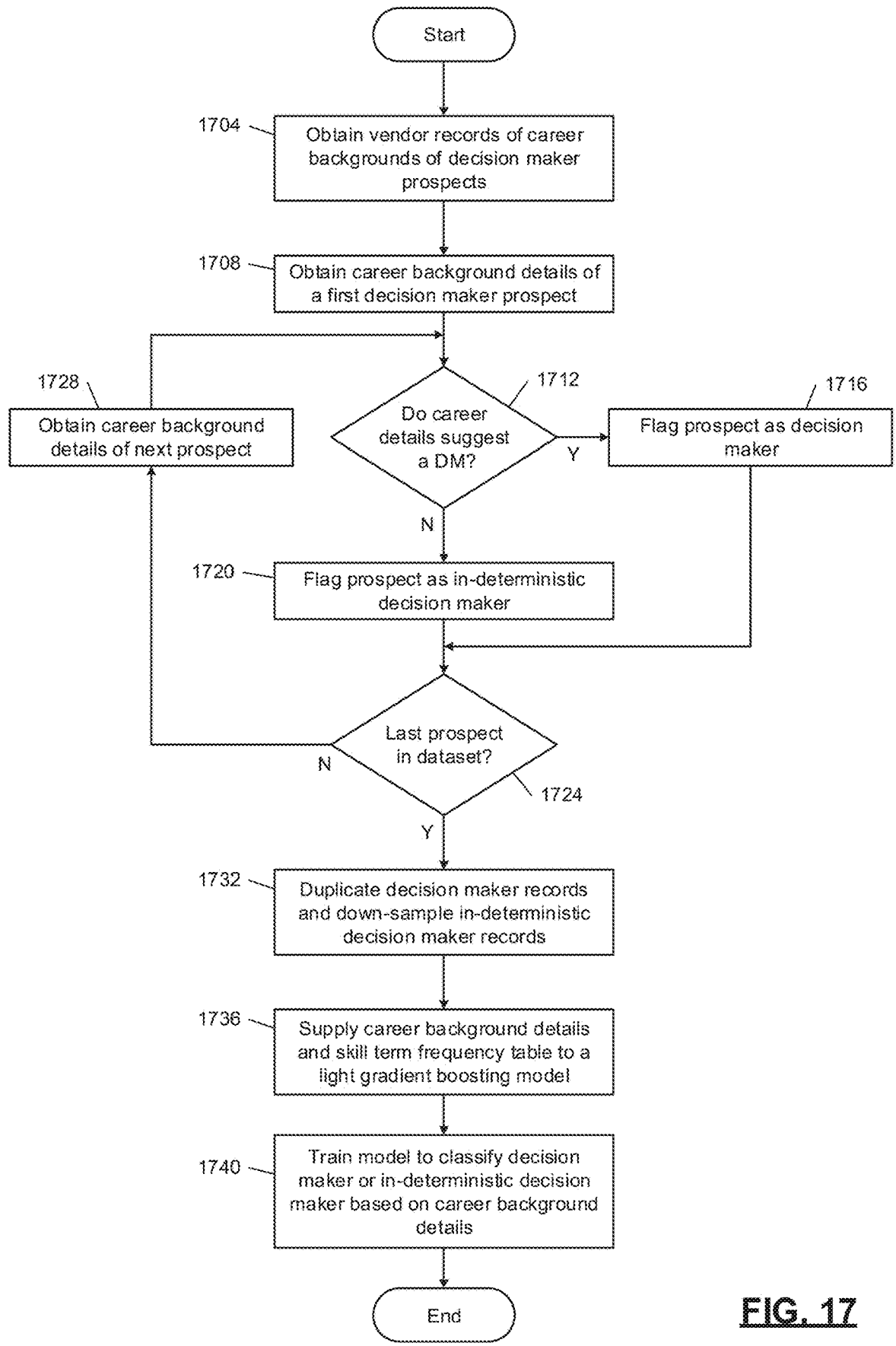
FIG. 17 is a flowchart depicting an example method of training the career background machine learning model of FIG. 15.
Figure 18:
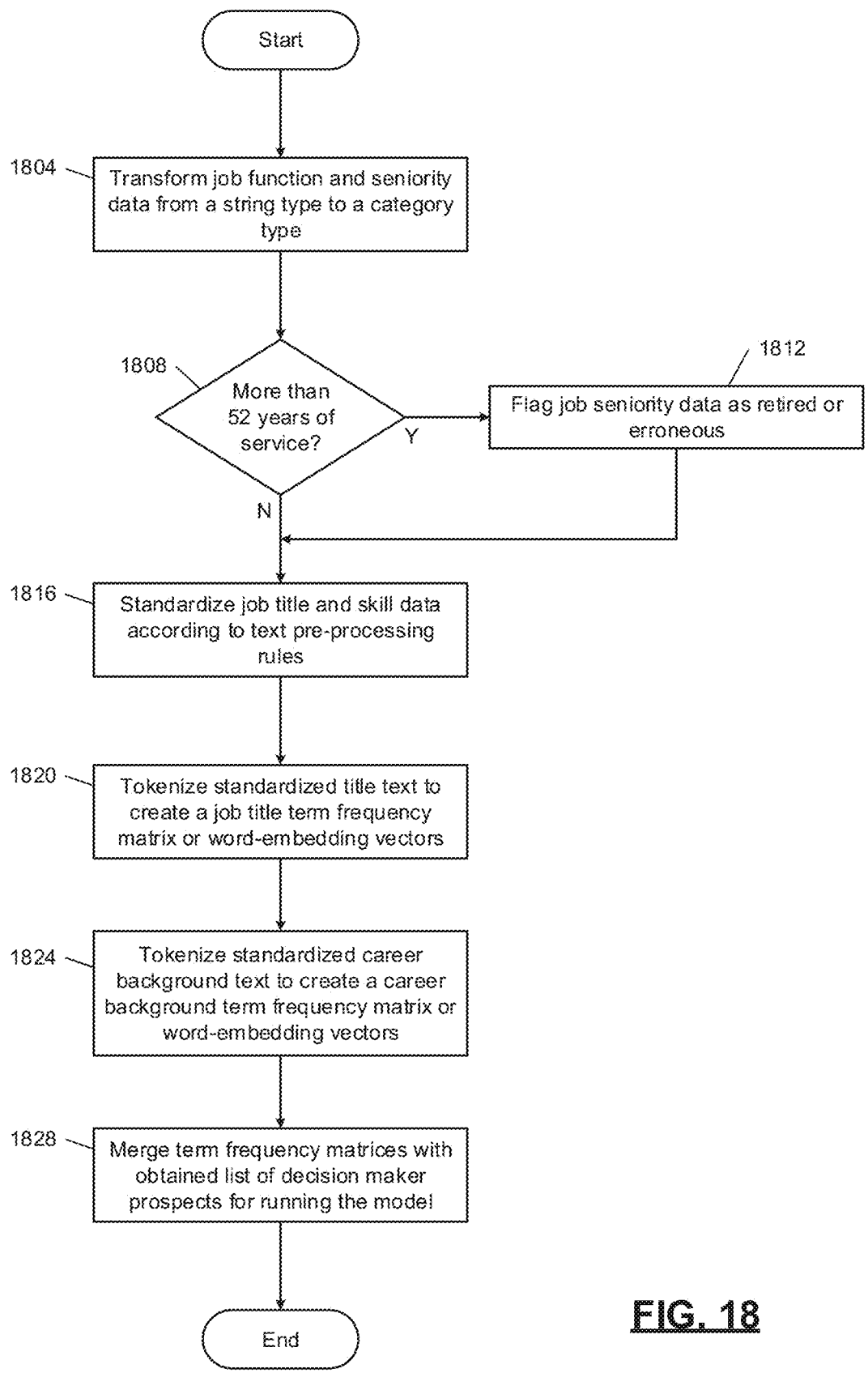
FIG. 18 is a flowchart depicting an example method of preprocessing input data for the job title and career background machine learning models of FIG. 15.

At 1508, control builds and trains a career background decision committee model. An example process for training a career background decision committee model is illustrated in FIG. 17, and described further below. Control proceeds to 1512 to obtain a list of decision maker prospects, including job title, skills, and career background details for the prospects. Control then preprocesses the obtained job title and career background data at 1516. An example method of preprocessing the obtained job title and career background data is illustrated in FIG. 18, and described further below.

Control proceeds to run the job title decision committee model at 1520, and also optionally runs the career background decision committee model at 1524. For example, control may run the job title decision committee model to generate a title score output indicative of a likelihood that the contact entity is a decision entity according to structured title data associated with the contact entity, and may run the career background decision committee model to generate a background score output is indicative of a likelihood that the contact entity is a decision entity according to structured background data associated with the contact entity.

Figure 19:
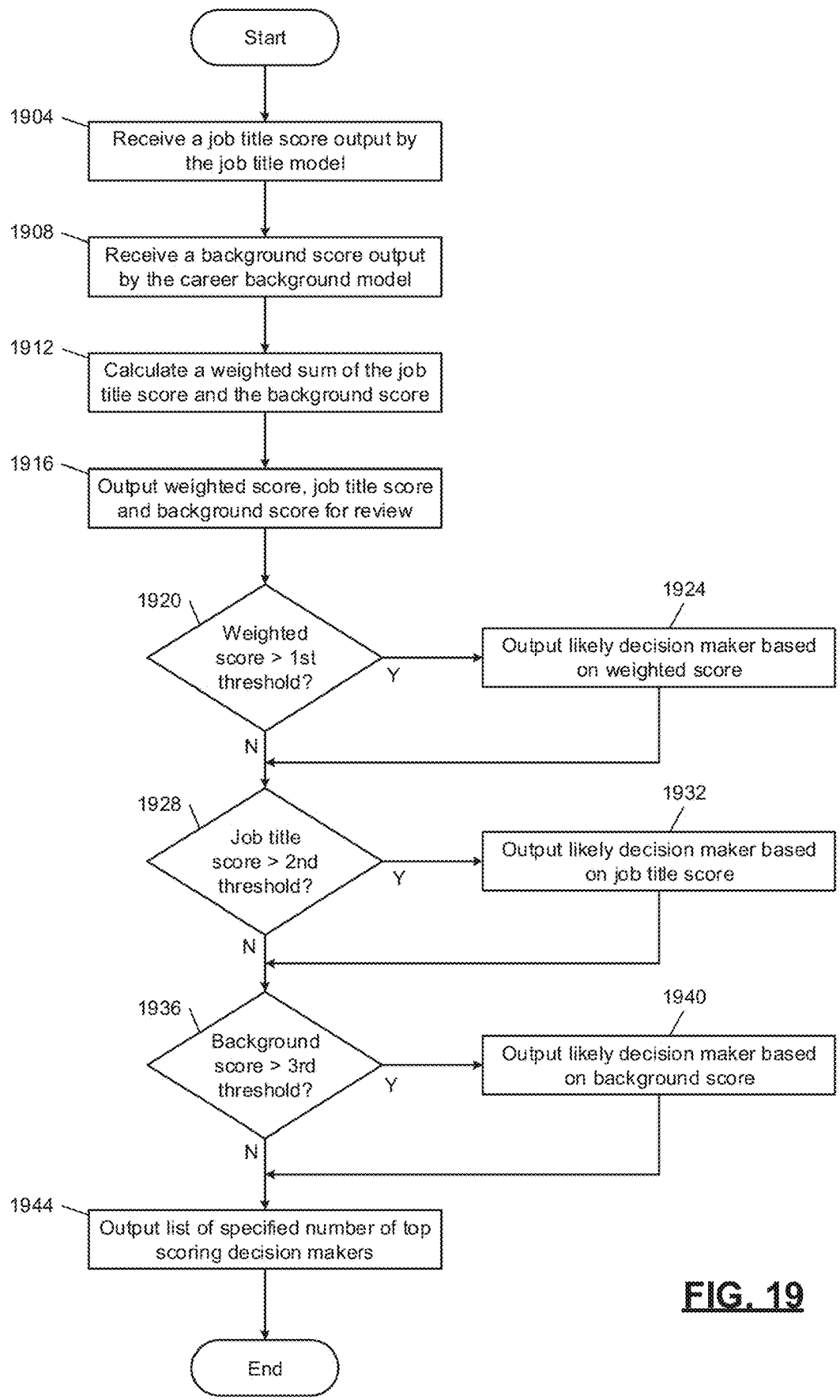
FIG. 19 is a flowchart depicting an example method of combining prediction outputs of the job title and career background machine learning models of FIG. 15.

The output scores from the job title model and the career background model are combined at 1528, to determine likely decision makers for a company. For example, the background score output and the title score output may be combined to determine a decision score output. An example process for combining the output scores is illustrated in FIG. 19, and described further below. Control then generates a decision committee list based on the output scores at 1532.

For example, two layers of model may be developed and the weighted average of the two scores may be generated as the output. A first model may take keywords or a word embedding vector from the title as input and generate a "title score" based solely on job title of the prospect, and a second model may include the remaining variables for "background score" generation. The two scores may be weighed and combined as a final model score for management's review. Each score may have any suitable range, such as 0-1, where a higher score may indicate a higher likelihood that the prospect is a decision maker or influencer.

FIG. 16 is a flowchart depicting an example method of training the job title machine learning model of FIG. 15. At 1604, control begins by obtaining historical records of contacted decision maker prospects to create a training dataset. Control proceeds to 1608 to obtain a job title of a first decision maker prospect. At 1612, control determines whether the prospect responded positively. For example, a positive response may occur where the prospect engaged a contact in order to purchase health coverage for employees of the prospect's company. If so, control flags the prospect as a decision maker at 1616. If not, control flags the prospect as an in-deterministic decision maker at 1620.

At 1628, control determines whether the last prospect in the dataset has been processed. If not, control obtains a job title for the next prospect at 1624, and then determines whether the prospect responded positively to a health plan contact at 1612. Once the last prospect in the dataset is reached at 1628, control proceeds to 1632 to duplicate decision maker records and down-sample in-deterministic decision maker records. For example, decision makers and in-deterministic decision makers may be unbalanced in the training data set, and records may be duplicated or down-sampled to obtain a more even balance for training purposes.

At 1636, control trains a variable selection model (such as a random forest model) on a job title matrix to determine the most relevant keywords. Control than selects a specified number of the top keywords at 1640, and trains a binary classification model (such as a multinomial naïve Bayes model) on the term frequency matrix of the top keywords, or word embedding vectors, at 1644.

FIG. 17 is a flowchart depicting an example method of training the career background machine learning model of FIG. 15. Control begins at 1704 by obtaining vendor records of career backgrounds of decision maker prospects. Control then obtains career background details of a first decision-maker prospect at 1708. Control determines at 1712 whether the career details suggest the prospect is a decision maker. For example, a long history of employment at a single company may suggest seniority, and that the prospect is in a management decision making role. If control determines at 1712 that the career details suggest the prospect is a decision maker, control flags the prospect as a decision-maker at 1716. Otherwise, control flags the prospect as a non-decision-maker at 1720.

At 1724, control determines whether the last prospect has been reached in the dataset. If not, control proceeds to 1728 to obtain career background details for the next prospect, and again determines whether the career details suggest the prospect is a decision maker, at 1712. Once the last prospect is reached at 1724, control proceeds to 1732 to duplicate the decision maker records and down-sample in-deterministic decision maker records. As mentioned above, the decision maker and in-deterministic decision maker records may be unbalanced, and making adjustments through duplication and down-sampling may even the datasets for training the model.

At 1736, control supplies career background details and a skill word to a binary classification model (such as a light gradient boosting model). Control then trains the model to classify a prospect as a decision maker or an in-deterministic decision maker, based on the career background data, at 1740.

FIG. 18 is a flowchart depicting an example method of preprocessing input data for the job title and skill machine learning models of FIG. 15. Control begins at 1804 by transforming job function and seniority data from a string type to a category type. At 1808, control determines whether a prospect has more than 52 years of service (or any other suitable threshold time period that suggests the prospect is not currently working for the company). If so, control flags the job seniority data as retired or erroneous at 1812 (for example, because a prospect having more than 52 years of service is likely an error in the data or is likely retired).

Control then proceeds to 1816 to standardize the job title and career background data, according to text preprocessing rules. At 1820, control tokenizes standardized title text to create a job title term frequency matrix (or word-embedding vectors). At 1824, control tokenizes standardized career background text create a career background term frequency matrix (or word-embedding vectors). Control then merges the term frequency matrices (or word-embedding vectors) with the obtained list of decision maker prospects in order to run the model, at 1828.

As an example, the model may accept any datasets that include required variables. Datasets with different sets of variables may be mapped into the format of selected features (such as features provided by Netwise, Inc. or other external vendor web sources). Job function and seniority may be transformed from a string type to a category type. A years of service may not be considered if the prospect worked on that job for more than a threshold period of time (such as 52 years), because those prospects may be considered as retired, or there may be a typographical error in the position start year.

A standard set of text preprocessing steps may be adopted to transform the job title and skill. Example steps may include, but are not limited to, removing excessive blank spaces between words, standardizing words into lowercase, remove stop words, replacing common word mistakes, abbreviations and terms, removing numeric values, performing word segmentation, performing a spelling check, performing spelling correction, changing a part of speech, word stemming, word lemmatization, and word singularization.

After the text preprocessing steps, a standardized final title and career background may be generated, which may be unlike ordinary readable English. However, the standardized values may substantially reduce the amount of unique words, and also reduce uncaptured information due to human errors or abbreviation. The standardized title and career background text may be tokenized to create a term-frequency matrix, or transformed as word-embedding vector. A term frequency matrix is a common format that allows a computer to read and understand the presence of words in a sentence. For each row of a sentence, each unique word would have a number that represents the count of terms in the sentence. A word-embedding vector may include a numerical representation of a sentence, as transformed by a word-embedding model that has been trained with various documents.

FIG. 19 is a flowchart depicting an example method of combining prediction outputs of the job title and skill machine learning models of FIG. 15. Control begins at 1904 by receiving a job title score output from the job title model, and receiving a skill score output by the career background model at 1908. At 1912, control calculates a weighted sum of the job title score and the skill score.

Control proceeds to 1916 to output the weighted score, job title score, and skill score (for example, to be reviewed by an administrator). At 1920, control determines whether the weighted score (such as a weighted sum) is greater the first threshold. If so, control outputs a likely decision maker indication based on the weighted score, at 1924. In this case, the weighted sum of the job title score combined with the skill score may indicate that the prospect is likely a decision maker according to an overall balance of the job title and career background of the prospect.

At 1928, control determines whether the job title score is greater than a second threshold. For example, the second threshold used at 1928 may be different than the first threshold used at 1920 with respect to the weighted score. If control determines at 1928 that the job title score was greater than the second threshold, control outputs a likely decision maker indication based on the job title score, at 1932. In this case, control may determine that the prospect is a likely decision maker based on job title alone (for example, if the job title is HR manager or another title indicative that the prospect likely plays a large role in selecting a health plan for a company).

At 1936, control determines whether a skill score is greater than a third threshold (which may be different than the first and second threshold described at 1920 and 1928). If control determines at 1936 that the skill score is greater than the third threshold, control outputs a likely decision maker indication based on the skill score, at 1940. In this case, control may determine that the skill score strongly indicates that the prospect is a likely decision maker, without consideration of the job title. At 1944, control outputs a list of a specified number of the top score decision makers (such as the top scoring decision maker, the top three scoring decision makers, the top ten scoring decision makers, etc.).

As described above, each of the two model scores may be used to evaluate the likelihood of a prospect being a decision maker. If either score is high (such as above a target threshold value), it may be more likely that the prospect is a decision maker or influencer. A weighted sum of the two scores may be calculated in various implementations, so that if either score is high, the weighted score will trend towards the higher score. Equations (1)-(3) below provide examples of calculating a weighted score using the individual scores from the first layer model (such as the job title model) and the second layer model (such as the career background model).

$$\text{Ratio} = \frac{\text{score}_{1st\ layer\ model}}{\text{score}_{2nd\ layer\ model}} \quad \text{Equation (1)}$$

$$\text{weight} = \begin{cases} [1 + e^{-ratio+2}]^{-1}, \text{ratio} > 2 \\ 0.5, 0.5 \le \text{ratio} \le 2 \\ 1 - [1 + e^{-\frac{1}{ratio}+2}]^{-1}, \text{ratio} < 0.5 \end{cases} \quad \text{Equation (2)}$$

$$\text{weighed score} = \quad \text{Equation (3)}$$
$$\text{weight} \times \text{score}_{1st\ layer\ model} + (1 - \text{weight}) \times \text{score}_{2nd\ layer\ model}$$

The weighed score may be plugged into a script, which may select a list of a desired number of decision makers having the highest score for each company. Management may provide a criteria list as an input to specify the minimum number or proportion of decision makers that satisfy the criteria. The model may be used to identify high potential individuals that are more likely to be decision makers or influencers for selecting corporate health care plans. In various implementations, the company decision maker model may be used with a household decision maker model (such as the models described in FIGS. 20-22), in order to predict an individual in a household that is likely to be the decision maker for selecting a health plan for members of the household.

In various implementations, the decision maker prediction model may be packaged as a Docker container. The image may be deployed to a company cloud infrastructure in the scoring process. A contact list will be collected from a data store (such as a Data Lake) and loaded into the container. Text information such as title and career background will be preprocessed by a script, and transformed into term frequency matrices (or word-embedding vectors). The two matrices may be merged into the original contact list and fed into two models.

The two models will generate their own model scores. A weighting function may be applied to calculate a weighed score. A marketing team may then review the score and select the records with having the highest weighed score as a decision committee (for example, a number of individuals at a company that are most likely to be decision makers regarding employer-sponsored health plans of the company). For a discrete case, a manager may provide a criteria list to form a decision committee with specific criteria, such as maintaining a distribution of job function and seniority as desired, based on the output.

In order to select potential prospects that make the company health plan decisions or assist in the decision making process, a list of previously approached prospects in historical records may be adopted as training data. The data source contains a history of marketing activity to the prospects, and whether the prospect responds with positive feedback (for example, whether the prospect considers having the company purchase a health plan). The information is used to generate target labels of "Decision Maker" and "In-deterministic decision maker" for the model training process. A first layer model may be trained using the title and decision maker flag.

A common challenges in applying data analytics in business is that target label distribution is highly imbalanced. In order to facilitate the initial model building, decision maker records may be duplicated into, for example, three folds of the original size, and one-third of the in-deterministic decision maker records may be sampled. After resampling, a rate of decision maker records may be increased (for example, to 32% or more or less).

Before performing the model training, a variable selection model may be trained on the matrix to discover keywords with high importance. This may further reduce the complexity and computation time of the model, by dropping keywords with low importance. After the feature selection, a specified number of keyword tokens may be retained (such as the top 523 keyword tokens, or more or less).

A binary classification model (such as a multinomial naïve Bayes model) may be adopted to train the first layer model with the term frequency matrix (or word-embedding vectors). It is a probabilistic model based on the naïve Bayes' theorem, with strong independence assumptions between features. It is a popular model for text classification. With the first layer model, different levels of positive and negative effects of keywords may be estimated. In various implementations, other binary classification models may be used.

Some of the titles do not retrieve sufficient information regarding a prospect's job nature and experience. A prospect's background, such as career background and job duration, may not be available in the historical dataset. In order to leverage the information in the decision committee selection, a dataset related to the career background of prospects may be purchased from an external vendor, and used in the model building process for a second layer model. A marketing team may review a subset of a data source and generate labels for modeling. Resampling maybe performed to balance the sample size of the decision maker and the in-deterministic decision maker records. The decision maker records may be duplicated into, for example, six folds, and one-third of the in-deterministic decision maker records may be sampled without replacement, to raise the rate of decision maker records to 35.5% (or more or less).

A second layer model may account for career background details of a prospect, including a job function, a seniority, years of experience at the current position, a term frequency table of career background (or word-embedding vectors), etc. A binary classification model, such as a light gradient boosting model, may be used to build up the second layer model. A gradient boosting model is a tree-based model which improves the ability of model fitting, by finding a gradient of the error. It may be adopted for its efficiency, and generally provides good prediction on classification tasks. The models may be regularly retrained when a campaign result is available, which provides updated and objective information about a decision committee, in order to improve model performance in a progressive manner.

In various implementations, the decision maker prediction models may fuse traditional numerical and categorical features used in business modeling, with text processing of career background information. The two component models complement with each other, and may provide additional performance that one model alone may not provide. Consideration of text information also avoids human bias during creation of a target list. While a human resource manager and chief-level leadership team may often be considered as the ordinal and reasonable person to approach, the model may consider other special keywords that reveal their focus in medical benefit plan selection, without worrying about missing keywords reasoned from differences in grammar.

In various implementations, the model may reduce the workload of marketing teams by automating a majority of the marketing team's target list creation. Under a traditional approach, marketing managers may search a contact database using specified criteria which, even after totally unrelated contacts are screened out, may produce a long list with similar titles. The consideration of career background and description of focus in title may help prioritize contacts under the same job function and seniority, and the marketing team may focus more on campaign design and execution. Various implementations may use the models to find decision maker and influencer prospects by leveraging unstructured text information such as title and career background.

Individual Decision Maker Model

Figure 20:
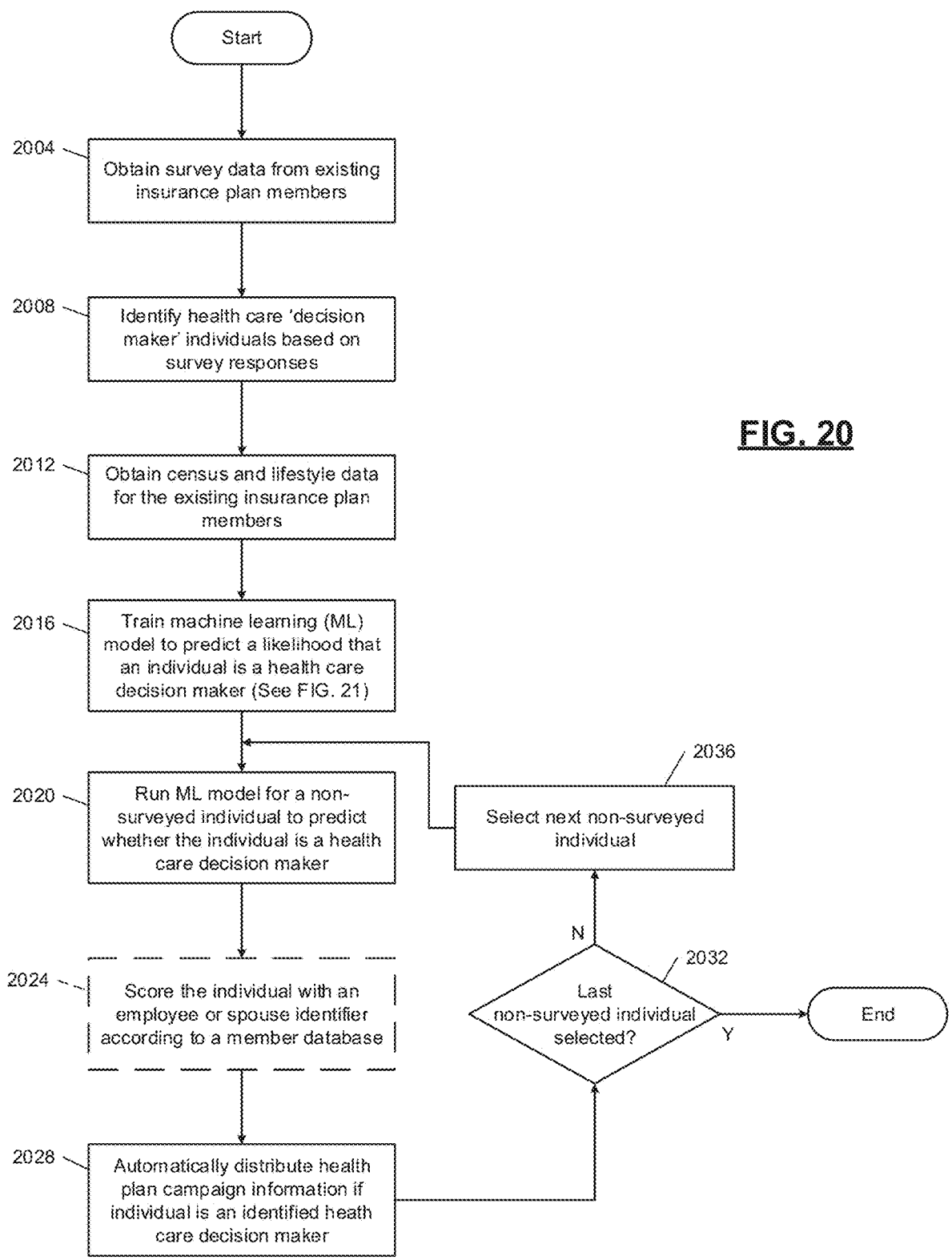
FIG. 20 is a flowchart depicting an example method of implementing a machine learning model for generation of a household decision maker prediction output.

FIG. 20 illustrates an example process for generating a machine learning model for predicting whether an individual is a health plan decision maker for a household. At 2004, control begins by obtaining survey data from existing insurance plan members. For example, existing insurance plan members may be periodically prompted to provide feedback about their health plan experiences via surveys, such as a transactional survey (for example, t-NPS) that occurs each time an individual uses a health plan benefit or otherwise interacts with the health plan, or an enterprise survey (for example, e-NPS) that is sent out on a periodic (such as yearly) basis.

At 2008, control identifies a health care 'decision maker' individual based on the survey responses. For example, the surveys may include specific questions about whether the individual makes health plan or health care decisions for the family, or the surveys may include indirect questions that are indicative of whether the individual makes health plan or health care decisions for the family and indirect question responses may be scored to determine whether the individual is a decision maker.

Control obtains census and lifestyle data for the existing insurance plan members at 2012. For example, one or more databases may be accessed to obtain parameters and characteristic of each individual for multiple variables, such as an Acxiom database. These characteristics can be used as independent variables or predictors to build the machine learning model.

The machine learning model is trained at 2016, to predict a likelihood that an individual is a health care decision maker. For example, a dependent variable may be set as one if an individual is a decision maker, and a dependent variable may be set as zero if an individual is not a decision maker. An example process for training the model is illustrated in FIG. 21, and described further below.

During training of the model at 2016, any suitable machine learning technique(s) may be used to classify the census and lifestyle data corresponding to the decision maker and in-deterministic decision maker individuals, to process the data, etc., including random forest models and logistic regression models. Probability estimation may be used to determine scores for each of the records that describe whether or not an individual is a decision maker.

Control runs the model at 2020 for a non-surveyed individual, to predict whether the individual is a health care decision maker. For example, control may run the model to generate decision score output is indicative of a likelihood that the individual entity is a decision entity in a household group that includes the individual entity.

At 2024, the individual is optionally scored with an employee or spouse identifier according to a member database, such as the member data 110 of the database 102 in FIG. 1. For example, if the individual is a current member of an employer-sponsored health plan and is identified as a decision maker, the individual may be scored as the employee receiving the plan or a spouse of the employee receiving the plan.

Health plan campaign information is automatically distributed at 2028 if the individual is predicted to be the decision maker for the household. For example, the decision score output may be compared to a threshold value, to selectively include the individual in a subset of individuals that will receive automatically distributed structured campaign data.

This may include any suitable automated process for generating emails, social media advertisements, digital advertisement purchases, entertainment content streaming advertisements, etc., that target the predicted decision maker. Because the predicted decision makers are known to have a higher likelihood of deciding which health plan to use or which benefits to use, the predicted decision makers are expected to have a higher response rate for targeted health plan campaign information.

At 2032, control determines whether the last non-surveyed individual has been selected. If so, the process ends. If more non-surveyed individuals still have not been selected, control proceeds to select the next non-surveyed individual at 2036, and repeats running the model to predict whether the next non-surveyed individual is a decision maker at 2020.

While developing the model, a system administrator may use any suitable techniques for understanding the available feature space and finding patterns by plotting, creating charts, using descriptive statistical techniques, etc. The data acquired may be a large sample, with more than 1500 variables is some cases. Preprocessing steps may be used to clean data prior to training the model or using the model, including column renaming, scaling numerical variables, encoding categorical variables, binning, creating dummies, dropping variables which are determined to not have sufficient significance, handling different data types, imputing values, and creating training and test samples.

Optimized machine learning modelling techniques may be used to choose the best models, and hyper-parameters may be tuned while considering impacts on performance, accuracy, bias, and variance of the model, including evaluation by calculating and plotting a gains-lift chart. Both local and cloud platforms could be used per data size and business requirements. Once the model is ready, the model may be used to score for different campaigns, including both acquisition and retention campaigns.

In some implementations, the target audience of the model is identified individuals who make decisions related to health insurance in the household. Once the audience is identified correctly, a campaign may be directed so that only the decision makers, and not other members in the household, receive the campaign information.

FIG. 21 is a flowchart depicting an example method of training the machine learning model of FIG. 20. At 2104, control begins by obtaining healthcare decision maker survey data for multiple individuals. Control then oversamples or undersamples the obtained survey data to adjust a ratio of identified decision makers individuals and in-deterministic decision maker individuals, at 2108.

At 2112, control performs a bivariate analysis to determine the association between dependent and independent survey data predictor variables. Control then proceeds to group the variables according to determined weight of evidence (WOE) values, to create binary dummy variables for categorical and numerical inputs, at 2116.

Control trains a machine learning model at 2120 using the grouped variables, to generate decision maker likelihood scores. At 2124, control performs post-processing on the output of the machine learning model to store the output scores and decile groups.

Figure 22:
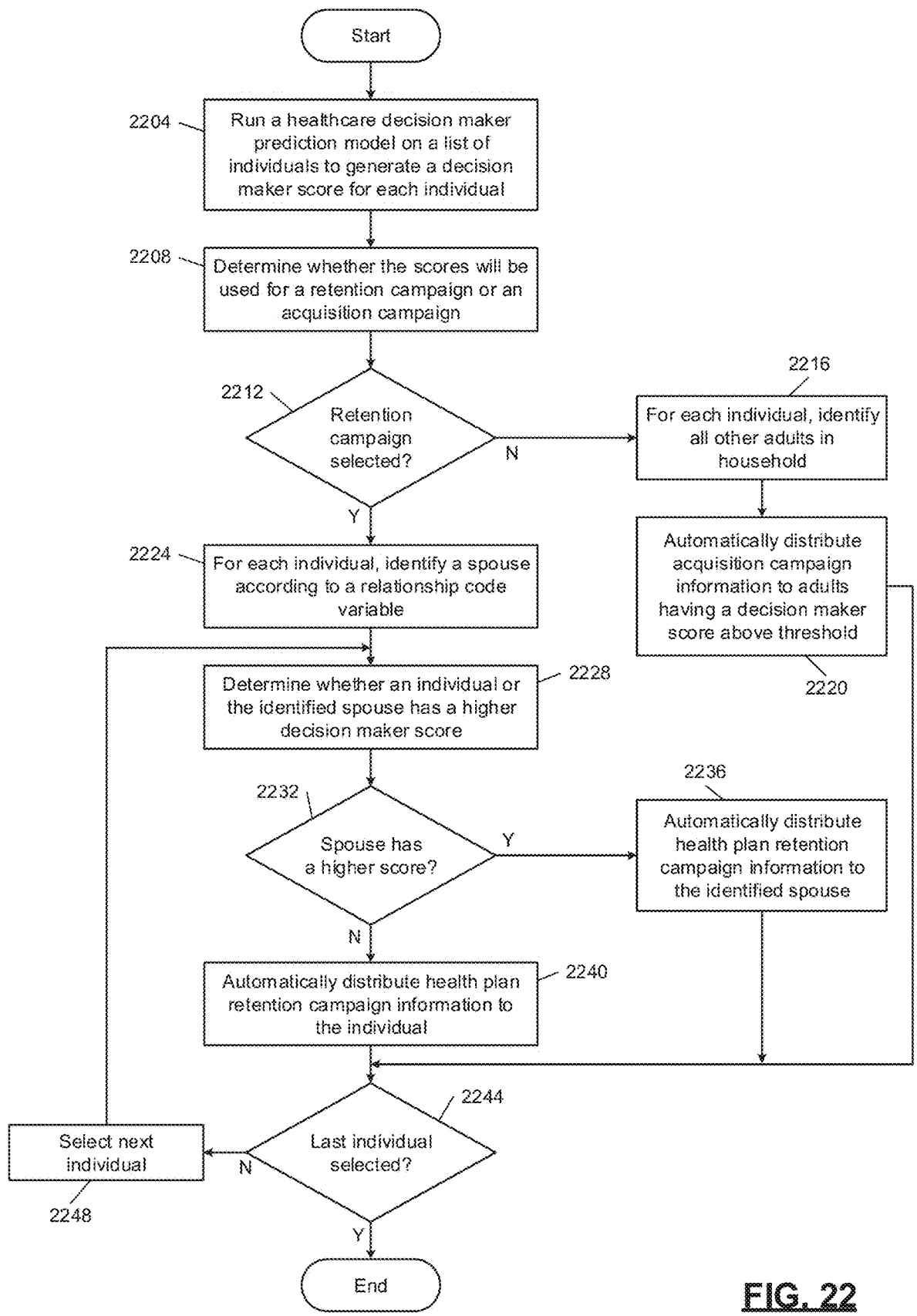
FIG. 22 is a flowchart depicting an example method of automatically distributing retention or acquisition health plan campaign information according to prediction outputs of the machine learning model of FIG. 20.

FIG. 22 is a flowchart depicting an example method of automatically distributing retention or acquisition health plan campaign information according to prediction outputs of the machine learning model of FIG. 20. Control begins at 2204 by running a healthcare decision maker prediction model on a list of individuals, to generate a decision maker score for each individual. Control then proceeds to 2208 to determine whether the scores will be used for a retention campaign or an acquisition campaign.

At 2212, control determines whether a retention campaign has been selected. If not, control proceeds to 2216 to, for each individual, identify all other adults in the household. At 2220, control automatically distributes acquisition campaign information to adults having a decision maker score above a threshold (for example, control may distribute campaign information to all adults in the household that are indicated as likely to make decisions about health plan purchases for the household).

If control determines at 2212 that a retention campaign is not selected, control proceeds to 2224 to, for each individual, identify a spouse of the individual according to a relationship code variable. At 2228, control determines whether an individual or the identified spouse of the individual has a higher decision maker score. If control determines at 2232 that the spouse has a higher score, control proceeds to 2236 to automatically distribute health plan retention campaign information to the identified spouse.

If control determines at 2232 that the spouse does not have a higher score, control automatically distributes acquisition campaign information to the individual at 2240. At 2244, control determines whether the last individual has been selected. If not, control proceeds to 2248 to select the next individual and then returns to 2228 to determine whether the individual or the identified spouse of the individual has a higher decision maker score. Once the last individual selected at 2244, the process ends.

In various implementations, the household decision maker models may identify a member of a household (such as an employee of a company or the employee's spouse), that is most likely to make healthcare decisions for the family. For example, the household decision maker's responsibilities may include choosing what type of health insurance to buy, choosing doctors and hospitals, working with insurance companies on getting pre-approval for procedures, and reviewing claims or bill amounts. The household decision maker model may be used to target identified household decision makers using acquisition and/or retention campaigns.

Creating an input for the household decision maker model may include first creating a dependent variable, such as e-NPS survey results. The survey results file may be merged with census and lifestyle data (such as a YLM file). In various implementations, positive responses for specific questions may be used to identify household decision makers. For example, individuals may be asked survey questions about the role that they play in making important decisions about their family's health insurance, where responses of being the main decision maker are scored higher than responses of being less involved or uninvolved in the decision making process.

Some models may use two layers before reading a final stage of implementation. For example, a first output may include a probability score from the model that predicts a likelihood of an individual to be the decision maker for their family. A higher magnitude score is indicative of an increased likelihood that the individual is a decision maker for their household.

Next, scored individuals may be rolled up to family levels according to household identifiers. The individuals may be identified as employee and spouse (for example, when focusing on a retention campaign), or the individuals may be identified as married couples (for example, for an acquisition campaign). The decision maker may be identified for each household. If both individuals in a married couple have high scores, both may be targeted with a health plan campaign. In other cases, only the highest scoring family member may be targeted to receive a campaign.

In various implementations, model data may include individual-level data, with a member ID or individual enterprise ID used as a unique identifier for each row. Survey responses may be used to create decision maker and in-deterministic decision maker labels for each individual in the data. The survey data may include a bias towards decision makers, because decision makers may be more likely to respond to the survey. Therefore, the ratio in the survey data may not reflect the ratio in the actual population. The sample bias may be addressed by assuming a training data ratio that is closer to the actual population ratio, by adding more in-deterministic decision maker data to the training data. The data may be oversampled or undersampled accordingly to address an unbalanced distribution.

In various implementations, predictor variables may be transformed into binary dummy variables, for categorical and/or numerical inputs. A bivariate analysis may be performed to determine a relationship or association between a dependent variable (decision maker or in-deterministic decision maker), and each of the independent predictor variables (for example, from a YLM 1700 file). In this example, an individual identified as a decision maker may be considered as a non-event and assigned a score of 1, while an individual identified as an in-deterministic decision maker is considered as an event and assigned a score of 0.

A weights of evidence (WOE) value and a marginal information value (IV) may be used to combine variable groups and levels, respectively, using a process called coarse classing and fine classing. The IV for each variable may indicated a predictive power of the variable. Based on the WOE values, variable levels may be grouped together to create dummy variables. Combining variable levels or groups may be an implementation of coarse classing. These dummy variables may then be used in the model to predict a dependent variable. Multiple dummy variables can be created from one predictor based on the partial information value of each class and the predictive power of the variable. Model variables may be fine-class binned using the WOE and IV, in conjunction with Python programming.

In various implementations, a selected audience (such as a list of individuals likely to work at a specific company as determined by the models of FIGS. 7-10), may each be scored by the household decision maker model to receive a probability score (for example, ranging from 0 to 1) that predicts a likelihood that an individual is a decision maker for the household. Higher scores may be indicative of a higher likelihood of being the decision maker.

The scores will be placed into ten deciles by ranking the probability scores. Smaller or top deciles (for example, deciles 1-4) may suggest a higher likelihood that an individual is not a decision maker for the household. After scoring every individual, the individuals may be rolled up to family level or household level. Each household may have at least one identified decision maker. An objective may be to send campaign information only to the individual(s) of the household that have the highest decision maker likelihood score, compared to other members of the household.

In various implementations, the model may be packaged as a Docker container. The image may be deployed to a company cloud infrastructure in the scoring process. Successful implementation of the model will reduce a target campaign population sizably, by targeting only the key decision maker individuals for each household and not necessarily sending multiple campaign advertisements to the same household.

For retention campaigns, the model may identify individuals that are employees (for example, individuals that can buy insurance through their employers), and individuals that are spouses (for example, according to a relationship code variable. Data may be rolled up to a household level to identify members of the household as employees or spouses, and identify the higher decision maker score individual to try and influence that person of the married couple.

For acquisition campaigns, the model may identify employees using an employer prediction model (such as the models described in FIGS. 7-10). In other cases, data may be rolled up to the household level to identify a married couple, at least one of which is working. The model may then compare scores to determine a decision maker among family members for sending targeted campaign materials. In various implementations, household members that are not an employee or spouse may also be scored, while some family members such as children are excluded.

The model may be trained by receiving e-NPS survey where at least one question is marked as determining whether an individual is a decision maker. Reponses may be combined to create events and non-events. After appending the events and non-events, the data may be merged with demographic data, such as a YLM 1700 file, to gather all the demographic information available for working individuals in the United States. Some observations or records may be lost where it is not possible to match the observations with third-party databases.

After the data was created a random selection (such as 70%) of the sample may be used for training data. The remaining 30% of the data may be used as a validation or test sample. Because the training and testing samples are completely independent of one another, based on the sample collection procedure, this may be considered as cross-validation. In various implementations, out-sample validation may be performed based on different timelines of a campaign, to ensure more stability and robustness.

In various implementations, any suitable classification algorithm may be used for the model, such as the XGBoost algorithm. For example, the XGBoost algorithm may provide improved lift and stability compared to other model algorithms. Hyper-parameters may be tuned to reduce overfitting, and stabilize the model.

The XGBoost algorithm may classify each company into one of multiple classes uniquely, depending on certain features of the company. For example, the gradient boosting technique may train a series of weak classifiers to build a strong classifier at the end, by accumulating the error in every classifier and rectifying or focusing more on them in the next classifier. Because this may be a black-box model which does not facilitate an understanding of how each of the predictors interact with the data, a generalized linear model (such as logistic regression) may be used to identify the direction of a relationship of every predictor with the dependent variable (according to the sign of the estimator), and the magnitude or strength of the relationship (according to the absolute value of the estimator). In other implementations, any modeling technique or any set of features may be selected or changed in various generations of the model.

The household decision maker model may create a dependent variable according to a sample survey, where it would be otherwise difficult to obtain the decision maker identifiers. The model may use numerical and categorical features of business models, with machine learning techniques, to achieve increased accuracy and stability.

Avoidable Er Visit Prediction Model

Figure 23:
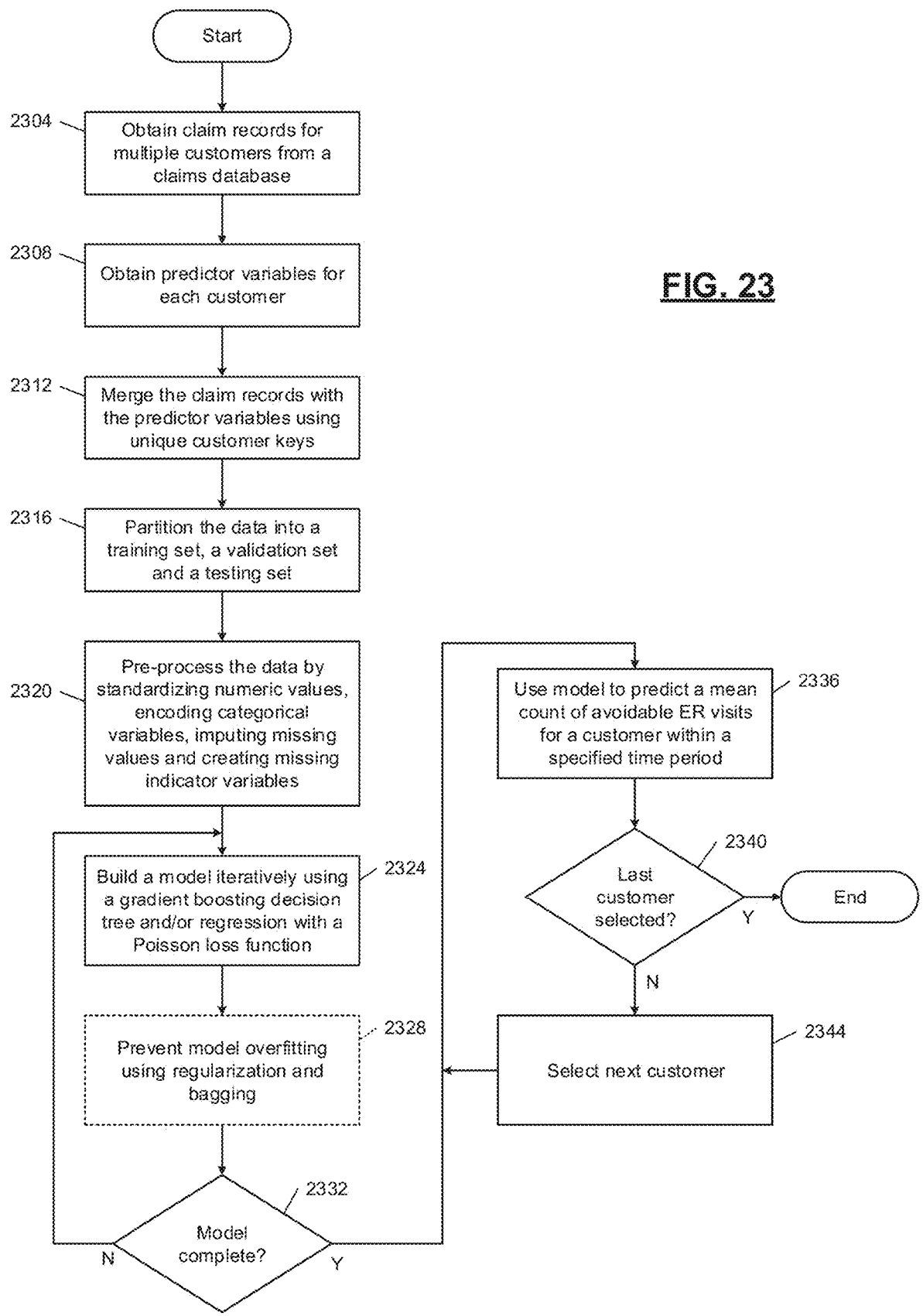
FIG. 23 is a flowchart depicting an example method of implementing a machine learning model for generation of an avoidable ER visit prediction output.

FIG. 23 illustrates a process for generating a machine learning model for predicting an avoidable emergency room (ER) visit. Control begins at 2304 by obtaining claim records for multiple customers from a claims database, such as the claims data 112 of the database 102 in FIG. 1. At 2308, control obtains predictor variables for each customer.

The obtained claim records are merged with the predictor variables using unique customer keys at 2312, and the data is partitioned at 2316. For example, the merged claim records and predictor keys may be partitioned into a training set, a validation set, and a testing set.

At 2320, control preprocesses the data to prepare it for building the model. For example, the data may be standardized using numeric values, the data may be encoded using categorical variables, missing values may be imputed, missing indicator variables may be created, etc.

The model is built iteratively at 2324, which may include using a gradient boosting decision tree, regression with a Poisson loss function, etc. At 2328, control optionally prevents model overfitting by implementing regularization and bagging. If the model is not yet complete at 2332, control returns to 2324 to continue iteratively building the model.

If the model is complete at 2332, control proceeds to 2336 to use the model to predict a mean count of avoidable ER visits for a customer, patient, etc., within a specified time period (for example, within the next three months, within the next year, etc.). In various implementations, control may use the model to generate a likelihood output indicative of a likelihood that the customer entity will have an avoidable negative health event (such as an ER visit) within a specified first time period. If a last customer has been selected at 2340, the process ends. If not, a next customer is selected at 2344, and control proceeds to 2336 to predict a mean count of avoidable ER visits for the next customer.

For customer acquisition in marketing campaigns, an insurance company typically only relies on available external data. Avoidable emergency room (ER) visit occurrences are not known until a person has already been admitted and a claim is generated. In order to investigate the relationship between avoidable ER visits and available external data sets, the example model generated in FIG. 23 may use a target variable of a count of avoidable ER visits for a customer in a specified time period (for example, a year), which can be aggregated from internal claim records for each customer. For model deployment, the predictor variables may come from externally available data (for example, data that does not require access to internal claim records of the insurer).

The target variable indicates a customer propensity to have avoidable ER visit(s). For example, if the count is one, it means that the customer has one avoidable ER visit in a year. If the count is equal to four, it means the customer has an avoidable ER visit on average every three months. The model outcome is the predicted mean count of avoidable ER visits for the customer in a specified time period (for example, a year). An insurance company may estimate the cost spent on a potential customer based on the predicted mean count multiplied by the mean ER cost.

Predictor variables may include customer information, household information, etc. As mentioned above, the predictor variables are merged with the target variable based on a unique customer key, and the data is then partitioned into training, validation and testing sets.

Data preprocessing (for example, standardization of numeric variables, encoding of categorical variables, imputation of missing values, and creation of missing indicator variables) may be performed on the training data, and applied to the validation and testing data. Standardization of numeric variables may be important if the scale of the data varies widely, and the model interpretation depends on the variable scale. Any suitable standardization techniques may be used. For example, if X is a numeric variable, an example statistically standardized variable is illustrated in Equation (4):

$$X' = \frac{X - \overline{X}}{s} \qquad \text{Equation (4)}$$

where $\overline{X}$ and S are the sample mean and the sample standard deviation of X in the training data. Alternatively, an example min-max normalized variable is illustrated in Equation (5):

$$X'' = \frac{X - \min X}{\max X - \min X} \qquad \text{Equation (5)}$$

where min X and max X are the minimum and the maximum of X in the training data. In case there are missing values in X, a missing indicator variable (for example, zero for non-missing values and one for missing values) may be created to keep track of the effect of missing values. They may then be imputed by the mean or median in the training data before or after the standardization.

Let Y be a categorical variable taking $k \in \{2,3, \ldots\}$ possible values $C_1, C_2, \ldots, C_k$ (including the category of a missing value). Depending on the model and implementation algorithm, k−1 indicator variable(s) may be created. Note that the base category may be any one of $C_1, C_2, \ldots, C_k$, when all the indicator variables take the value zero.

As mentioned above, a gradient boosting decision tree and/or regression with a Poisson loss function may be used to build the model iteratively, to take away variables that are not important or not statistically significant. Variables with too many categories can also be removed when the training error is much smaller than the validation error. Regularization (such as early stopping) and bagging may be used to prevent overfitting the model. Finally, a set of variables that are most important to predicting an avoidable ER visit count is chosen. Model building, variable selection and parameter tuning are carried out using training and validation data. For model interpretation, the Shapley value, importance and/or statistical significance of a variable can be utilized.

An emergency room visit typically is covered by health insurance companies. For patients covered by health insurance, an out-of-pocket cost is usually $50-$150 or more, and for patients without health insurance, the costs may be $150-$3,000+. With avoidable emergency room visits recently increasing, the expenditures of insurance companies on avoidable ER visits are also increasing. If the example model generated by the process in FIG. 23 could successfully reduce even one percent of avoidable ER visits, the total cost covered be the insurance company could be reduced significantly.

Predicting the exact time for each health plan customer to visit the emergency room is nearly impossible, due to the high noise of the target variable and uncertainty. A more feasible solution that helps solve the business problem is to predict the avoidable ER probability for an individual in the next few months, the upcoming year, etc. Campaigns and advertisements can be used to educate high probability members to focus on a healthier lifestyle, to inform them of other lower cost health care facilities, etc., in order to reduce insurance expenditures. A lower target probability may also imply a higher medical loss ratio (MLR), driving business decisions and revenue.

Models with different training data may be built for different short term and long term objectives. For example, in the short term, internal data can be used to predict the avoidable ER visits in the next quarter. However, these internal data are not available in the whole US population to drive acquisition strategy. External data may be used to predict the number of avoidable ER occurrences in the upcoming year, etc., to maximize the long term revenue and maintain a high profitable client base.

The model pipeline may start with loading and processing member data. A unique identifier is used to indicate each distinct entity, and the prediction will be generated for each unique key and required prediction timestamp. A binary target label may be generated to indicate an avoidable ER visit in the next three months.

Based on the correlation of variables and the avoidable ER indicator in the claim dataset, a likelihood score will be generated for the categorical dataset. Transactional data may then be aggregated into a single record for each entity, thereby representing a behaviour pattern of the entity.

Transformed data may be aggregated by mean and sum, per entity, so that it will represent the user characteristics. Additional data sources including encoded behavior data are joined to the member dataset. A preprocessing pipeline may clean and generate additional features, based on the characteristics of the features and the relationship with the target. Preprocessed data may be used as input to the model generated by the process of FIG. 23, etc.

Processed data may be passed to a gradient boosting algorithm, and bagging may be used to improve the model robustness. Bagging may refer to bootstrap aggregating.

Data can be sampled repeatedly, and in the training iterations some data may be ignored. A more stable result may be produced by reducing the overfitting effects of the model. In the training stage, a 5-fold cross validation can be used to tune the parameters, and to select features. A 5-fold cross validation may refer to the technique of splitting the data and refitting the model repeatedly. More data can be used for training and the consistency of the model can be measured.

In the prediction stage, the cleaned data may be passed to multiple models to generate a risk score. The risk score among all models may be averaged to produce a final result. Result averaging may reduce the reliance on one specific model, and may reduce the possibility of overfitting.

Figure 24:
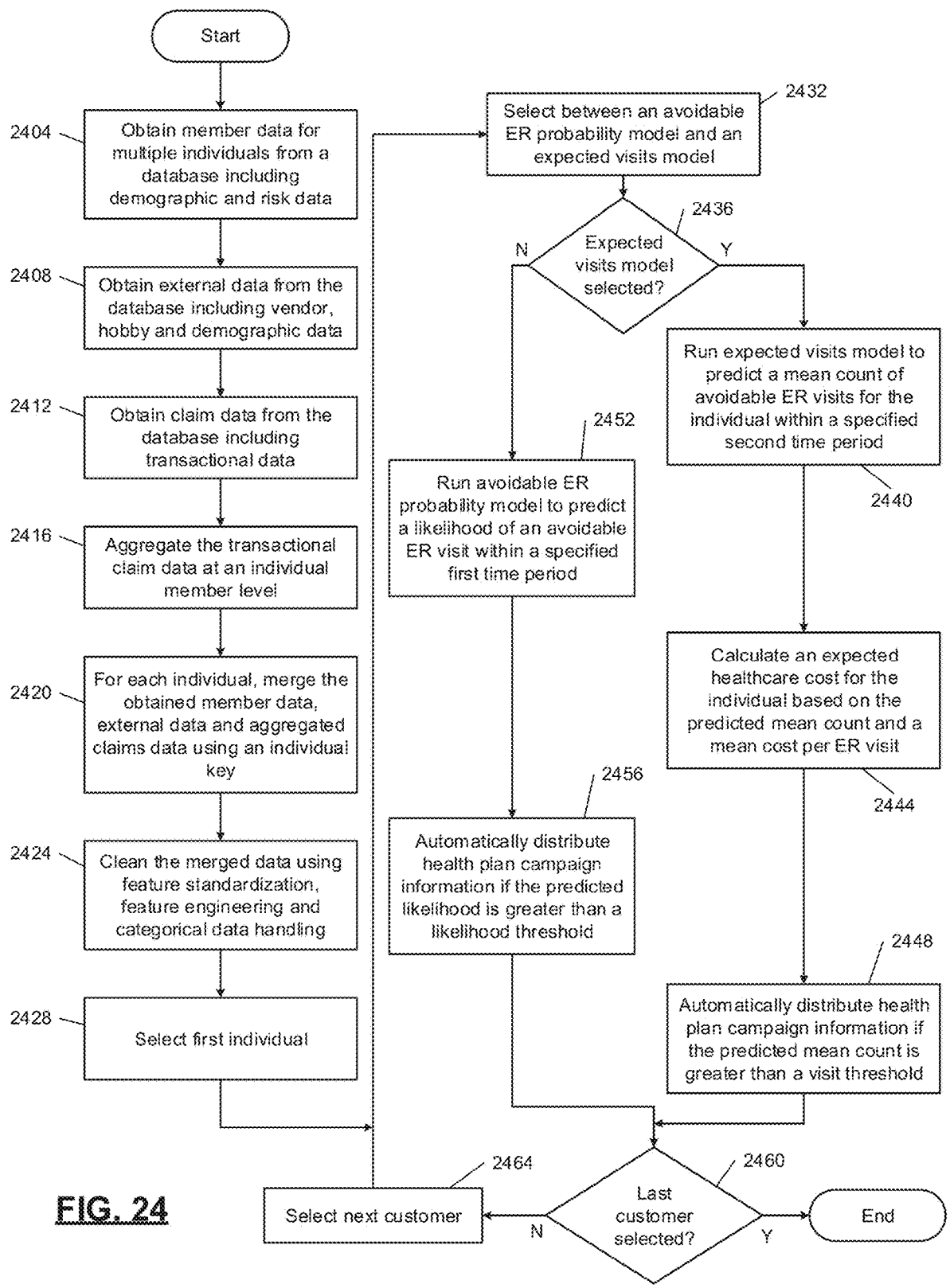
FIG. 24 is a flowchart depicting an example method of implementing an avoidable ER machine learning model for generation of an avoidable ER visit prediction output, and a mean ER visits machine learning model for generation of a mean ER visits prediction output.

FIG. 24 is a flowchart depicting an example method of implementing an avoidable ER machine learning model for generation of an avoidable ER visit prediction output, and a mean ER visits machine learning model for generation of a mean ER visits prediction output. Control begins at 2404 by obtaining member data for multiple individuals from a database, including demographic and risk data.

At 2408, control obtains external data from the database including structured vendor data, structured hobby data, and structured demographic data. Control then obtains claim data from the database, including transactional data, at 2412. Control proceeds to 2416 to aggregate the transactional claim data at an individual member level. At 2420, control merges the obtained member data, the external data, and the aggregate claims data, for each individual, using individual keys.

Control proceeds to 2424 to clean the merged data using feature standardization, feature engineering, and categorical data handling. At 2428, control selects the first individual. Control than selects between an avoidable ER probability model and an expected visits model, at 2432. For example, at 2436 control determines whether the expected visits model was selected. If so, control proceeds to 2440 to run the expected visits model to predict a mean count of avoidable ER visits for the individual, within a specified second time period (such as a year, or more or less).

Control then calculates an expected health care cost for the individual based on the predicted mean ER count, and a mean cost per ER visit, at 2444. At 2448, control automatically distributes health plan campaign information if the predicted mean ER count is greater than a mean count threshold value (such as more than one visit, more than three visits, etc.).

If control determines at 2436 that the expected ER visits models not selected, control proceeds to 2452 to run an avoidable ER probability model to predict the likelihood of an avoidable ER visit occurring for the individual within a specified first time period (such as a next three months, or more or less). In various implementations, control may run the ER probability model to generate a likelihood output indicative of a likelihood that the customer entity will have an avoidable negative health event (such as an ER visit) within a specified time period. Control automatically distributes the health plan campaign information if the likelihood of an avoidable ER visit is greater than a likelihood threshold value, at 2456. For example the likelihood threshold may be a 1% chance, a 15% chance, a 20% chance, etc.

At 2460, control determines whether the last customer has been selected. If not, control proceeds to 2464 to select the next customer, and then returns to 2432 to select between of avoidable ER probability model and an expected visits model. Once the last customer is selected at 2460, the process ends.

In various implementations, different target variables may be used for an expected ER visits count model, as compared to an avoidable ER visit likelihood model. The expected ER visits count model may predict a mean number of avoidable ER visits for an individual in the coming year (or any other suitable time period). For example, if the model output count is 1, it means that the individual may be expected to have one avoidable ER visit in a year. If the count is equal to 4, it means that the individual is expected to have an avoidable ER visit on average every three months.

Because the model outcome is an avoidable ER visit mean count in a year at a customer level, a company may estimate its cost spent on a potential customer by multiplying the predicted mean count with a mean ER cost. The two sets of targets can be interchanged by retraining the model, switching between a binary model and a regression model base on a business usage.

The model may take into account employee background details such as job function, seniority and number of years of service. Text information such as job title and career background information may also be considered. The model input may include any suitable variables, including but not limited to, an identifier such as a unique person identification number, claim data such as an aggregation of six months (or more or less) of claim history, and demographic data that represents the customer such as age or sex.

In a prediction stage, cleaned data may be passed to all of the models to generate a risk score. The risk score among all models may be averaged to produce a final result. Result averaging may reduce the reliance on any one specific model, and therefore reduce the chance of overfitting. Data may be stored in a Hadoop database or architecture, and extracted via an Impala module. The data may then be passed to a corporate server for use by an inference in Python. The output of the model may be populated back to the Hadoop database. The data in the population may be unbalanced. In order to improve the robustness of the model, the data may be sampled with different weighting. Higher weights may be applied to records with avoidable ER events.

The output of the model may include any suitable values, such as a unique person identification number, a model score that represents the probability of an avoidable ER visit within the next three months, and an expected visits model score that represents the predicted number of avoidable ER visits in the coming year (or a longer or short time period).

The model may use machine learning algorithms to accomplish a prediction task of predicting future avoidable emergency room (ER) visits. Both probability and the expected value can be modeled using the same framework. The model may be retrained easily due to the use of machine learning. Historical ER visits records and individual characteristics may be used to recognize a pattern of ER visits. Validation may be performed using a five-fold cross-validation scheme, which makes the algorithm more robust.

Retirement Model

Figure 26:
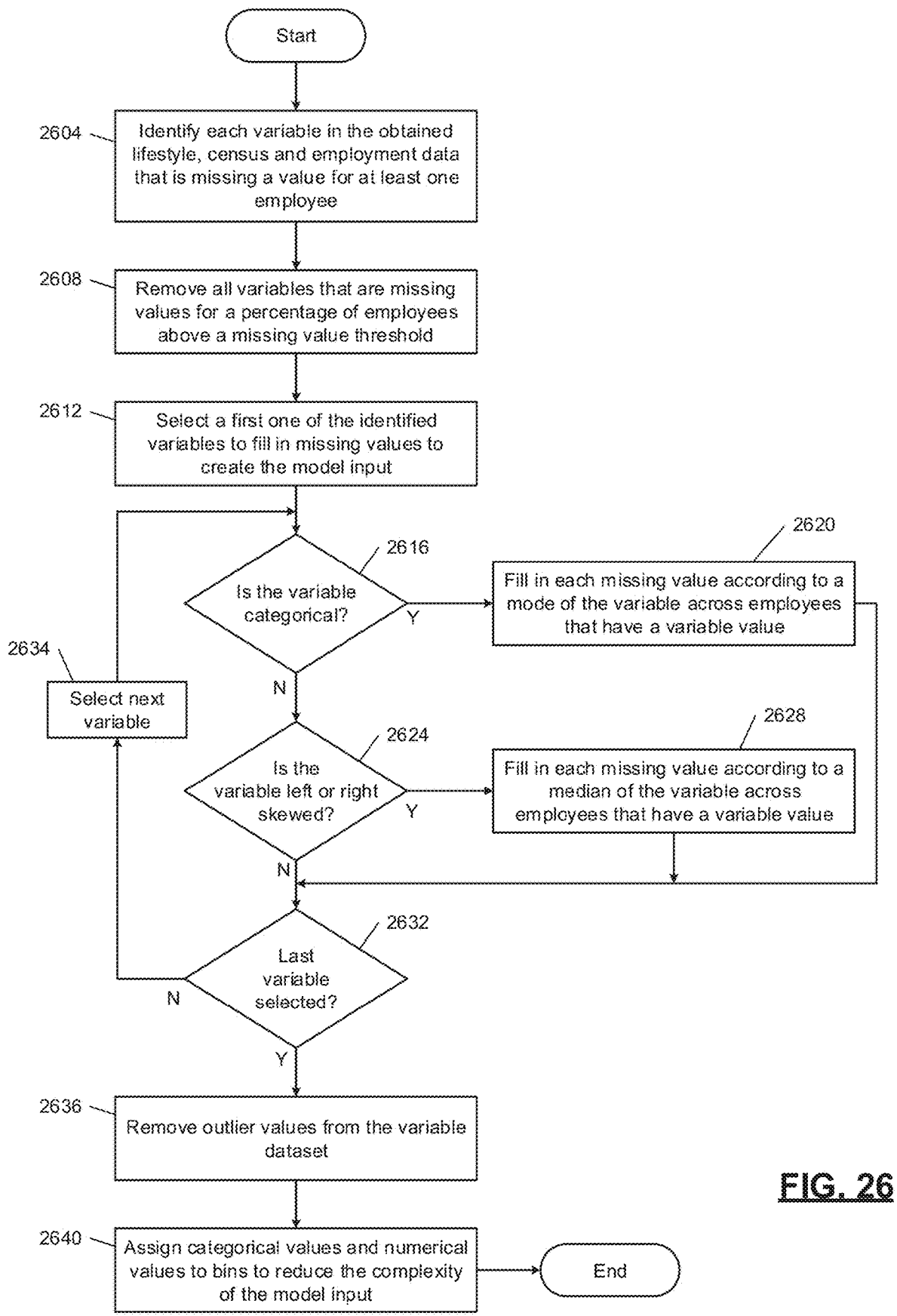
FIG. 26 is a flowchart depicting an example method of preprocessing training data for the machine learning model of FIG. 25.

FIG. 25 illustrates an example method for generating a machine learning model for predicting retirement and Medicare enrollment for an employee. At 2504, control begins by obtaining structured lifestyle data (for example, from a structured lifestyle database), structured census data (for example, from a structured census database), and structured employment data (for example, from a structured employment database), for multiple employees within a specified age range. Control preprocesses the obtained data at 2508, prior to suppling the data to a machine learning model. An example method for preprocessing the data is illustrated in FIG. 26 and described further below.

Figure 27:
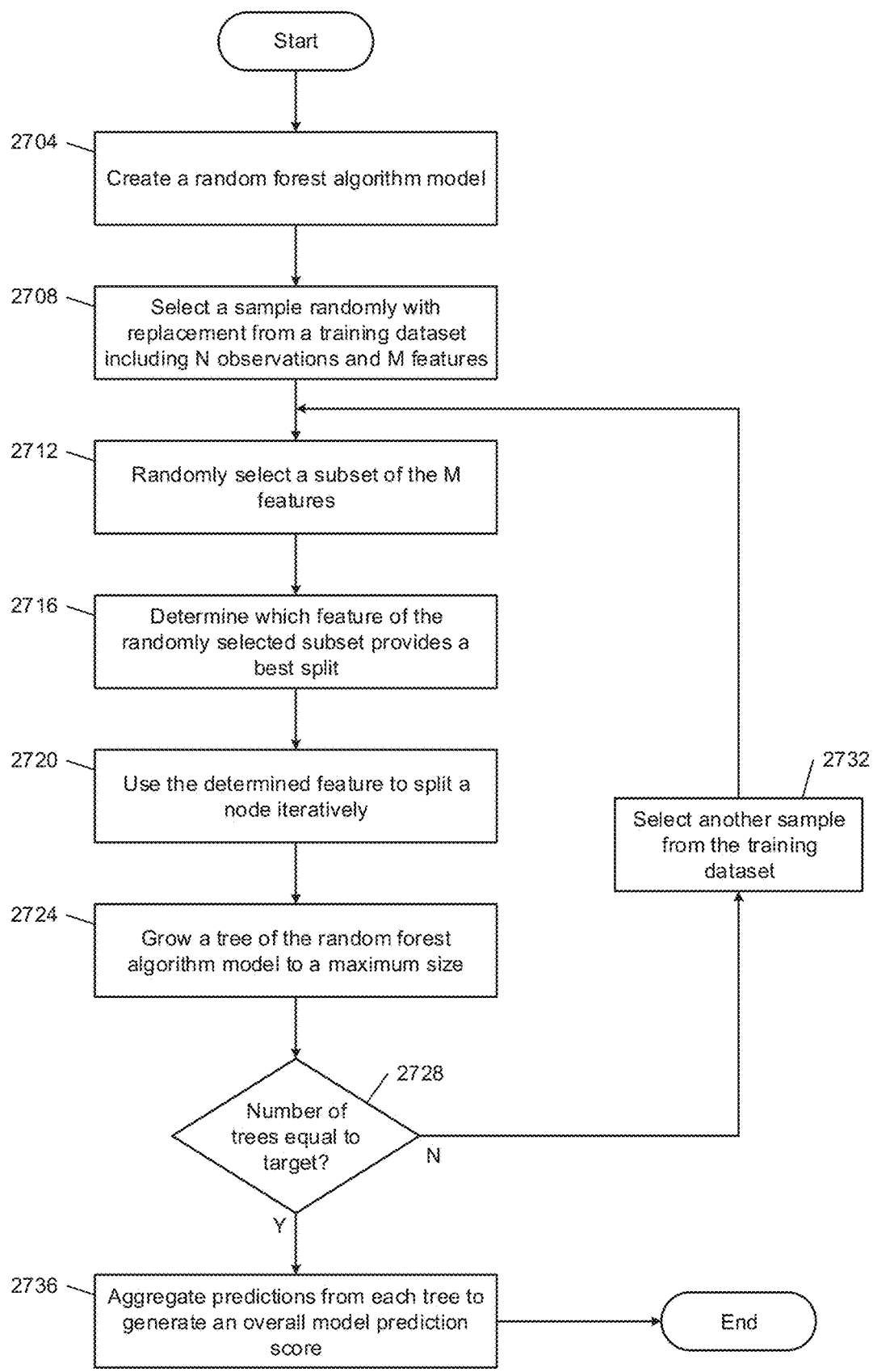
FIG. 27 is a flowchart depicting an example method of training the machine learning model of FIG. 25.

A machine learning model is developed at 2512 to predict the likelihood of each employee retiring on time (for example, at an expected retirement age such as 66) and enrolling in Medicare. In various implementations, the model may generate a retirement score output indicative of a predicted time period until the employee entity transitions to a retirement status. An example process for developing the machine learning model is illustrated in FIG. 27, and described further below.

At 2516, the machine learning model is used to rank order employees having the highest likelihoods of retiring on time. Control may use the model to, at 2520, predict an expected number of years until the employee retires (for example, when the employee does not have a high likelihood of retiring on time).

Employees may be sorted into age range bins at 2524, according to their predicted number of years until retirement and enrollment in Medicare. For example, there may be bins for 64-65, 66, 67, 68 or older, etc. In some implementations, the model may use an under 65 bin and a 65 or older bin (or any other suitable age for separating the bins into above and below).

At 2528, retirement health insurance information may be provided to each employee according to their predicted number of years of retirement. This may include any suitable automated process for generating emails, social media advertisements, digital advertisement purchases, entertainment content streaming advertisements, etc., that target the soon-to-retire employee. Because the predicted retirees have a higher likelihood of enrolling in Medicare, cheaper and more effective campaign may be implemented, to primarily target only soon-to-retire employees.

The retirement model is a predictive model that produces probability scores for every individual prospective customer that scored using the model. For example, the retirement model may predict the probability that the individual will retire and enroll in Medicare by the time they turn 66 years of age. Alternatively, or in addition, if this individual is not very likely to enroll in Medicare by the time they turn 66, the model may predict when they are most likely to retire (for example, by the age of 66, 67, 68, etc.).

These probability scores may be created using a combination of lifestyle, census, and employment data for individual prospective customers within the age range of 64-65 years old, etc. The probability scores are then used to rank order all of the prospective customers into deciles based on their probability to be "on time".

Once an individual has been scored relative to their likelihood of being on time, this output may be used as an input for a second round of scoring. For example, individuals who have been identified within the first three deciles may be labelled as "High Probability," and default to the output bin labelled 64-65. The remaining individuals may then be scored using another model trained to identify how many years late the individual will be. This model may cluster prospective customers, based on their characteristics, into buckets comprised of: one year late, two years late, three-plus years late, etc. These results can then be used to sort the target audience into different time tables for the purpose of our marketing campaigns (for example, marketing campaigns may only be sent to employees expected to retire and enroll in Medicare within the year, within the next year, etc.).

FIG. 26 is a flowchart depicting an example method of preprocessing training data for the machine learning model of FIG. 25. At 2604, control begins by identifying each variable in obtained lifestyle, census, and employment data, where the variable is missing a value for at least one employee. Control then removes all variables that are missing values for a percentage of employees above a missing value threshold, at 2608. For example, control may remove all variables that are missing values for at least 20% of employees, at least 50% of employees, at least 70% employees, etc.

At 2612, control selects a first one of the identified variables to fill in missing values, in order to create the model input. At 2616, control determines whether the selected variable is categorical. If so, control proceeds to 2620 to fill in each missing value (for example, each employee that does not have a value assigned for the variable), according to a mode of the variable across employees that have already assigned variable values.

If control determines at 2616 that the variable is not categorical, control proceeds to 2624 to determine whether the variable is left or right skewed. If so, control proceeds to 2628 to fill in each missing value according to a median of the variable across employees that already have a variable value assigned. At 2632, control determines whether the last variable has been selected. If so, control proceeds to 2634 to select the next variable, and returns to 2616 to determine whether the next selected variable is categorical.

If control determines at 2632 that the last variable has been selected, control proceeds to 2636 to remove outlier values from the variable dataset. At 2640, control assigns categorical values and numerical values to bins, in order to reduce the complexity of the model input.

FIG. 27 is a flowchart depicting an example method of training the machine learning model of FIG. 25. At 2704, control creates a random forest algorithm model. Control then selects a sample randomly with replacement from a training dataset including N observations and M features, at 2708. At 2712, control randomly selects a subset of the N features.

At 2716, control determines which one of the randomly selected subset of the M features provides the best split. Control then uses the determined feature to split the note iteratively, at 2720. At 2724, control grows a tree of the random forest algorithm model to a maximum size.

Control then determines, at 2728, whether a number of trees is equal to a target value. If not, control selects another sample from the training dataset at 2732, and returns to randomly select a subset of the M features at 2712. If control determines at 2728 that the number of trees is equal to the target value, control aggregates predictions from each tree to generate an overall model prediction score, at 2736

In various implementations, model data may be obtained from, for example, a YLM database that includes background information about users (such as how much a user spends, how many children a user has, and whether a user is a tech savvy or not). In various implementations, more than 1500 variables (or less) may be used to build the model. Some datasets may not include any PHI or PII data.

Data may be provided in both numerical and categorical forms, which may be segregated into different data forms while developing the model input data. In various implementations, the large number of variables may be reduced to improve the prediction capability of the model, such as reducing over 1500 variables to fewer than 100 variables. This may produce accurate results when predicting a test dataset, which may be segregated from a whole dataset according to an 80/20 ratio (or any other suitable ratio).

Input variables included in the prediction model may include, for example, ages of employees, annuity data, lengths of time at a current residence, marketing data for different age ranges, low risk investment data, health insurance data, etc. The model output may include an individual identifier, a retirement probability, and a decile in which the user falls, so that the user may be contacted according to decile ranges. For example, if a user is predicted to be in decile 1, more attention may be applied to the user as compared to later decile users. In this example, the lower deciles (such as deciles 1-4) may be more likely to take an interest in advertised insurance, while higher deciles (such as decile 5 or higher) may be less likely to select an advertised insurance product.

In various implementations, data may be preprocessed using any suitable techniques. For example, a YLM dataset which may have more than 1500 variables, which may include many discrepancies. The preprocessing may imputing values for all missing variables where the number of entries that are missing the variable is less than a threshold (such as 45%) of the total entries. Preprocessing may then remove all variables that have missing values for more entries than the threshold count.

Missing values may be imputed on the basis of the distribution of the variable across the dataset. For example, if the variable is left or right skewed, missing values may be imputed using the median of the data for the known values, and missing categorical variables values may be imputed using the mode of the data for the known values. Outliers may be removed from the dataset. For categorical variable, subclasses may be have grouped into bins, because label encoding will create many dummy variables and it may not be feasible for the model to learn a dataset that includes many more variables for a model that is too complex.

After the preprocessing, data may be stored in a desired format without any outliers, without any missing values. There may not be any input variables that are co-related with an output variable, such that the model can focus on the input variables that have a highest impact on the output variables. After training the model, a testing dataset may be used to check the accuracy of the model, and hyper-parameters may be tuned as desired.

In various implementations, a model may be created with Python using multiple algorithms. The best model performing model may be selected among all tested models (based on the accuracy of the model), and a pickle file may be created and put into a gitlab storage location for a specified project. Once the model is placed into the gitlab location, YLM data may be scored according to the following procedure. Data may be loaded from the YLM database source onto a platform. The data may be preprocessed according to a script used for it, placed in gitlab. After performing the preprocessing steps, the model may be scored, and an output of the model is written in a file and stored at a specific output storage location.

In various implementations, a model may be used to generate a predication of whether the prospect will be on time in terms of their individual enrollment period. This may include a binary classification model in which that determines whether the individual enrolled in a retirement insurance option during his/her enrollment period, or not. In order to determine this behavior of the individual, one or more datasets that cover the previous behavior of the individual are used. For example, a YLM may store individual census and lifestyle variables. Some of the key features that are included in the YLM dataset may include, but are not limited to, household composition, income and wealth levels, concentration of 65+ year olds, nursing home status, and power of attorney status.

The data may also include a response variable with a value of 1 or 0, which is used by the model for training purposes to predict the accuracy of the model while testing the model. As there are more than 1500 variables in the YLM dataset and not all of those are helpful in predicting the response, statistical methods may be used to decrease the variables from 1500 to a smaller amount, such as approximately 100 (or more or less). The model may then be trained with a low number of features, and avoid potential dimensionality issues. Backward selection may be used to find a best training sample, which may be processed by a random forest algorithm to find variable importance. A top number of variables, such as the top 100 variables, may be selected to use PCA for further analysis.

Multiple models may be tested initially, such as a logistic regression model. A base accuracy of each model may be determined base without any hyper-tuning. Next, model accuracy may be tested after hyper-tuning to increase the accuracy. Random forest algorithms, svm algorithms, nearest neighbor algorithms, etc., may be used to find a best model. In various implementations, the random forest algorithm may provide a best result.

In various implementations, a basic random forest algorithm may be used, with slight modifications. In a bagging algorithm like random forest, data may be split on the bases of entropy or Gini index (depending upon application and usage). In some cases, features scaling may be performed to provide a better prediction from the algorithm, because the scaled data includes imputed missing values that are assigned into multiple bins.

If there are N observations and M features in the training data set, a random sample may be taken from the dataset with replacement. A subset of M features may be selected randomly, and whichever feature gives the best split may be used to split the node iteratively. The tree may be grown to a largest size, and the steps may be repeated to generate n trees, where an overall prediction is provided based on an aggregation of predictions from n number of trees. A training and run-time complexity may be defined as training time=$O(\log(nd)*k)$, run time=$O(depth*k)$, and space=$O$(store each $DT*K$).

Customer Segmentation Model

Figure 28:
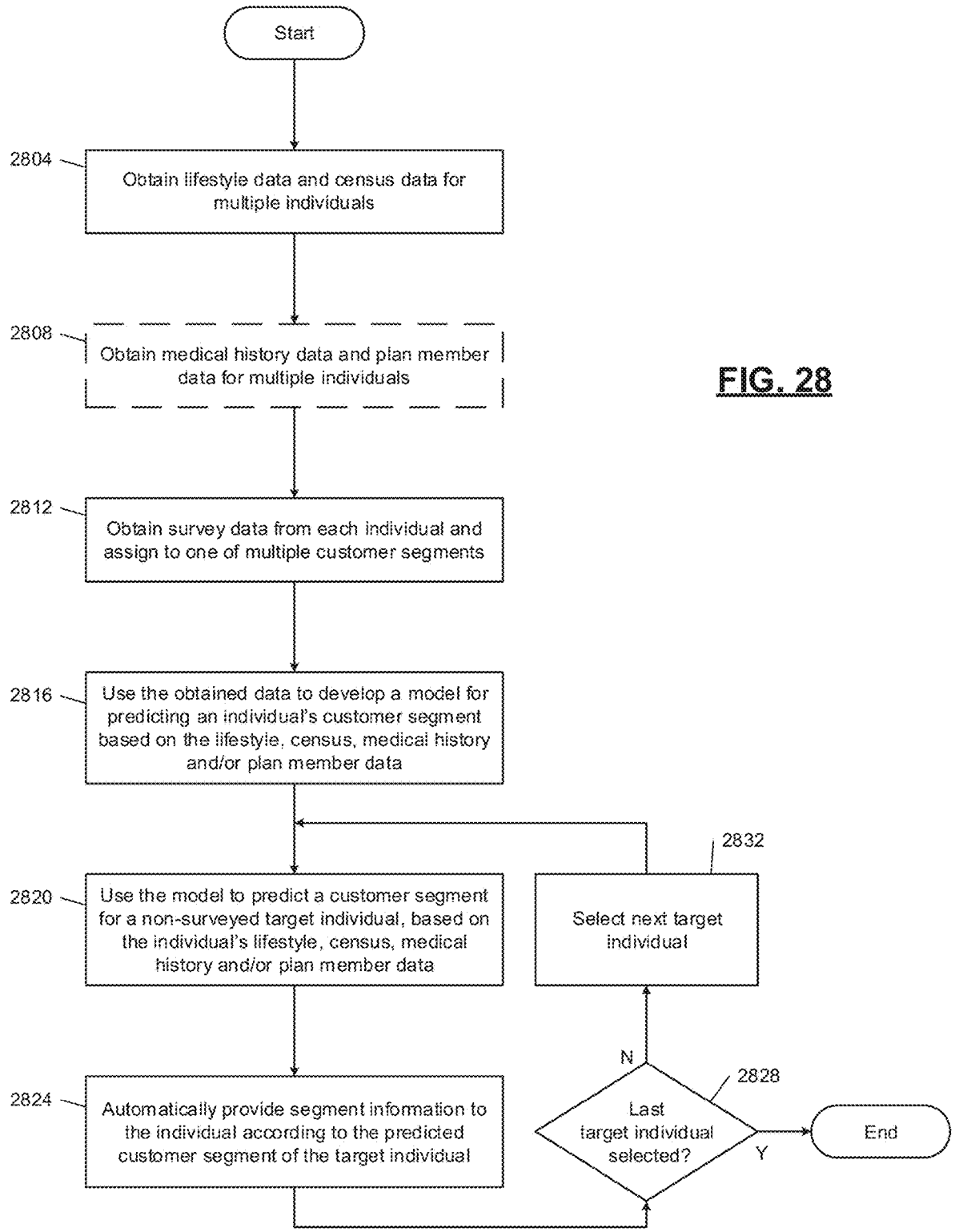
FIG. 28 is a flowchart depicting an example method of implementing a machine learning model for generating a customer segment prediction output.

FIG. 28 illustrates an example process for generating a machine learning model for predicting a customer segment for an individual. At 2804, control begins by obtaining lifestyle and census data for multiple individuals (for example, finance information, fitness information, household information, purchase history, and census attributes). Medical history data (for example, treatment history, chronic conditions, and tobacco smoking habits), and plan member data (for example, gender, address, age, work industry, medical claims cost utilization, and enrollment information) is optionally obtained for the multiple individuals at 2808.

In various implementations, the obtained data may include over seven hundred variables describing different attributes of the individuals. The data may be obtained from internal health plan provider databases, from external databases, etc. For example, the model may be trained with historical feature vector inputs to generate a customer segment likelihood output, wherein the historical feature vector inputs include structured customer segment data and historical profile data structures specific to multiple historical customer entities, and the historical profile data structures include at least one of historical structured lifestyle data, historical structured census data, historical structured medical history data, and historical structured health plan data.

At 2812, control obtains survey data from each individual and assigns each individual to one of multiple customer segments, based on the survey data. For example, each customer segment may classify different details regarding the lifestyle of the customer, such as active or inactive, single or married, working or non-working, older or younger, etc. In some implementations, there may be eight defined customer segments.

Control proceeds to 2816 to use the obtained data to develop a model for predicting an individual's customer segment based on the lifestyle, census, medical history and/or plan member data. At 2820, control uses the model to predict a customer segment for a non-surveyed target individual, based on the non-surveyed target individual's lifestyle, census, medical history and/or plan member data. For example, the model may generate a customer segment likelihood output is indicative of a likelihood that the customer entity belongs to a specific customer segment.

In some implementations, the model may take into account externally available data for an individual, as well as internal data of the health plan provider such as medical history, plan member data, etc. In other implementations, the model may only receive the externally available data, in order to predict customer segments for individuals who do not have medical history or plan member data with the health plan provider.

At 2824, control automatically provides information to the individual according to the predicted customer segment of the individual. This may include any suitable automated process for generating emails, social media advertisements, digital advertisement purchases, entertainment content streaming advertisements, etc., that are tailored to the specific customer segment identified for the target individual. Because the target individual has been classified in a particular customer segment, the target individual is more likely to respond if they receive campaign materials that are tailored to their specific customer segment.

At 2828, control determines whether a last target individual has been selected. If so, the process ends. If not, control proceeds to 2832 to select a next target individual, and then uses the model again at 2820 to predict a customer segment for the next target individual.

The model may be developed using any suitable machine learning techniques. For example, the model may search the Kth nearest customers from a target record in a variables space, to generate a top similar group with k observations. This top similar group be defied as a score target, and a customer may be scored based on a similarity with the group. All variables may be replaced in the target record with relative ones from the top similarity group, one by one.

In some implementations, each customer may be viewed as a point in a coordinate system, which consists of axes from internal data variables. The space is then divided into eight separated regions, each representing one of the customer segments. Whoever falls in a region that represents a segment is predicted to be in that segment.

Centroids may be estimated for each segment, and then for each customer, eight Mahalanobis distances may be calculated between the customer and the centroids of each segment. Using the eight distances, boundaries may be formed to separate the regions. When equal covariance is assumed in each segment, the boundaries may be linear functions, and therefore hyper-planes in a high dimensional space. This technique may be considered as a linear discriminant analysis.

Figure 29:
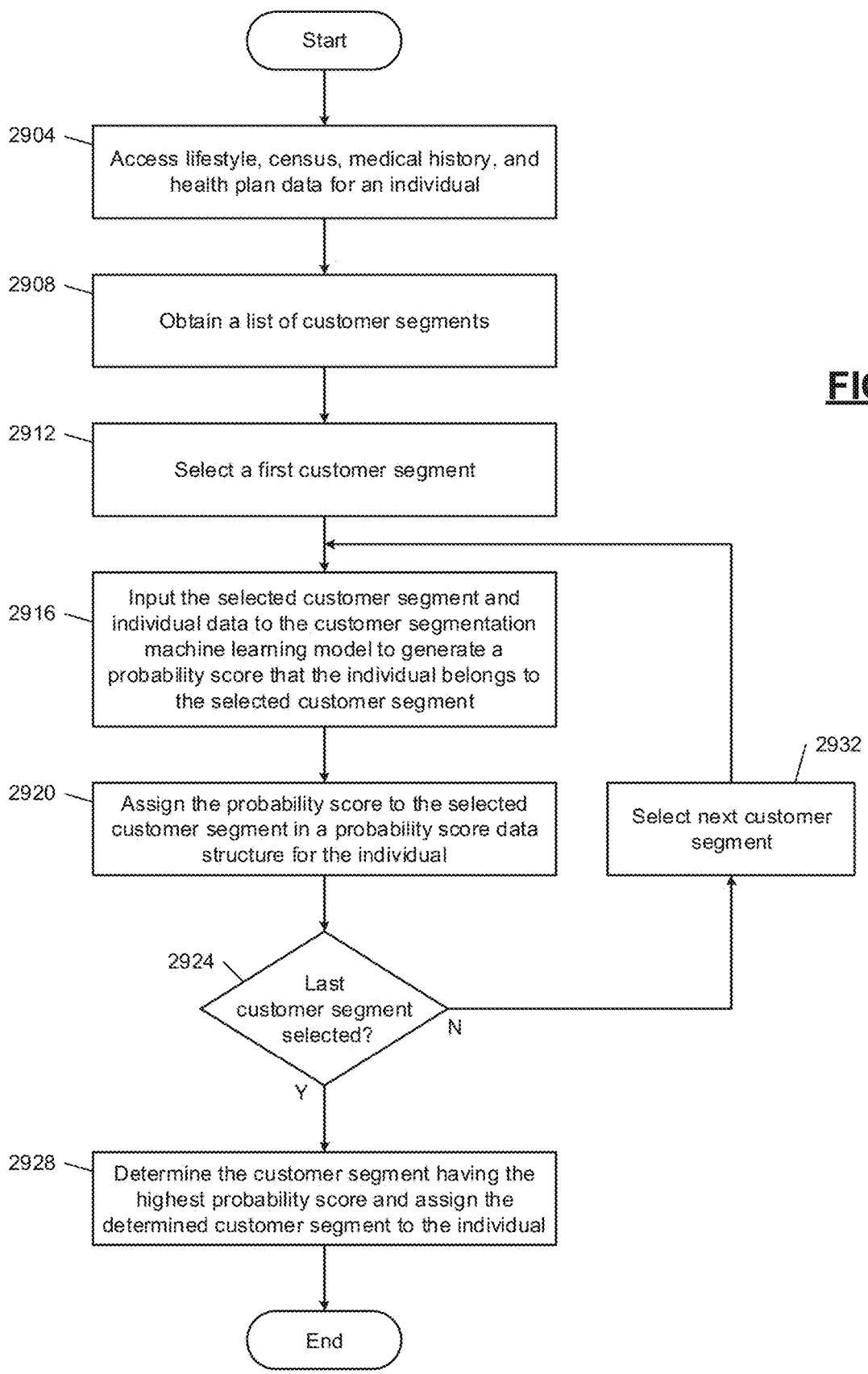
FIG. 29 is a flowchart depicting an example method of implementing a machine learning model for generating a customer segment prediction output by assigning probability scores to multiple customer segments.

FIG. 29 is a flowchart depicting an example method of implementing a machine learning model for generating a customer segment prediction output by assigning probability scores to multiple customer segments. At 2904, control begins by accessing lifestyle, census, medical history, and health plan data for an individual. At 2908, control obtains a list of customer segments, and then control selects the first customer segment at 2912.

At 2916, control inputs the selected customer segment and individual data to the customer segmentation machine learning model, to generate a probability score that the individual belongs to selected customer segment. At 2920, control assigns a customer segment likelihood output to the selected customer segment in a segment score data structure for the individual. For example, a table may include multiple columns that each include an entry storing a customer segment likelihood output corresponding to a different customer segment.

Control then determines, at 2924, whether a last customer segment has been selected. If not, control selects the next customer segment at 2932, and then returns to 2916 to input the selected customer segment and individual data to the customer segmentation machine learning model. If control determines at 2924 that the last customer same has been selected, control proceeds to 2928 to determine the customer segment having the highest probability score, and assigns the determine customer segment to the individual. For example, control may determine in which of all customer segments the individual received the highest probability score, and classify the individual as belonging to the customer segment based on the highest received probability score.

Effective marketing may include assigning the right resources to potential and existing customers, to facilitate maximum return. Marketing analysts strategize content creation and targeting tactics, based on the customer profiles for each business sector. Segmentation is used to fulfill this goal. Business sectors can leverage segment understanding to target, reach, communicate, and service customers effectively. Understanding product preferences of segments assists in developing products and marketing programs that consider the behaviors, attitudes, needs and characteristics of the customers. Segmentations may be product specific. Segmentation look-alike classification models may be built based on market research clustering results.

In various implementations, a marketing agency may perform focus group study on a small specific group of individuals. Using study feedback, an unsupervised learning model may be used to cluster individuals into a set number of segments with distinctive characteristics. Individual identifiers and segment labels may be appended, and provided as final deliverables. Personal identifier information may be sent to internal and/or external data providers. Additional data may be appended to the individual identifier and label after a PII/PHI masking. Using the dataset, a multi-class look-alike classification model may be implemented to assign segment labels to a broader data points.

In various implementations, primary data may be collected by a marketing agency directly. Survey questions are designed to reveal certain characteristics of a business segment customer. A survey for each business segment may differ, depending on a utility and desired output. Example surveys may include structured survey response data about health status (such as overall health, risk indicators, current diagnoses, and health-living impact), health engagement (such as proactivity in healthcare, personal health focus and behaviors, a need for change), health insurance views (such as health insurance attitudes, perceived value, interaction with carrier, and new ideas), provider attributes (such as healthcare utilization, provider interaction, and health information exchange), personal values and life outlook (such as life goals, and a most trusted source of news), and wealth and financial products use (such as financial activities like investing in stock or real estate).

Some data may come from internal databases of a health insurance provider. For example, a segmentation look-alike classification can be built on internal data, external data, or both. Example internal features may include an age at benefit enrollment date, an average incurred claim amount, average numbers of different types of health visits, etc.

External data sources may allow for a deeper and broader insight regarding targeted individuals. Structured lifestyle data and structured census data are the two types of data that can be used as an input for a multi-class look-alike classification model, although various implementations may include any suitable data types. Example input variables include, but are not limited to, a total number of vacant housing units, a percentage of children in specified age ranges, a percent of the working population that works in the county in which they reside or outside of the state in which they reside, a percentage of the working population that rides a bicycle to work, a percentage of households living with and having responsibility for their own grandchildren, a percentage of households that include specified numbers of people, a percentage of the population enrolled in private school, a percentage of the population that speaks English only, income levels of households, self-employed households, types of household structures, likelihood of being involved with specified activities, outstanding loan information, scored interest feedback in various activities, demographic data, education level data, numbers of vehicles owned, etc.

For each segment, the model may predict the probability that a person belongs to the segment. As a model output, each record may be assigned N probability scores, where N is the number of predefined segments. The segment with the highest probability is selected as the predicted segment for the consumer. For example, if there are seven segments, and the determined probability that a customer belongs to Segment 4 is 30%, which is the highest among all the segment scores, the customer may be predicted as a Segment 4 customer.

The segmentation model may use tabular data input in a numerical format. Depending on the needs of an application, a data source may be merged and rolled up to an individual level. A dataset with unique identifiers for each individual may be created. Datasets with different sets of variables may be mapped into a format of selected features of the classification model. A standard set of preprocessing steps may be used to transform the variables into a model-ingestible format. The preprocessing may include, but is not limited to, a data type check, a missing value imputation, one hot encoding of categorical variables, and data scaling. A model may be packaged as a Docker container. The image may be deployed to a company cloud infrastructure in the scoring process, where targeted individuals are collected from a data store and loaded into the container.

In various implementations, a target audience may be clustered into characteristic segments. A target audience may refer to internal customers and/or external prospects, depending on whether the objective is retention or acquisition. A survey may be conducted to collect information pertaining to a particular application at hand. Then segments may be generated from the survey, using an unsupervised learning procedure called segmentation. Because survey data may not be available in the future, a process may be performed to learn segment labels from existing data according to a supervised learning procedure called classification. In order to enable such machine learning, two sets of variables may be simultaneously collected from the target audience. In marketing, the task may be referred to as look-alike modeling. After training, unseen segment labels may be predicted using existing data.

For example, there may be two sets of data, such as $\vec{X}=[X_1, X_2, \ldots, X_m]'$ from the survey data and $Y=[Y_1, Y_2, \ldots, Y_l]'$ from the existing data, where m and l are the number of variables in the survey data and the existing data, respectively. $\vec{X}$ and $\vec{Y}$ may be random vectors, while $X_j$ and $Y_k$ are random variables. If there are n observations in the target audience, and $\vec{X}_i=[X_{i1}, \ldots, X_{im}]'$ and $\vec{Y}_i=[Y_{i1}, \ldots, Y_{il}]'$ are variables in the ith observation, then the training data is $D=\{\vec{X}_i, \vec{Y}_i\}_{i=1}^n$. The tabular form of training data is illustrated in Table 1.

TABLE 1

| Segmentation Variables | | Classification Variables | | | |
|---|---|---|---|---|---|
| $X_{i1}$ | ... $X_{im}$ | $Y_{i1}$ | ... | $Y_{il}$ | Training Data |
| ... | ... ... | ... | ... | ... | $D = \{\overline{X}_i, \overline{Y}_i\}_{i=1}^n$ |
| $X_{n1}$ | ... $X_{nm}$ | $Y_{n1}$ | ... | $Y_{n1}$ | |

Note that $\vec{X}$ is used for segmentation and $\vec{Y}$ is used for classification. Let $F(\vec{X})=f(\vec{X}; \theta_f)$ be the segmentation model such as k-means clustering. It is trained to set similar members of $\{\vec{X}_i\}_{i=1}^n$ in the same group and dissimilar members in different groups. The parameters $\theta_f$ include similarity measures and a number of segments. The settings depend on data and business objectives. Assume that the parameter F is determined, and let $G(\vec{Y})=g(\vec{Y}; \theta_g)$ be the classifier, such as multinomial logit. It is trained to assign $\{\vec{Y}_i\}_{i=1}^n$ to predicted segments. The parameters $\theta_g$ include loss function and classifier parameters. The objective is to find a value for G that minimizes the expected loss based on a true label $F(\vec{X})$ and a prediction $G(\vec{Y})$. This is illustrated in Equation (6):

$$\hat{G} = \arg\min_G \frac{1}{n}\sum_{i=1}^n L(F(\vec{X}_i), G(\vec{Y}_i)) \qquad \text{Equation (6)}$$

The estimator $\hat{G}$ is learned from F for the same target audience, but it is based on a different set of variables. For the training data D, the expectation operation $\mathbb{E}[\cdot]$ is replaced by a sample mean illustrated in Equation (7):

$$\hat{G} = \arg\min_G \frac{1}{n}\sum_{i=1}^n L(F(\vec{X}_i), G(\vec{Y}_i)) \qquad \text{Equation (7)}$$

An example loss function is the classification error L(y, ŷ)=$\mathbb{I}$(y≠ŷ), where $\mathbb{I}$(y≠ŷ)=1 if y≠ŷ and $\mathbb{I}$(y+ŷ)=0 if y=ŷ. $\hat{G}(\vec{Y}^{new})$ is the predicted segment, where $\vec{Y}^{new}$ is a new observation with a variable vector $\vec{Y}$. If there are latent factors $\vec{Z}$ that drive $\vec{X}$ and $\vec{Y}$, the approximation of the segmentation model F by the classification model G is valid. The error is governed by the value of $$l = \frac{1}{n}\sum_{i=1}^{n} L(F(\vec{X}_i), G(\vec{Y}_i)).$$

The lookalike modeling is reduced to the estimation of function form G and the selection of variables $\vec{Y}$. If the training data D is representative of $\vec{Y}^{new}$ and the value of l is small, the process is expected to be generalizable.

A survey may be valuable to a company to provide insights into customers and prospects for any particular application, but may require costly data that is generally not available in the future. In order to address this issue, existing data may be used with a segmentation look-alike model that is only based on a set of variables that are expected to always exist in available data. The learning model may generate a predicted segment per member of target audience. The model may bypass unavailability of survey variables, using a scalable, data-driven and reproducible framework, in areas such as insurance marketing analytics.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computerized method of automatic distributed communication, the method comprising:
   training a first machine learning model with historical feature vector inputs to generate a title score output using classifications for supervised learning, wherein:
   the historical feature vector inputs include historical profile data structures specific to multiple historical entities,
   the historical profile data structures include structured title data and structured response data, the structured title data including a job title matrix; and
   training the first machine learning model includes:
      classifying each one of the multiple historical entities as a decision entity or a non-decision entity according to the structured response data associated with the historical entity;
      duplicating at least a portion of classified decision entity records in training data for the first machine learning model;
      down-sampling at least a portion of classified non-decision maker records in the training data for the first machine learning model;
      training a variable selection algorithm on the job title matrix to determine multiple significant keywords;
      selecting a specified number of highest scoring ones of the determined multiple significant keywords; and
      training a multinomial naive Bayes algorithm on a term frequency matrix of the selected specified number of keywords;
   training a second machine learning model with the historical feature vector inputs to generate a background score output, wherein the historical profile data structures include structured background data, the structural background data includes a term frequency matrix, and training the second machine learning model includes:
      duplicating at least a portion of classified decision entity records in training data for the second machine learning model;
      down-sampling at least a portion of classified non-decision maker records in the training data for the second machine learning model; and
      inputting the term frequency matrix and the structured background data into a binary classification algorithm;
   obtaining a set of entities;
   for each entity in the set of entities:
      obtaining structured title data associated with the entity from a structured title database;
      generating a title feature vector input according to the obtained structured title data;
      processing, by the first machine learning model, the title feature vector input to generate the title score output, wherein the title score output is indicative of a likelihood that the entity is a decision entity according to the structured title data associated with the entity;
      obtaining structured background data associated with the entity from a structured background database;
      generating a background feature vector input according to the obtained structured background data;
      processing, by the second machine learning model, the background feature vector input to generate the background score output, wherein the background score output is indicative of a likelihood that the entity is a decision entity according to the structured background data associated with the entity;
      combining the generated background score output and the generated title score output to determine a decision score output;
      selectively including the entity in a subset of entities based on a comparison of the decision score output to a threshold value; and for each entity in the subset of entities, automatically distributing structured campaign data to the entity.

2. The method of claim 1 wherein the training of the second machine learning model includes training the second machine learning model using the classifications for supervised learning.

3. The method of claim 1 further comprising transforming a user interface to display each entity in the subset of entities.

4. The method of claim 1 wherein the first machine learning model includes at least one of a variable selection machine learning algorithm and a binary classification machine learning algorithm.

5. The method of claim 1 wherein the second machine learning model includes a binary classification machine learning algorithm.

6. A computer system comprising:
  memory hardware configured to store a machine learning model, historical feature vector inputs, and computer-executable instructions, wherein:
    the historical feature vector inputs include historical profile data structures specific to multiple historical entities, and
    the historical profile data structures include structured title data, structured response data, and structured background data, the structured title data including a job title matrix, and the structural background data including a term frequency matrix; and
  processor hardware configured to execute the instructions, wherein the instructions include:
  training a first machine learning model with the historical feature vector inputs to generate a title score output using classifications for supervised learning, wherein training the first machine learning model includes:
    classifying each one of the multiple historical entities as a decision entity or a non-decision entity according to the structured response data associated with the historical entity;
    duplicating at least a portion of classified decision entity records in training data for the first machine learning model;
    down-sampling at least a portion of classified non-decision maker records in the training data for the first machine learning model;
    training a variable selection algorithm on the job title matrix to determine multiple significant keywords;
    selecting a specified number of highest scoring ones of the determined multiple significant keywords; and
    training a multinomial naive Bayes algorithm on a term frequency matrix of the selected specified number of keywords;
  training a second machine learning model with the historical feature vector inputs to generate a background score output, wherein training the second machine learning model includes:
    duplicating at least a portion of classified decision entity records in training data for the second machine learning model;
    down-sampling at least a portion of classified non-decision maker records in the training data for the second machine learning model; and
    inputting the term frequency matrix and the structured background data into a binary classification algorithm;
  obtaining a set of entities;
  for each entity in the set of entities:
    obtaining structured title data associated with the entity from a structured title database;
    generating a title feature vector input according to the obtained structured title data;
    processing, by the first machine learning model, the title feature vector input to generate the title score output, wherein the title score output is indicative of a likelihood that the entity is a decision entity according to the structured title data associated with the entity;
    obtaining structured background data associated with the entity from a structured background database;
    generating a background feature vector input according to the obtained structured background data;
    processing, by the second machine learning model, the background feature vector input to generate the background score output, wherein the background score output is indicative of a likelihood that the entity is a decision entity according to the structured background data associated with the entity;
    combining the generated background score output and the generated title score output to determine a decision score output;
    selectively including the entity in a subset of entities based on a comparison of the decision score output to a threshold value; and
  for each entity in the subset of entities, automatically distributing structured campaign data to the entity.

7. The computer system of claim 6 wherein the training of the second machine learning model includes training the second machine learning model using the classifications for supervised learning.

8. The computer system of claim 6 wherein the instructions further include transforming a user interface to display each entity in the subset of entities.

9. The computer system of claim 6 wherein the first machine learning model includes at least one of a variable selection machine learning algorithm and a binary classification machine learning algorithm.

10. The computer system of claim 6 wherein the second machine learning model includes a binary classification machine learning algorithm.

\* \* \* \* \*